(12) United States Patent
Huang et al.

(10) Patent No.: US 7,910,590 B2
(45) Date of Patent: Mar. 22, 2011

(54) CYCLIC AMINE BACE-1 INHIBITORS HAVING A HETEROCYCLIC SUBSTITUENT

(75) Inventors: Ying Huang, East Brunswick, NJ (US); Guoqing Li, Belle Mead, NJ (US); Ulrich Iserloh, Hoboken, NJ (US); Andrew Stamford, Chatham Township, NJ (US); Corey Strickland, Martinsville, NJ (US); Johannes H. Voigt, Union, NJ (US); Jianping Pan, Monmouth Junction, NJ (US)

(73) Assignee: Schering Corporation, Kenilworth, NJ (US)

(*) Notice: Subject to any disclaimer, the term of this patent is extended or adjusted under 35 U.S.C. 154(b) by 0 days.

(21) Appl. No.: 12/490,884

(22) Filed: Jun. 24, 2009

(65) Prior Publication Data

US 2009/0312341 A1 Dec. 17, 2009

Related U.S. Application Data

(62) Division of application No. 10/911,030, filed on Aug. 4, 2004, now Pat. No. 7,598,250.

(60) Provisional application No. 60/493,646, filed on Aug. 8, 2003.

(51) Int. Cl.
A61K 31/496 (2006.01)
A61K 31/506 (2006.01)

(52) U.S. Cl. .......... 514/252.14; 514/254.01; 514/254.05

(58) Field of Classification Search .................. None
See application file for complete search history.

(56) References Cited

U.S. PATENT DOCUMENTS

| | | | |
|---|---|---|---|
| 6,683,091 B2 | 1/2004 | Asberom et al. | |
| 2004/0171614 A1 | 9/2004 | Pissarnitski et al. | |

FOREIGN PATENT DOCUMENTS

| | | |
|---|---|---|
| WO | WO 8903842 | 5/1989 |
| WO | WO 9518104 | 6/1995 |
| WO | WO 0007995 | 2/2000 |
| WO | WO 0050391 | 8/2000 |
| WO | WO 0056335 | 9/2000 |
| WO | WO 0202505 | 1/2002 |
| WO | WO 0202506 | 1/2002 |
| WO | WO 0202512 | 1/2002 |
| WO | WO 0202518 | 1/2002 |
| WO | WO 0202520 | 1/2002 |
| WO | WO 02088101 | 11/2002 |
| WO | WO 03013527 | 2/2003 |
| WO | WO 03018543 | 3/2003 |
| WO | WO 03027068 | 4/2003 |
| WO | WO 03045913 | 6/2003 |
| WO | WO 03066592 | 8/2003 |

OTHER PUBLICATIONS

Hamada et al. Expert Opin.Drug Discov. 4(4), p. 391-416 (2009).*
Baltaïef et al, (Z)-Dimethyl α-(Bromomethyl)fumarate, an Efficient Intermediate for the Selective Synthesis of Dimethyl 3-Alkyl Itaconates and 2-Alkyl 3-Carbomethoxy-γ-Lactams, Tetrahedron, vol. 55, pp. 3949-3958 (1999).

(Continued)

Primary Examiner — Emily Bernhardt
(74) Attorney, Agent, or Firm — Keith D. MacMillan

(57) ABSTRACT

Disclosed are novel compounds of the formula

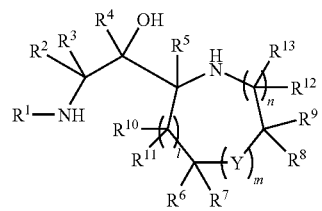

or a pharmaceutically acceptable salt or solvate thereof, wherein
$R^1$ is

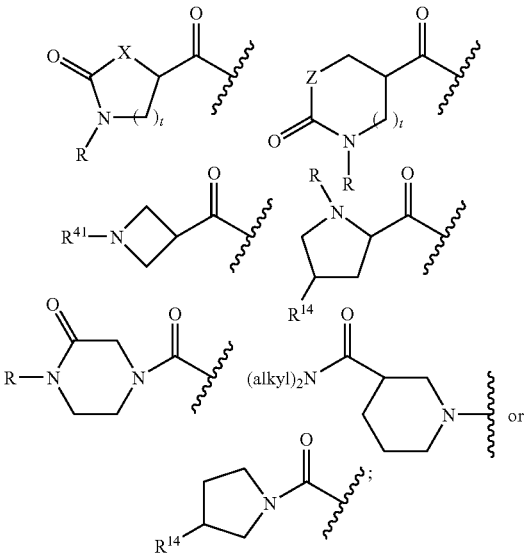

X is —O—, —C($R^{14}$)$_2$— or —N(R)—;
Z is —C($R^{14}$)$_2$— or —N(R)—;
t is 0, 1, 2 or 3;
each R and $R^2$ is independently H, alkyl, cycloalkyl, cycloalkylalkyl, aryl, heteroaryl, heterocycloalkyl, arylalkyl, heteroarylalkyl, heterocycloalkylalkyl, alkenyl or alkynyl;
each $R^{14}$ is H, alkyl, alkenyl, alkynyl, halo, —CN, haloalkyl, cycloalkyl, cycloalkylalkyl, aryl, heteroaryl, heterocycloalkyl, arylalkyl, heteroarylalkyl, heterocycloalkylalkyl, —$OR^{35}$, —N($R^{24}$)($R^{25}$) or —$SR^{35}$;
$R^{41}$ is alkyl, cycloalkyl, —$SO_2$(alkyl), —C(O)-alkyl, —C(O)-cycloalkyl or -alkyl-NH—C(O)$CH_3$;
and the remaining variables are as defined in the specification. Also disclosed are pharmaceutical compositions comprising the compounds of formula I and methods of treating cognitive or neurodegenerative diseases with compounds of formula I. Also disclosed are pharmaceutical compositions and methods of treatment comprising compounds of formula I in combination with other agents useful in treating cognitive or neurodegenerative diseases.

31 Claims, No Drawings

OTHER PUBLICATIONS

Bellier et al, "Synthesis and Biological Properties of New Constrained CCK-B Antagonists: Discrimination of Two Affinity States of the CCK-B Receptor on Transfected CHO Cells", J. Med. Chem., vol. 40, pp. 3947-3956 (1997).

Berg et al, "Pharmaceutical Salts", Journal of Pharmaceutical Sciences, vol. 66, pp. 1-19 (1977).

Chackalamannil et al, "Total Synthesis of (+)-Himbacine and (+)-Himbeline", J. Org. Chem., vol. 64, pp. 1932-1940 (1999).

Danielmeier et al, "Efficient Pathways to ($R$)- and ($S$)-5-Hydroxymethyl-2-oxazolidinone and Some Derivatives", Tetrahedron: Asymmetry, vol. 6, No. 5, pp. 1181-1190 (1995).

Dinsmore et al, "3,8-Diazabicyclo[3.2.1]octan-2-one Peptide Mimetics: Synthesis of a Conformationally Restricted Inhibitor of Farnesyltransferase", Organic Letters, vol. 3, pp. 865-868 (2001).

Ezquerra et al, "Stereoselective Double Alkylation of Ethyl $N$-Boc-pyroglutmate", J. Org. Chem., vol. 59, pp. 4327-4331 (1994).

Gould, Salt Selection for Basic Drugs, International Journal of Pharmaceutics, vol. 33, pp. 201-217 (1986).

Hanessian et al, "The Power of Visual Imagery in Synthesis Planning. Stereocontrolled Approaches to CGP-60536B, a Potent Renin Inhibitor", J. Org. Chem., vol. 67, pp. 4261-4274 (2002). Hayashi et al, "Studies on Angiotensin Converting Enzyme Inhibitors. 4. Synthesis and Angiotensin Converting Enzyme Inhibitory Activities of 3-Acyl-1-alkyl-2-oxoimidazolidine-4-carboxylic Acid Derivatives", J. Med. Chem., vol. 32, pp. 289-297 (1989).

Hock et al, "Generation of Antibodies Specific for β-amyloidby Vaccination of Patients with Alzheimer Disease", Nature Medicine, vol. 8, pp. 1270-1275 (2002).

Hom, "Bicyclic Aminoimidazolone BACE1 Inhibitors", Expert Opin. Ther. Patents, vol. 17, No. 6, pp. 737-740 (2007).

Itoh et al, "Asymmetric Synthesis of (−)-Adaline", Organic Letters, vol. 4, No. 15, pp. 2469-2472 (2002).

Kruse et al, "Multisubstrate Inhibitors of Dopamine β-Hydroxylase. 2. Structure-Activity Relationships at the Phenethylamine Binding Site", J. Med. Chem., vol. 30, pp. 486-494 (1987).

Lowe et al, "Amino Acid Bearing Nucleobases for the Synthesis of Novel Peptide Nucleic Acids", J. Chem. Soc., Perkin Trans. 1, pp. 539-546 (1997).

MacDonald et al, "Discovery of Further Pyrrolidine *trans*- Lactams as Inhibitors of Human Neutrophil Elastase (HNE) with Potential as Development Candidates and the Crystal Structure of HNE Complexed with an Inhibitor (GW475151)", J. Med. Chem., vol. 45, pp. 3878-3890 (2002).

McGaughey et al, "Structure-Guided Design of β-Secretase (BACE-1) Inhibitors", Expert Opin. Drug Discovery, vol. 2, No. 8, pp. 1129-1138 (2007).

Melnikova, "Therapies for Alzheimer's Disease", Nature Review Drug Discovery, vol. 6, pp. 341-342 (2007).

Pettit et al, "The Dolastatins; 18: Stereospecific Synthesis of Dolaproine", Synthesis, pp. 719-725 (1996).

Pfeiffer et al, "A Short Synthesis of 4-Imidazolidinone", Liebigs Ann. Chem., pp. 993-995 (1988).

Roggo, "Inhibition of BACE, A Promising Approach to Alzheimer's Disease Therapy", Current Topics in Medicinal Chemistry, vol. 2, pp. 359-370 (2002).

Tian et al, "An Efficient Scalable Process for teh Synthesis of N-Boc-2-*tert*-butyldimethylsiloxypyrrole", Organic Process Research & Development, vol. 6, pp. 416-418 (2002).

Stahl, Handbook of Pharmaceutical Salts: Selection, and Use, Int'l. Union of Pure and Applied Chemistry, pp. 330-331 (2002).

Vippagunta et al, "Crystalline Solids", Advanced Drug Delivery Reviews, vol. 48, pp. 3-26 (2001).

Webb et al, "Conformationally Restricted Arginine Analogues", J. Org. Chem., vol. 56, pp. 3009-3016 (1991).

International Search Report for International Application No. PCT/US2004/025018, mailed Aug. 22, 2005.

* cited by examiner

CYCLIC AMINE BACE-1 INHIBITORS HAVING A HETEROCYCLIC SUBSTITUENT

CROSS REFERENCE TO RELATED APPLICATION

This application is a Divisional application based on and claiming priority to U.S. application Ser. No. 10/911,030, filed Aug. 4, 2004, which claims the benefit of U.S. Provisional Application 60/493,646, filed Aug. 8, 2003, each of which application is incorporated by reference.

FIELD OF THE INVENTION

This invention relates to substituted cyclic amine BACE-1 inhibitors having a heterocyclic substituent, pharmaceutical compositions comprising said compounds, and their use in the treatment of Alzheimer's disease.

BACKGROUND

Alzheimer's disease (AD) is a progressive neurodegenerative disease that is ultimately fatal. Disease progression is associated with gradual loss of cognitive function related to memory, reasoning, orientation and judgment. Behavioral changes including confusion, depression and aggression also manifest as the disease progresses. The cognitive and behavioral dysfunction is believed to result from altered neuronal function and neuronal loss in the hippocampus and cerebral cortex. The currently available AD treatments are palliative, and while they ameliorate the cognitive and behavioral disorders, they do not prevent disease progression. Therefore there is an unmet medical need for AD treatments that halt disease progression.

Pathological hallmarks of AD are the deposition of extracellular β-amyloid (Aβ) plaques and intracellular neurofibrillary tangles comprised of abnormally phosphorylated protein tau. Individuals with AD exhibit characteristic Aβ deposits, in brain regions known to be important for memory and cognition. It is believed that Aβ is the fundamental causative agent of neuronal cell loss and dysfunction which is associated with cognitive and behavioral decline. Amyloid plaques consist predominantly of Aβ peptides comprised of 40-42 amino acid residues, which are derived from processing of amyloid precursor protein (APP). APP is processed by multiple distinct protease activities. Aβ peptides result from the cleavage of APP by β-secretase at the position corresponding to the N-terminus of Aβ, and at the C-terminus by γ-secretase activity. APP is also cleaved by α-secretase activity resulting in the secreted, non-amyloidogenic fragment known as soluble APP.

An aspartyl protease known as BACE-1 has been identified as the β-secretase responsible for cleavage of APP at the position corresponding to the N-terminus of Aβ peptides.

Accumulated biochemical and genetic evidence supports a central role of Aβ in the etiology of AD. For example, Aβ has been shown to be toxic to neuronal cells in vitro and when injected into rodent brains. Furthermore inherited forms of early-onset AD are known in which well-defined mutations of APP or the presenilins are present. These mutations enhance the production of Aβ and are considered causative of AD.

Since Aβ peptides are formed as a result β-secretase activity, inhibition of the BACE-1 enzyme should inhibit formation of Aβ peptides. Thus inhibition of BACE-1 is a therapeutic approach to the treatment of AD and other cognitive and neurodegenerative diseases caused by Aβ plaque deposition.

Substituted amine BACE-1 inhibitors are disclosed in WO 02/02505, WO 02/02506, WO 02/02512, WP 02/02518 and WO 02/02520. Renin inhibitors comprising a (1-amino-2 hydroxy-2-heterocyclic)ethyl moiety are disclosed in WO 89/03842. WO 02/088101 discloses BACE inhibitors functionally described as being comprised of four hydrophobic moieties, as well as series of compounds preferably comprising a heterocyclic or heteroaryl moiety.

SUMMARY OF THE INVENTION

The present invention relates to compounds having the structural formula I

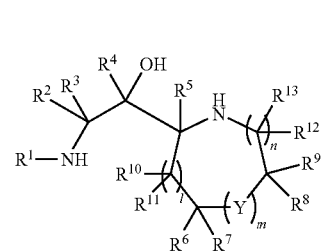

or a pharmaceutically acceptable salt or solvate thereof, wherein
R$^1$ is

X is —O—, —C(R$^{14}$)$_2$— or —N(R)—;
Z is —C(R$^{14}$)$_2$— or —N(R)—;
t is 0, 1, 2 or 3;
each R is independently selected from the group consisting of H, alkyl, cycloalkyl, cycloalkylalkyl, aryl, heteroaryl, heterocycloalkyl, arylalkyl, heteroarylalkyl, heterocycloalkylalkyl, alkenyl and alkynyl;
R$^2$ is H, alkyl, cycloalkyl, heterocycloalkyl, cycloalkylalkyl, heterocycloalkylalkyl, aryl, heteroaryl, arylalkyl, heteroarylalkyl, alkenyl or alkynyl;

$R^3$ is H or alkyl;

$R^4$ is H or alkyl;

$R^5$ is H, alkyl, cycloalkylalkyl, aryl or heteroaryl;

each $R^{14}$ is independently selected from the group consisting of H, alkyl, alkenyl, alkynyl, halo, —CN, haloalkyl, cycloalkyl, cycloalkylalkyl, aryl, heteroaryl, heterocycloalkyl, arylalkyl, heteroarylalkyl, heterocycloalkylalkyl, —$OR^{35}$, —$N(R^{24})(R^{25})$ and —$SR^{35}$;

$R^{41}$ is alkyl, cycloalkyl, —$SO_2$(alkyl), —C(O)-alkyl, —C(O)-cycloalkyl or -alkyl-NH—C(O)CH$_3$;

and wherein l, n, m, Y, and $R^6$, $R^7$, $R^8$, $R^9$, $R^{10}$, $R^{11}$, $R^{12}$ and $R^{13}$ are as defined in the following groups (A) to (C):

(A) when l is 0-3; n is 0-3; m is 0 or m is 1 and Y is —C($R^{30}$)($R^{31}$)—; and the sum of l and n is 0-3:

(i) $R^6$, $R^7$, $R^8$, $R^9$, $R^{10}$ and $R^{11}$ are independently selected from the group consisting of H, alkyl, cycloalkyl, cycloalkylalkyl, aryl, heteroaryl, heterocycloalkyl, arylalkyl, heteroarylalkyl, heterocycloalkylalkyl, alkenyl, alkynyl, halo, —$NO_2$, —CN, —$N(R^{15})(R^{16})$, —$OR^{17}$, —$SR^{17}$, —C(O)$R^{18}$, —$N(R^{15})$—C(O)$R^{17}$, —C(O)O$R^{17}$, —C(O)N($R^{15}$)($R^{16}$), —O—C(O)$R^{17}$ and —S(O)$_{1-2}R^{18}$; and $R^{12}$ and $R^{13}$ are independently selected from the group consisting of H, alkyl, cycloalkyl, cycloalkylalkyl, aryl, heteroaryl, heterocycloalkyl, arylalkyl, heteroarylalkyl, heterocycloalkylalkyl, alkenyl, alkynyl, —C(O)$R^{18}$ and —C(O)O$R^{17}$;

or (ii) $R^7$ and $R^9$, together with the ring carbons to which they are attached, form a fused cycloalkyl or fused heterocycloalkyl group and $R^6$, $R^8$, $R^{10}$, $R^{11}$, $R^{12}$ and $R^{13}$ are as defined in (A)(i); or $R^{10}$ and $R^{11}$, together with the ring carbon to which they are attached, form —C(O)—; or $R^{12}$ and $R^{13}$, together with the ring carbon to which they are attached, form —C(O)—;

or (iii) $R^6$ and $R^7$, together with the ring carbon to which they are attached, form —C(=O)—, and $R^8$, $R^9$, $R^{10}$, $R^{11}$, $R^{12}$ and $R^{13}$ are as defined in (A)(i);

or (iv) $R^8$ and $R^9$, together with the ring carbon to which they are attached, form —C(=O)—, and $R^6$, $R^7$, $R^{10}$, $R^{11}$, $R^{12}$ and $R^{13}$ are as defined in (A)(i);

(B) when l is 1; n is 0-2; and m is 0:

$R^6$ and $R^8$, together with the ring carbons to which they are attached, form a fused aryl group or a fused heteroaryl group, $R^7$ and $R^9$ form a bond, and $R^{10}$, $R^{11}$, $R^{12}$ and $R^{13}$ are as defined in (A)(i);

(C) when l is 0-3; n is 0-3; m is 1 and Y is —O—, —$NR^{19}$—, —S—, —SO— or —$SO_2$—; and the sum of l and n is 0-3:
$R^6$, $R^7$, $R^8$, $R^9$, $R^{12}$ and $R^{13}$ are independently selected from the group consisting of H, alkyl, cycloalkyl, cycloalkylalkyl, aryl, heteroaryl, heterocycloalkyl, arylalkyl, heteroarylalkyl, heterocycloalkylalkyl, alkenyl, alkynyl, —C(O)N($R^{15}$)($R^{16}$), —C(O)$R^{18}$, —C(O)O$R^{17}$ and —O—C(O)$R^{17}$; and $R^{10}$ and $R^{11}$ are as defined in (A)(i), or $R^{10}$ and $R^{11}$, together with the ring carbon to which they are attached, form —C(O)—; or $R^{12}$ and $R^{13}$, together with the ring carbon to which they are attached, form —C(O)—; or when Y is —O— or —$NR^{19}$—, $R^6$ and $R^7$, together with the ring carbon to which they are attached, form —C(O)—; or when Y is —O— or —$NR^{19}$—, $R^8$ and $R^9$, together with the ring carbon to which they are attached, form —C(O)—;

wherein $R^{15}$ is H or alkyl;

$R^{16}$ is H, alkyl, cycloalkyl, cycloalkylalkyl, aryl, heteroaryl, heterocycloalkyl, arylalkyl, heteroarylalkyl, heterocycloalkylalkyl, alkenyl or alkynyl;

or $R^{15}$ and $R^{16}$, together with the nitrogen to which they are attached, form a heterocycloalkyl ring;

$R^{17}$ is H, alkyl, cycloalkyl, aryl, heteroaryl, cycloalkylalkyl, arylalkyl, heteroarylalkyl, heterocycloalkyl, heterocycloalkylalkyl, alkenyl or alkynyl;

$R^{18}$ is H, alkyl, cycloalkyl, aryl, heteroaryl, cycloalkylalkyl, arylalkyl, heteroarylalkyl, heterocycloalkyl, heterocycloalkylalkyl, alkenyl, alkynyl or —$N(R^{24})(R^{25})$;

$R^{19}$ is H, alkyl, cycloalkyl, cycloalkylalkyl, aryl, heteroaryl, heterocycloalkyl, arylalkyl, heteroarylalkyl, heterocycloalkylalkyl, —COR$^{18}$, —C(O)OR$^{40}$, —SOR$^{18}$, —SO$_2$R$^{18}$ or —CN;

$R^{24}$ and $R^{25}$ are independently selected from the group consisting of H, alkyl, cycloalkyl, cycloalkylalkyl, aryl, heteroaryl, heterocycloalkyl, arylalkyl, heteroarylalkyl, heterocycloalkylalkyl, alkenyl and alkynyl;

or $R^{24}$ and $R^{25}$ together with the nitrogen to which they are attached, form a 3-7 membered heterocycloalkyl ring;

$R^{30}$ is H, alkyl, cycloalkyl, cycloalkylalkyl, aryl, heteroaryl, heterocycloalkyl, arylalkyl, heteroarylalkyl, heterocycloalkylalkyl, alkenyl, alkynyl, halo, —$NO_2$, —CN, —N($R^{15}$)($R^{16}$), —$OR^{17}$, —$SR^{17}$, —C(O)$R^{18}$, —N($R^{15}$)—C(O)$R^{17}$, —C(O)O$R^{17}$, —C(O)N($R^{15}$)($R^{16}$), —O—C(O)$R^{17}$ or —S(O)$_{1-2}R^{18}$;

$R^{31}$ is H or alkyl;

and wherein each of the alkyl, cycloalkyl, cycloalkylalkyl, heterocycloalkyl, heterocycloalkylalkyl, aryl, arylalkyl, heteroaryl, heteroarylalkyl, alkenyl and alkynyl groups in R, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{24}$, $R^{25}$ and $R^{30}$ are independently unsubstituted or substituted by 1 to 5 $R^{32}$ groups independently selected from the group consisting of halo, alkyl, cycloalkyl, cycloalkylalkyl, heterocycloalkyl, heterocycloalkylalkyl, aryl, arylalkyl, heteroaryl, heteroarylalkyl, —$NO_2$, —CN, haloalkyl, haloalkoxy, —N($R^{33}$)($R^{34}$), —NH(cycloalkyl), acyloxy, —$OR^{35}$, —$SR^{35}$, —C(O)$R^{36}$, —C(O)O$R^{35}$, —PO($OR^{35}$)$_2$, —$NR^{35}$C(O)$R^{36}$, —$NR^{35}$C(O)O$R^{39}$, —$NR^{35}$S(O)$_{0-2}R^{39}$, and —S(O)$_{0-2}R^{39}$; or two $R^{32}$ groups on the same ring carbon atom in cycloalkyl, cycloalkylalkyl, heterocycloalkyl or heterocycloalkylalkyl together form =O;

$R^{33}$ and $R^{34}$ are independently selected from the group consisting of H and alkyl;

$R^{35}$ is H, alkyl, cycloalkyl, aryl, heteroaryl, cycloalkylalkyl, arylalkyl, heteroarylalkyl, heterocycloalkyl, heterocycloalkylalkyl, alkenyl or alkynyl;

$R^{36}$ is H, alkyl, cycloalkyl, aryl, heteroaryl, cycloalkylalkyl, arylalkyl, heteroarylalkyl, heterocycloalkyl, heterocycloalkylalkyl, alkenyl, alkynyl or —N($R^{37}$)($R^{38}$);

$R^{37}$ and $R^{38}$ are independently selected from the group consisting of H, alkyl, cycloalkyl, cycloalkylalkyl, aryl, heteroaryl, heterocycloalkyl, arylalkyl, heteroarylalkyl, heterocycloalkylalkyl, alkenyl and alkynyl;

or $R^{37}$ and $R^{38}$ together with nitrogen to which they are attached, form a 3-7 membered heterocycloalkyl ring;

$R^{39}$ is alkyl, aryl, heteroaryl, arylalkyl, heteroarylalkyl, heterocycloalkyl, heterocycloalkylalkyl, alkenyl or alkynyl; and $R^{40}$ is alkyl, cycloalkyl, aryl, heteroaryl, cycloalkylalkyl, arylalkyl, heteroarylalkyl, heterocycloalkyl, heterocycloalkylalkyl, alkenyl or alkynyl.

In another aspect, the invention relates to a pharmaceutical composition comprising at least one compound of formula I and a pharmaceutically acceptable carrier.

In another aspect, the invention comprises the method of inhibiting BACE-1 comprising administering at least one compound of formula I to a patient in need of such treatment. Also claimed is the method of inhibiting the formation, or formation and deposition, of β-amyloid plaques in, on or around neurological tissue (e.g., the brain) comprising administering at least one compound of formula I to a patient in need of such treatment.

More specifically, the invention comprises the method of treating a cognitive or neurodegenerative disease comprising administering at least one compound of formula I to a patient in need of such treatment. In particular, the invention comprises the method of treating a Alzheimer's disease comprising administering at least one compound of formula I to a patient in need of such treatment.

In another aspect, the invention comprises the method of treating a cognitive or neurodegenerative disease comprising administering to a patient I need of such treatment a combination of at least one compound of formula I and at least one compound selected from the group consisting of β-secretase inhibitors other than those of formula I, HMG-CoA reductase inhibitors, gamma-secretase inhibitors, non-steroidal anti-inflammatory agents, N-methyl-D-aspartate receptor antagonists, cholinesterase inhibitors and anti-amyloid antibodies.

In a final aspect, the invention relates to a kit comprising in separate containers in a single package pharmaceutical compositions for use in combination, in which one container comprises a compound of formula I in a pharmaceutically acceptable carrier and a second container comprises a β-secretase inhibitors other than those of formula I, an HMG-CoA reductase inhibitor, a gamma-secretase inhibitor, a non-steroidal anti-inflammatory agent, an N-methyl-D-aspartate receptor antagonist, a cholinesterase inhibitor or an anti-amyloid antibody in a pharmaceutically acceptable carrier, the combined quantities being an effective amount to treat a cognitive disease or neurodegenerative disease such as Alzheimer's disease.

DETAILED DESCRIPTION

Referring to formula I, above, preferred compounds of the invention are those wherein $R^3$, $R^4$ and $R^5$ are hydrogen and $R^2$ is arylalkyl, alkyl or cycloalkylalkyl; more preferred are compounds wherein $R^2$ is optionally substituted benzyl, especially di-fluorobenzyl.

The $R^1$ portion of the compounds of formula I is preferably selected from

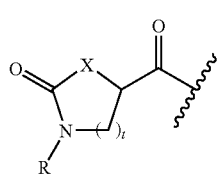
(1)

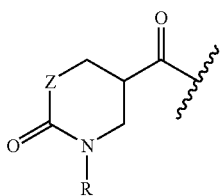
(2)

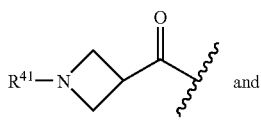
(3)

and

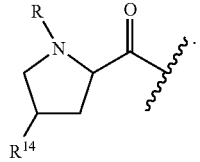
(4)

$R^1$ is more preferably (1),

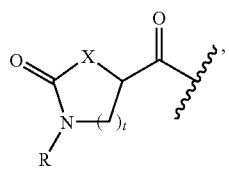

with compounds wherein t is 1 and X is —$C(R^{14})_2$— or —N(R)— being especially preferred.

Additional preferred embodiments of $R^1$ are as follows:

(1a):

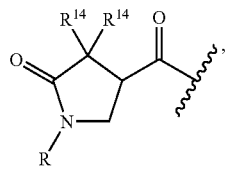

wherein R is preferably alkyl, optionally substituted arylalkyl, alkenyl, cycloalkylalkyl, alkoxyalkyl, hydroxyalkyl, aminoalkyl, or heteroarylalkyl, and $R^{14}$ is preferably hydrogen, alkyl, alkenyl, cycloalkyl or benzyl. When R is arylalkyl in structure (1a), it is preferably optionally substituted benzyl or optionally substituted phenylethyl, wherein the optional substituents are 1 or 2 $R^{32}$ groups independently selected from halo, alkyl, alkoxy and haloalkyl. Also, when R is heteroarylalkyl in structure (1a), the heteroaryl portion is preferably selected from pyridyl, furanyl, thienyl or thiazolyl, and the alkyl portion is preferably methyl. Especially preferred R groups in structure (1a) are alkyl, alkoxyalkyl and cycloalkylalkyl; especially preferred $R^{14}$ groups in structure (1a) are hydrogen and alkyl, particularly wherein one $R^{14}$ is hydrogen and the other is hydrogen or alkyl.

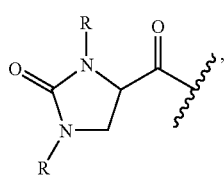
(1b)

wherein preferably each R is independently selected from the group consisting of hydrogen, alkyl, alkoxyalkyl, cycloalkylalkyl and benzyl.

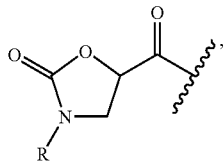

wherein preferably R is hydrogen, alkyl, alkoxyalkyl, cycloalkylalkyl or benzyl.

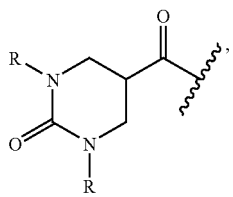

wherein each R is preferably independently selected from hydrogen, alkyl, alkoxyalkyl, cycloalkylalkyl and benzyl.

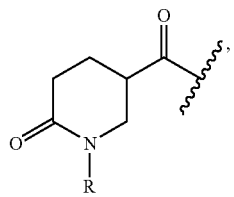

wherein preferably R is hydrogen, alkyl, alkoxyalkyl, cycloalkylalkyl or benzyl.

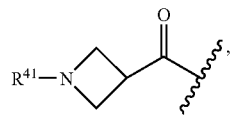

wherein $R^{41}$ is —C(O)-alkyl, —C(O)-cycloalkyl or —SO$_2$-alkyl.

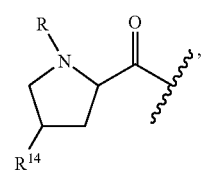

wherein R is preferably hydrogen, alkyl, alkoxyalkyl, cycloalkylalkyl or benzyl and $R^{14}$ is preferably alkoxy.

When $R^1$ is

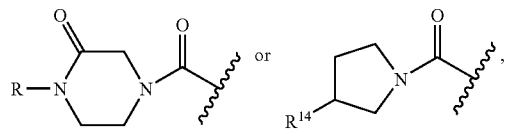

R is preferably alkyl, alkoxyalkyl, cycloalkylalkyl or benzyl and $R^{14}$ is preferably alkoxy.

Preferred $R^{32}$ substituents are selected from the group consisting of halo, alkyl, OH, alkoxy, alkoxyalkyl, alkoxyalkoxy, haloalkyl, haloalkoxy, CN, cycloalkyl, cycloalkoxy, cycloalkylalkyl, cycloalkylalkoxy, phenyl and benzyl. Also preferred are compounds wherein two $R^{32}$ substituents on the same ring carbon in a cycloalkyl, cycloalkylalkyl, heterocycloalkyl or heterocycloalkylalkyl group form =O.

The following are additional preferred embodiments of the invention:

1) compounds of formula I wherein $R^1$ to $R^5$ are as defined above in the summary of the invention and $R^6$ to $R^{13}$, l, m, n, and Y are as defined in (A);
2) compounds of formula I wherein $R^1$ to $R^5$ are the preferred definitions defined above and $R^6$ to $R^{13}$, l, m, n, and Y are as defined in (A);
3) compounds of formula I wherein $R^1$ to $R^5$ are as defined above in the summary of the invention and $R^6$ to $R^{13}$, l, m, n, and Y are as defined in (B);
4) compounds of formula I wherein $R^1$ to $R^5$ are the preferred definitions defined above and $R^6$ to $R^{13}$, l, m, n, and Y are as defined in (B);
5) compounds of formula I wherein $R^1$ to $R^5$ are as defined above in the summary of the invention and $R^6$ to $R^{13}$, l, m, n, and Y are as defined in (C);
6) compounds of formula I wherein $R^1$ to $R^5$ are the preferred definitions defined above and $R^6$ to $R^{13}$, l, m, n, and Y are as defined in (C).

In another embodiment, preferred are compounds of formula I, definition (A), wherein m is zero; the sum of l and n is 1 or 2; and $R^6$, $R^7$, $R^8$, $R^9$, $R^{10}$, $R^{11}$, $R^{12}$ and $R^{13}$ are each hydrogen; or wherein $R^6$, $R^7$, $R^8$, $R^9$, $R^{10}$, $R^{11}$ and $R^{13}$ are each hydrogen and $R^{12}$ is methyl; or wherein $R^6$, $R^7$, $R^8$, $R^9$, $R^{10}$ and $R^{11}$ are each hydrogen and $R^{12}$ and $R^{13}$ together are =O; or wherein $R^6$, $R^7$, $R^8$, $R^9$, $R^{12}$ and $R^{13}$ are each hydrogen and $R^{10}$ and $R^{11}$ are =O.

In another embodiment, preferred are compounds of formula I, definition (A), wherein m is zero; n is 1 and the sum of n and l is 1 or 2; $R^6$, $R^9$, $R^{10}$, $R^{11}$, $R^{12}$ and $R^{13}$ are each hydrogen; and $R^7$ and $R^8$ are as defined in the summary of the invention. More preferred are compounds of formula I, definition (A), wherein m is zero; n is 1 and the sum of n and l is 1 or 2; $R^6$, $R^9$, $R^{10}$, $R^{11}$, $R^{12}$ and $R^{13}$ are each hydrogen; and $R^7$ and $R^8$ are independently selected from the group consisting of H and —OR$^{17}$ wherein $R^{17}$ is H, alkyl, aryl, heteroaryl, arylalkyl or heteroarylalkyl; A preferred definition for $R^{17}$ is arylalkyl, especially benzyl, wherein the aryl portion is optionally substituted with one or two substituents independently selected from the group consisting of halo and alkoxy.

In another embodiment, preferred are compounds of formula I, definition (A), wherein m is zero; l is 1; n is 1 or 2; $R^7$ and $R^9$ form a fused cycloalkyl group; and $R^6$, $R^8$, $R^{10}$, $R^{11}$, $R^{12}$ and $R^{13}$ are each hydrogen. Preferably, $R^7$, $R^9$ and the carbons to which they are attached form a cyclopropyl ring.

In another embodiment, preferred are compounds of formula I, definition (A), wherein m is 1; Y is —C(R$^{30}$)(R$^{31}$)—;

l is 0; n is 1; $R^6$, $R^7$, $R^8$, $R^9$, $R^{12}$ and $R^{13}$ are each hydrogen; and $R^{30}$ and $R^{31}$ are as defined in the summary of the invention.

In another embodiment, preferred are compounds of formula I, definition (B), wherein m is zero; l is 1 and n is 1 or 2; $R^6$ and $R^8$ form a fused aryl group; $R^7$ and $R^9$ form a bond; and $R^{10}$, $R^{11}$, $R^{12}$ and $R^{13}$ are each hydrogen.

In another embodiment, preferred are compounds of formula I, definition (C), wherein m is 1; l is 0-3 and n is 0-3, provided that the sum of l and n is 1-3; Y is —O—, —$NR^{19}$—, —S—, —SO— or —$SO_2$—, wherein $R^{19}$ is alkyl, arylalkyl or —$SO_2R^{18}$, with preferred arylalkyl groups being benzyl and fluorobenzyl and preferred $R^{18}$ groups being aryl and heteroaryl, especially phenyl, pyridyl, thienyl and imidazolyl; and $R^6$, $R^7$, $R^8$, $R^9$, $R^{10}$, $R^{11}$, $R^{12}$ and $R^{13}$ are each hydrogen, or $R^8$, $R^9$, $R^{10}$, $R^{11}$, $R^{12}$ and $R^{13}$ are each hydrogen and $R^6$ and $R^7$ together are =O, or $R^6$, $R^7$, $R^9$, $R^{10}$, $R^{11}$ and $R^{13}$ are each hydrogen and $R^8$ and $R^{12}$ are as defined in the summary of the invention. More preferably, Y is —$NR^{19}$— or —O—, with —$NR^{19}$— being most preferred. In an especially preferred embodiment, m is 1; Y is —$NR^{19}$—; l is 0; n is 1; $R^8$, $R^9$, $R^{12}$, and $R^{13}$ are H; and $R^6$ and $R^7$ together are =O. In another especially preferred embodiment, m is 1; Y is —$NR^{19}$—; l is 0; n is 0; $R^8$ and $R^9$ are H; and $R^6$ and $R^7$ together are =O.

Specific preferred embodiments of the cycloamino ring portion are:

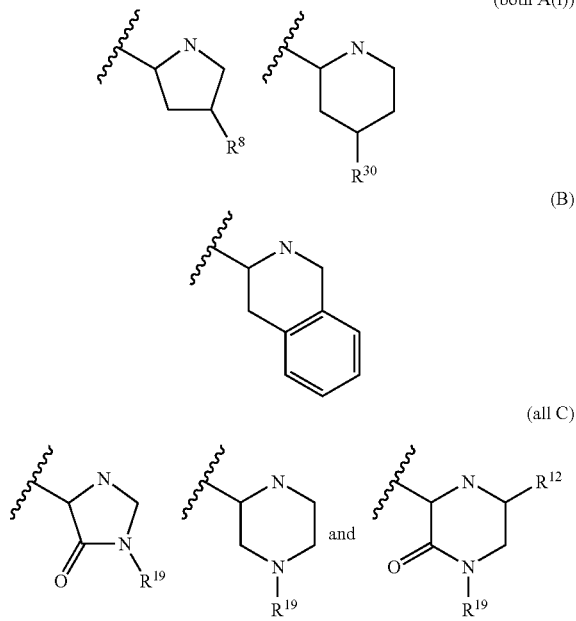

wherein:
$R^8$ is H, OH, alkoxy, phenoxy or optionally substituted benzyloxy;
$R^{12}$ is H or alkyl, preferably H;
$R^{19}$ is optionally substituted alkyl, —$SO_2R^{18}$, —$C(O)R^{18}$ or optionally substituted heteroarylalkyl, preferably alkyl, optionally substituted benzyl, benzoyl, (optionally substituted heteroaryl)alkyl, —$SO_2$alkyl, —$SO_2$(optionally substituted phenyl), —$SO_2$-naphthyl, (phenyl-alkenyl)-$SO_2$—, —$SO_2$— (optionally substituted benzyl), —$SO_2$— (optionally substituted heteroaryl), phenyl, —C(O)alkyl, —C(O)-(phenyl), —C(O)-heteroaryl, —C(O)N(alkyl)$_2$, —C(O)—O-benzyl, —$SO_2$— (optionally substituted heteroaryl), alkyl substituted by C(O)-heterocycloalkyl, alkyl-C(O)—N(alkyl)$_2$ and alkyl-C(O)—NH$_2$; and $R^{30}$ is —OC(O)-alkyl, optionally substituted phenyl, optionally substituted phenylalkyl, alkyl, alkoxy, cycloalkylalkyl, cycloalkylalkoxy, hydroxyalkoxy, dialkylaminoalkoxy, alkoxyalkyl, optionally substituted heterocycloalkyl, heterocycloalkylalkyl, heterocycloalkylalkoxy, or —C(O)—O-alkyl, more preferably alkoxy or alkoxyalkyl;

wherein the optional substituents on phenyl are $R^{32}$ substituents selected from the group consisting of halo, alkyl, —C(O)CH$_3$, phenyl, —COO-alkyl, alkoxy, haloalkyl, phenoxy, —CN, —$SO_2$-alkyl and —NHC(O)alkyl; wherein the optional substituents on benzyl are $R^{32}$ substituents selected from the group consisting of halo, alkyl, alkoxy, cyano and phenyl; and wherein heteroaryl is selected from the group consisting of pyridyl, pyrazolyl, oxazolyl, thiazolyl, pyrazinyl, thienyl and imidazolyl and the optional substituents on heteroaryl are selected from alkyl, halo, —COO-alkyl, heteroaryl and —NHC(O)alkyl.

More preferred specific embodiments of the cyclic amino portion are

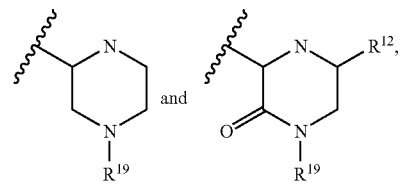

wherein the substituents are as defined in the paragraph immediately above, with the former being especially preferred.

The preferred stereochemistry of compounds of formula I is that shown in formula IA:

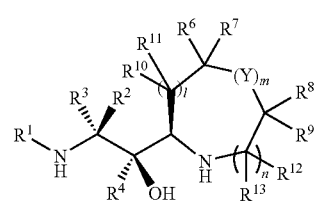

IA

As used above, and throughout the specification, the following terms, unless otherwise indicated, shall be understood to have the following meanings:

"Patient" includes both human and animals.

"Mammal" means humans and other mammalian animals.

"Alkyl" means an aliphatic hydrocarbon group which may be straight or branched and comprising 1 to 20 carbon atoms in the chain. Preferred alkyl groups contain about 1 to about 12 carbon atoms in the chain. More preferred alkyl groups contain about 1 to about 7 carbon atoms in the chain. Branched means that one or more lower alkyl groups such as methyl, ethyl or propyl, are attached to a linear alkyl chain. "Lower alkyl" means a group having about 1 to about 7 carbon atoms in the chain which may be straight or branched. Non-limiting examples of suitable alkyl groups include methyl, ethyl, n-propyl, isopropyl, n-butyl, t-butyl, n-pentyl, heptyl, nonyl and decyl. $R^{32}$-substituted alkyl groups include fluoromethyl, trifluoromethyl and cyclopropylmethyl.

"Alkenyl" means an aliphatic hydrocarbon group containing at least one carbon-carbon double bond and which may be straight or branched and comprising 2 to 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. Non-limiting examples of suitable alkenyl groups include ethenyl, propenyl, n-butenyl, 3-methylbut-2-enyl, n-pentenyl, octenyl and decenyl.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl, 3-methylbutynyl, n-pentynyl, and decynyl.

"Aryl" (sometimes abbreviated "ar") means an aromatic monocyclic or multicyclic ring system comprising about 6 to about 14 carbon atoms, preferably about 6 to about 10 carbon atoms. The aryl group can be optionally substituted with one or more $R^{32}$ substituents which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one to four of the ring atoms is an element other than carbon, for example nitrogen, oxygen or sulfur, alone or in combination. Preferred heteroaryls contain about 5 to about 6 ring atoms. The "heteroaryl" can be optionally substituted by one or more $R^{32}$ substituents which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, benzoxadiazolyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like.

"Arylalkyl" means an aryl-alkyl- group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Cycloalkyl" means a non-aromatic mono- or multicyclic ring system comprising 3 to 10 carbon atoms, preferably about 5 to about 10 carbon atoms. Preferred cycloalkyl rings contain about 5 to about 7 ring atoms. The cycloalkyl can be optionally substituted with one or more $R^{32}$ substituents which may be the same or different, and are as defined above.

Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalin, norbornyl, adamantyl and the like.

"Halo" means fluoro, chloro, bromo, or iodo groups. Preferred are fluoro, chloro or bromo, and more preferred are fluoro and chloro.

"Haloalkyl" means an alkyl as defined above wherein one or more hydrogen atoms on the alkyl is replaced by a halo group defined above.

Substituents on the rings defined above also include a cyclic ring of 3 to 7 ring atoms of which 1-2 may be a heteroatom, attached to an aryl, heteroaryl or heterocyclyl ring by simultaneously substituting two ring hydrogen atoms on said aryl, heteroaryl or heterocyclyl ring. Non-limiting examples include:

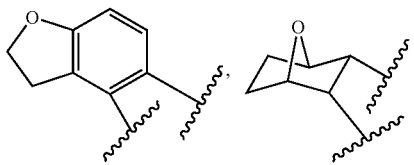

and the like.

"Heterocyclyl" (or heterocycloalkyl) means a non-aromatic saturated monocyclic or multicyclic ring system comprising about 3 to about 10 ring atoms, preferably about 5 to about 10 ring atoms, in which 1-3, preferably 1 or 2 of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. The heterocyclyl can be optionally substituted by one or more $R^{32}$ substituents which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like.

"Heteroarylalkyl" means a heteroaryl-alkyl- group in which the heteroaryl and alkyl are as previously described. Preferred heteroarylalkyls contain a lower alkyl group. Non-limiting examples of suitable heteroarylalkyl groups include pyridylmethyl, 2-(furan-3-yl)ethyl and quinolin-3-ylmethyl. The bond to the parent moiety is through the alkyl.

"Acyl" means an H—C(O)—, alkyl-C(O)—, alkenyl-C(O)—, alkynyl-C(O)— or cycloalkyl-C(O)— group in which the various groups are as previously described. The bond to the parent moiety is through the carbonyl. Preferred acyls contain a lower alkyl. Non-limiting examples of suitable acyl groups include formyl, acetyl, propanoyl, 2-methylpropanoyl, butanoyl and cyclohexanoyl.

"Alkoxy" means an alkyl-O— group in which the alkyl group is as previously described. Non-limiting examples of suitable alkoxy groups include methoxy, ethoxy, n-propoxy, isopropoxy, n-butoxy and heptoxy. The bond to the parent moiety is through the ether oxygen.

"Fused cycloalkyl" means that a cycloalkyl ring is fused to the cyclic amino portion of compounds of formula I, e.g., a compound having the structure

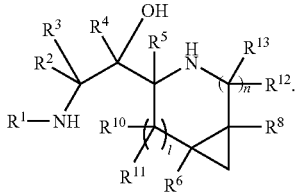

Similarly, "fused heterocycloalkyl" means that a heterocycloalkyl group is fused to the cyclic amino portion of compounds of formula I, e.g., a compound having the structure

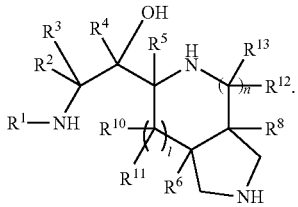

When "Y" is a heteroatom, $R^7$, $R^9$ and the carbons to which they are attached can form a fused ring wherein "Y" is the only heteroatom, or $R^7$, $R^9$ and the carbons to which they are attached can form a ring comprising one or two additional heteroatoms, e.g.,

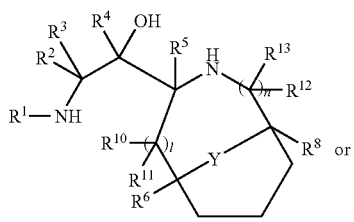

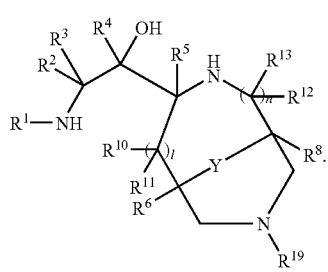

"Fused aryl" means that an aryl group is fused to the cyclic amino portion of compounds of formula I, e.g., a compound having the structure

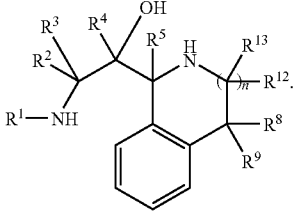

"Fused heteroaryl" means a similar structure, wherein, for example, the phenyl ring is replaced by pyridyl.

The cycloamino ring portion of the compounds of formula I, i.e., the portion of the compound having the structure

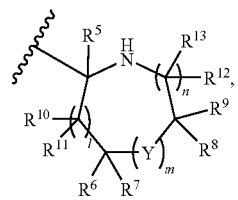

can have 1 or 2 oxo substituents, that is, where $R^{10}$ and $R^{11}$, or $R^6$ and $R^7$, or $R^8$ and $R^9$, or $R^{12}$ and $R^{13}$ form —C(O)— groups with the carbons to which they are attached, one or two such groups can be present on the ring as long the conditions in (C) are met (i.e., a —C(O)— group is not adjacent to $Y=S(O)_{0-2}$—). For example, $R^6$ and $R^7$, and $R^{12}$ and $R^{13}$ can each form —C(O)— groups with the carbons to which they are attached when m is 0 and $R^8$, $R^9$, $R^{10}$ and $R^{11}$ are hydrogen.

The term "optionally substituted" means optional substitution with the specified groups, radicals or moieties, in available position or positions.

With reference to the number of moieties (e.g., substituents, groups or rings) in a compound, unless otherwise defined, the phrases "one or more" and "at least one" mean that there can be as many moieties as chemically permitted, and the determination of the maximum number of such moieties is well within the knowledge of those skilled in the art. With respect to the compositions and methods comprising the use of "at least one compound of formula I," one to three compounds of formula I can be administered at the same time, preferably one.

As used herein, the term "composition" is intended to encompass a product comprising the specified ingredients in the specified amounts, as well as any product which results, directly or indirectly, from combination of the specified ingredients in the specified amounts.

The wavy line ∿∿∿as a bond generally indicates a mixture of, or either of, the possible isomers, e.g., containing (R)- and (S)-stereochemistry. For example,

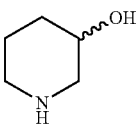

-continued

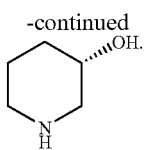

Lines drawn into the ring systems, such as, for example:

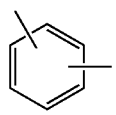

indicate that the indicated line (bond) may be attached to any of the substitutable ring carbon atoms.

As well known in the art, a bond drawn from a particular atom wherein no moiety is depicted at the terminal end of the bond indicates a methyl group bound through that bond to the atom, unless stated otherwise. For example:

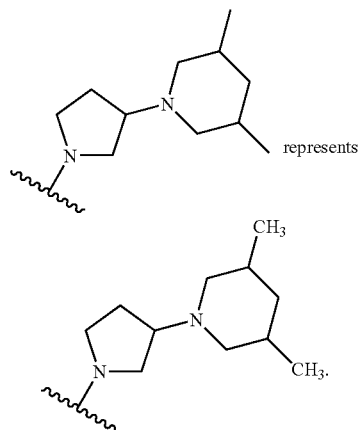

represents

It should also be noted that any heteroatom with unsatisfied valences in the text, schemes, examples, structural formulae, and any Tables herein is assumed to have the hydrogen atom or atoms to satisfy the valences.

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of formula I or a salt and/or solvate thereof. A discussion of prodrugs is provided in T. Higuchi and V. Stella, *Pro-drugs as Novel Delivery Systems* (1987) Volume 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

"Effective amount" or "therapeutically effective amount" is meant to describe an amount of compound or a composition of the present invention effective in inhibiting BACE-1 and thus producing the desired therapeutic effect in a suitable patient.

The compounds of formula I form salts which are also within the scope of this invention. Reference to a compound of formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of formula I contains both a basic moiety, such as, but not limited to a pyridine or imidazole, and an acidic moiety, such as, but not limited to a carboxylic acid, zwitterions ("inner salts") may be formed and are included within the term "salt (s)" as used herein. Pharmaceutically acceptable (i.e., non-toxic, physiologically acceptable) salts are preferred, although other salts are also useful. Salts of the compounds of the formula I may be formed, for example, by reacting a compound of formula I with an amount of acid or base, such as an equivalent amount, in a medium such as one in which the salt precipitates or in an aqueous medium followed by lyophilization. Acids (and bases) which are generally considered suitable for the formation of pharmaceutically useful salts from basic (or acidic) pharmaceutical compounds are discussed, for example, by S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; in *The Orange Book* (Food & Drug Administration, Washington, D.C. on their website); and P. Heinrich Stahl, Camille G. Wermuth (Eds.), *Handbook of Pharmaceutical Salts: Properties, Selection, and Use*, (2002) Int'l. Union of Pure and Applied Chemistry, pp. 330-331. These disclosures are incorporated herein by reference thereto.

Exemplary acid addition salts include acetates, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, methyl sulfates, 2-naphthalenesulfonates, nicotinates, nitrates, oxalates, pamoates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates,) undecanoates, and the like.

Exemplary basic salts include ammonium salts, alkali metal salts such as sodium, lithium, and potassium salts, alkaline earth metal salts such as calcium and magnesium salts, aluminum salts, zinc salts, salts with organic bases (for example, organic amines) such as benzathines, diethylamine, dicyclohexylamines, hydrabamines (formed with N,N-bis (dehydroabietyl)ethylenediamine), N-methyl-D-glucamines, N-methyl-D-glucamides, t-butyl amines, piperazine, phenylcyclohexylamine, choline, tromethamine, and salts with amino acids such as arginine, lysine and the like. Basic nitrogen-containing groups may be quaternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Compounds of formula I, and salts, solvates and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate" "prodrug" and the like, is intended to equally apply to the salt, solvate and prodrug of enantiomers, stereoisomers, rotamers, tautomers, racemates or prodrugs of the inventive compounds.

For the combination aspect, the use of any β-secretase inhibitor other than those of formula I is contemplated; β-secretase inhibitory activity can be determined by the procedures described below. Typical β-secretase inhibitors include, but are not limited to, those disclosed in WO 02/02505, WO 02/02506, WO 02/02512, WO 02/02518, WO 02/02520 and WO 02/088101.

Gamma-secretase inhibitors for use in the combination of this invention can be determined by procedures known in the art. Typical gamma-secretase inhibitors include, but are not limited to, those described in WO 03/013527, U.S. Pat. No. 6,683,091, WO 03/066592, U.S. Ser. No. 10/663,042, filed Sep. 16, 2003, WO 00/247671, WO 00/050391, WO 00/007995 and WO 03/018543.

HMG-CoA reductase inhibitors for use in combination with compounds of formula I include the "stains," e.g., atorvastatin, lovastatin, simvistatin, pravastatin, fluvastatin and rosuvastatin.

Cholinesterase inhibitors for us in the combination include acetyl- and/or butyrylcholinesterase inhibitors. Examples of cholinesterase inhibitors are tacrine, donepezil, rivastigmine, galantamine, pyridostigmine and neostigmine.

Non-steroidal anti-inflammatory agents for use in combination with compounds of formula I include ibuprofen, naproxen, diclofenac, diflunisal, etodolac, flurbiprofen, indomethacin, ketoprofen, ketorolac, nabumetone, oxaprozin, piroxicam, sulindac, tolmetin, celecoxib and rofecoxib. A suitable N-methyl-D-aspartate receptor antagonist is, for example, memantine. Anti amyloid antibodies are described, for example, in Hock et al, *Nature Medicine*, 8 (2002), p. 1270-1275.

Compounds of formula I can be made using procedures known in the art. The following reaction schemes show typical procedures, but those skilled in the art will recognize that other procedures can also be suitable. In the Schemes and in the Examples below, the following abbreviations are used:

methyl: Me; ethyl: Et; propyl: Pr; butyl: Bu; benzyl: Bn
high pressure liquid chromatography: HPLC
liquid chromatography mass spectroscopy: LCMS
thin layer chromatography: TLC
preparative thin layer chromatography: PTLC
room temperature: RT
hour: h
minute: min
retention time: $t_R$
1-hydroxybenzotriazole: HOBt
1-(3-dimethylaminopropyl)-3-ethylcarbodiimide methiodide: EDCl
1-(3-dimethylaminopropyl)-3-ethylcarbodiimide hydrochloride: EDC
benzotriazole-1-yl-oxy-trispyrrolidinophosphonium hexafluorophosphate:
    PyBOP
ethyl acetate: EtOAc
tetrahydrofuran: THF
N,N-dimethylformamide: DMF
n-butyllithium: n-BuLi
1-hydroxy-1-oxo-1,2-benzodioxol-3(1H)-one: IBX
triethylamine: $NEt_3$ or $Et_3N$
dibutylboron triflate: $Bu_2BOTf$
methanol: MeOH
diethyl ether: $Et_2O$
acetic acid: AcOH
diphenylphosphoryl azide: DPPA
isopropanol: iPrOH
benzyl alcohol: BnOH
1-hydroxy-7-azabenzotriazole: HOAt
O-(7-azabenzotriazol-1-yl)-N,N,N',N'-tetramethyluronium hexafluorophosphate:
    HATU
trifluoroacetic acid: TFA
tertiary butyloxycarbonyl: Boc
benzyloxycarbonyl: Cbz
dimethylsulfoxide: DMSO
diisopropylethylamine: DIEA
lithium diisopropylamide: LDA
tris-(2-aminoethyl)aminomethyl polystyrene (PS-trisamine)
methylisocyanate polystyrene (PS-NCO)

General Schemes:

In Scheme 1, a cyclic amine 2-carboxaldehyde derivative is added to an Evans acyl oxazolidinone bearing an appropriate $R^2$ group. Cleavage of the oxazolidinone product II and Curtius rearrangement of the resultant carboxylic acid III affords an oxazolidinone IV. Base hydrolysis of the oxazolidinone IV to give V and derivatization of the primary amine of V by, for example, acylation, affords an intermediate VIII. Removal of the cyclic amine protecting group gives the desired product.

Alternatively, VI is formed by protection of the hydroxyl group of III. Curtius rearrangement of VI and trapping of the intermediate isocyanate with benzyl alcohol affords VII which can be deprotected to give intermediate V.

In the schemes, the variable "$R^x$" is used in place of variables $R^6$-$R^{13}$ in order to simplify the structures. "PG" refers to an amine protecting group. Examples of suitable amine protecting groups are Boc and Cbz; Bn can also be used for secondary amines, and $(Bn)_2$ can also be used for primary amines (in which case, the PG-NH— portion of the structures shown in the schemes below would become $(PG)_2$-N—, i.e., $(Bn)_2$-N—).

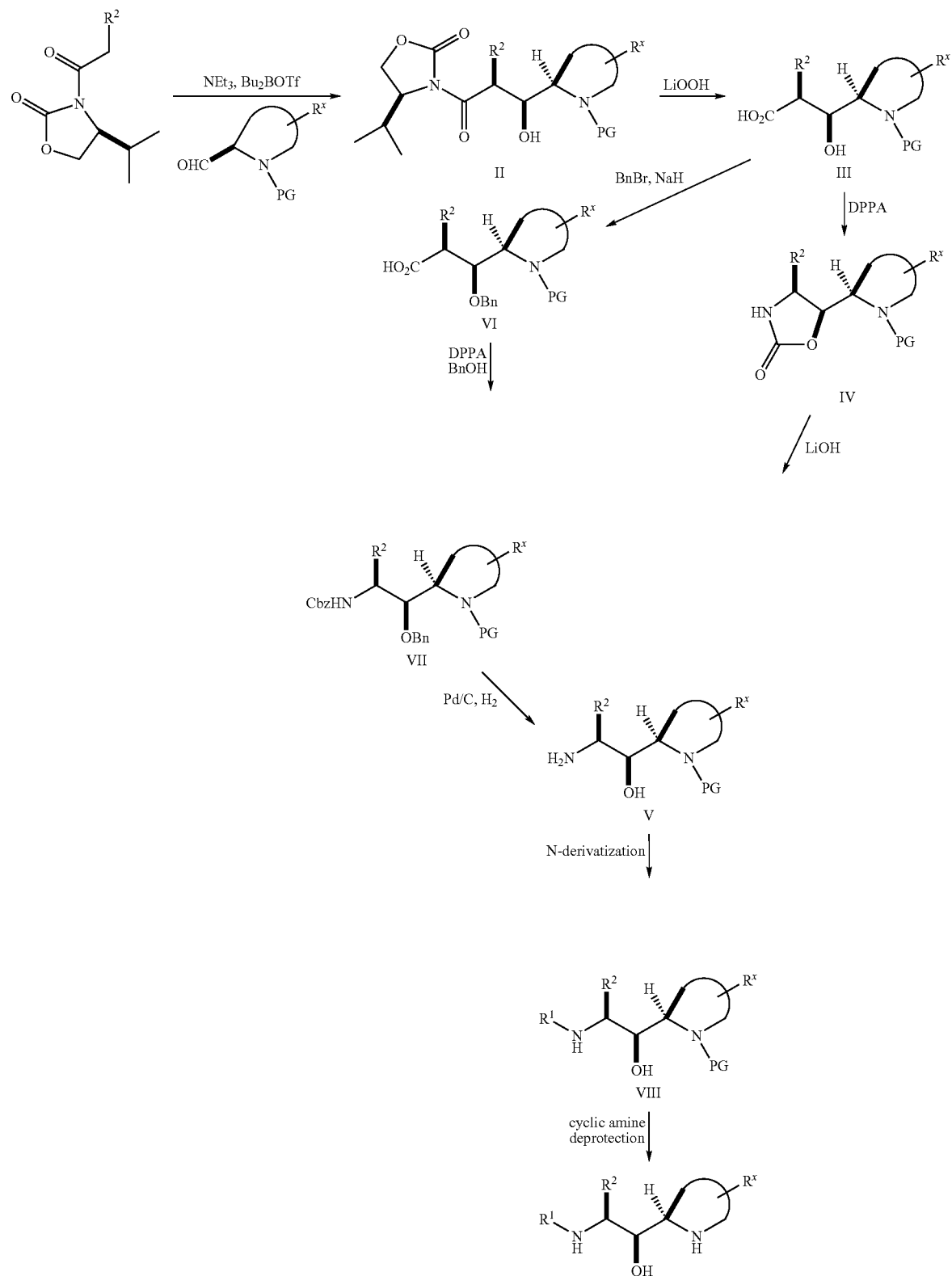

Scheme 2 shows another method of synthesis of the desired compounds, wherein the anion generated from a 3-oxo cyclic amine derivative is added to a protected α-amino aldehyde derivative to give an adduct IX. Deprotection of IX, followed by derivatization of the primary amine, followed by cyclic amine protecting group removal, affords the desired product.

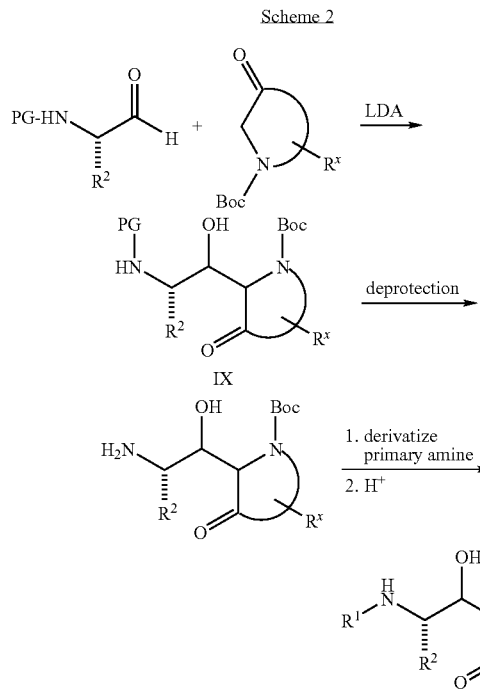

In Scheme 4, a 2-lithio derivative of 4-chloropyridine is added to a protected amino aldehyde to give the intermediate XIII. The chloro substituent of XIII can be displaced by an alkoxide ($R^{17X}$—OH, wherein $R^{17X}$ is as defined for $R^{17}$, but not H) to give an ether XIV. Deprotection and derivatization of the primary amine, followed by reduction of the pyridine ring gives the corresponding piperidine product.

In Scheme 3, a lithio derivative of a 2-halopyridine is added to a protected α-amino aldehyde derivative to give an adduct X. The protected primary amine of X is deprotected and the resultant amine is acylated to the desired derivative XI. Hydrogenation of the pyridine ring affords a piperidine derivative, the nitrogen of which can be protected for ease of purification to give XII. Deprotection of the cyclic amine XII gives the desired product.

In Scheme 5, lithiated XV is added to a protected N,N-dibenzyl aminoaldehyde to give a product XVI. Removal of the N,N-dibenzyl protecting group from XVI by hydrogenolysis followed by reduction of the piperazinone oxo group with borane-dimethylsulfide gives a piperazine product XVII. Derivatization of the primary amine of XVII and hydrogenolysis of the piperazine benzyl group gives intermediate XVIII. Derivatization of the piperazine nitrogen of XVIII followed by deprotection gives the piperazine product.

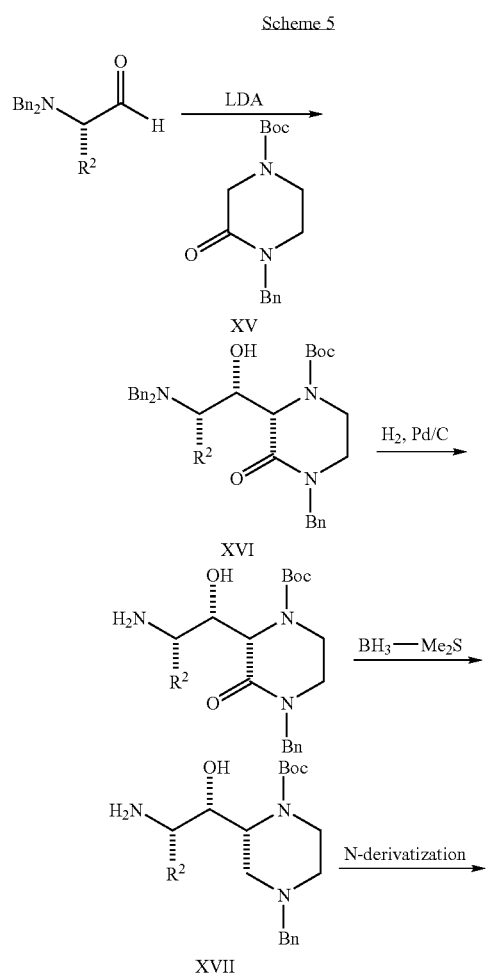

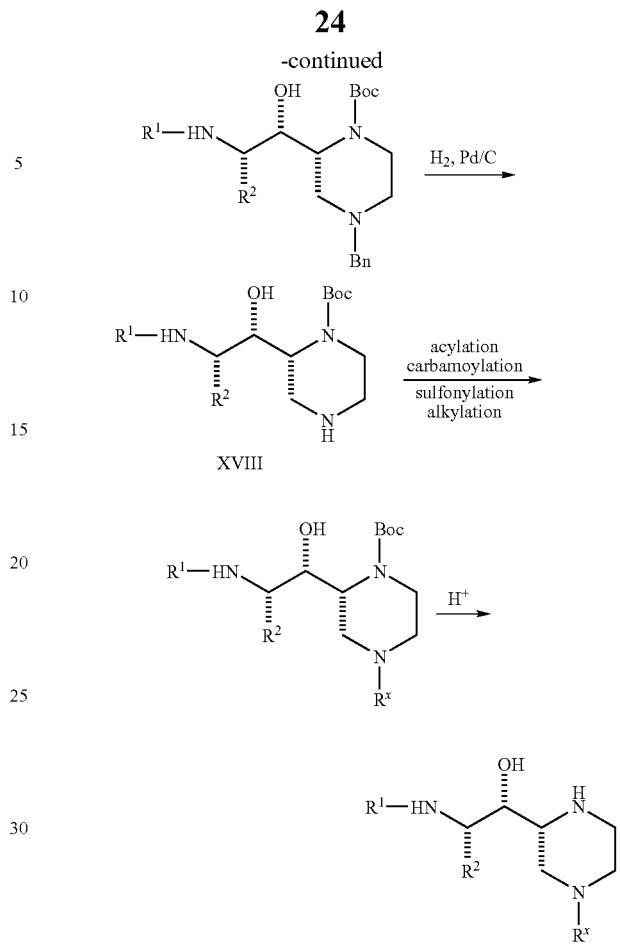

Scheme 6 is a variation of Scheme 5, wherein the oxo group of XVI is removed by reduction with borane-dimethyl sulfide followed by removal of the N-benzyl groups to give a diamine XIX. Introduction of $R^x$ by derivatization of the secondary amine of XIX to give XX, followed by introduction of $R^1$ and deprotection gives the products. Alternatively, the primary amine of XIX can be protected by imine formation to give XXI. Introduction of $R^x$ by derivatization of the secondary amine of XXI, followed by deprotection of the primary amine gives XXII. Intermediate XXII is derivatized by introduction of $R^1$ and deprotection to give the desired product.

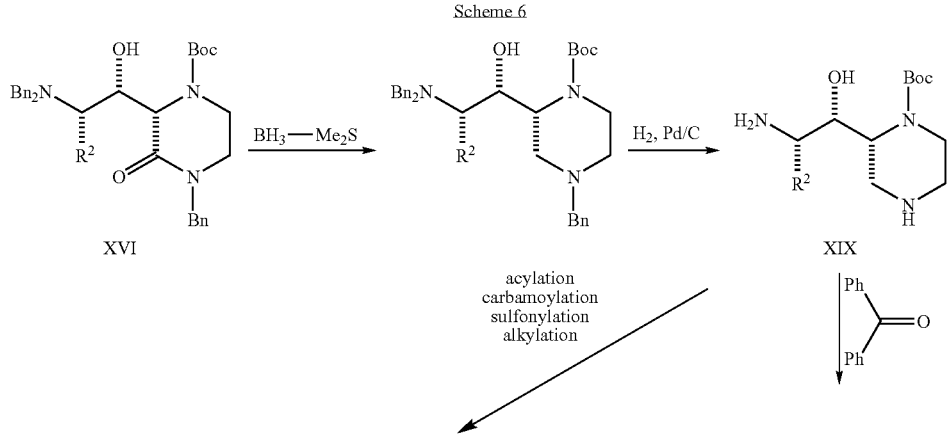

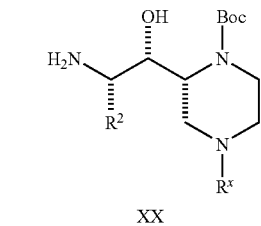

XX

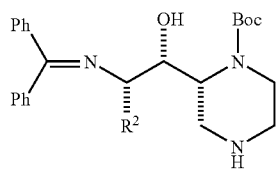

XXI

1. N-derivatization
2. H⁺

1. acylation
   carbamoylation
   sulfonylation
   or alkylation
2. NH₂OH

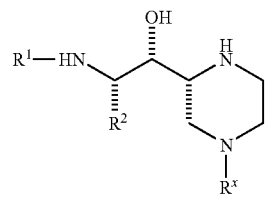

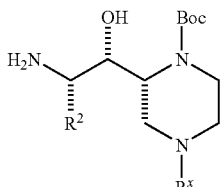

XXII

1. N-derivatization
2. H⁺

The conditions for the LCMS and RP-HPLC analyses in the preparations and examples below are as follows:

Conditions A: 5 minute gradient from 10%→95% CH₃CN/H₂O with 0.1% TFA, then 2 min isocratic at 95% CH₃CN/H₂O with 0.1% TFA, 1.0 ml/min flow rate on an analytical C18 reverse phase column.

Conditions B: gradient from 10%→95% CH₃CN/H₂O with 0.1% HCO₂H, 25 ml/min flow rate on a preparative C18 reverse phase column.

Conditions C: gradient from 5%→95% CH₃CN/H₂O with 0.1% HCO₂H, 20 ml/min flow rate on a a preparative C18 reverse phase column.

Preparation 1

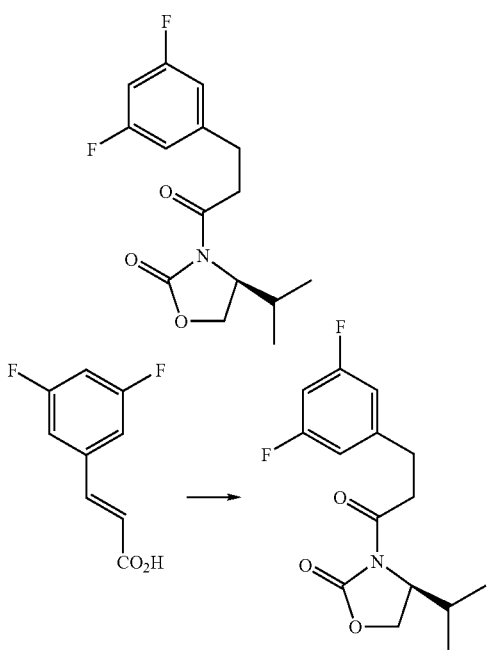

According to the literature (Kruse et al., *J. Med. Chem.* (1987), 30, 486-494), a solution of 3,5-difluorocinnamic acid (9.94 g, 53.9 mmol) in THF (100 ml) was hydrogenated over 10% Pd/C (1.50 g) at 50 psi of H₂ pressure for 5 h. The mixture was filtered and concentrated under reduced pressure to yield the 3-(3,5-difluoro-phenyl)propionic acid (10.9 g, 100%). Oxalyl chloride (13 ml, 150 mmol) was slowly added to a solution of the acid (10.9 g, 53.9 mmol) in THF (220 ml) at 23° C., followed by the addition of a catalytic amount of DMF (1 drop). After 90 min, the volatiles were removed under reduced pressure and the resulting residue was twice coevaporated with dry benzene to yield 3-(3,5-difluorophenyl)-propionyl chloride as a yellow oil (11.91 g, 100%). The acid chloride was used in the ensuing step without further purification. The acylation was carried out in analogy to the literature (Pettit et al. *Synthesis*, (1996), 719-725). A solution of (S)-(−)-4-isopropyl-2-oxazolidinone (6.46 g, 50 mmol) in THF (150 ml) was stirred under argon and cooled to −78° C. n-BuLi (2.45 M in hexanes, 20.8 ml, 50.96 mmol) was added dropwise, followed by a solution of the previously prepared 3-(3,5-difluorophenyl)-propionyl chloride in THF (8 ml). After warming the reaction to 23° C. over 15 h, the reaction was quenched with saturated aq. NH₄Cl (30 ml), followed by removal of the volatiles in vacuo. The slurry was extracted with CH₂Cl₂ (×2), and the combined organic layers washed with NaOH (×2) and brine, dried (Na₂SO₄) and concentrated in vacuo. Purification of the residue by chromatography over silica gel (15→30% EtOAc/hexanes) gave the product (14.27 g, 48 mmol, 96%). ¹H NMR (400 MHz, CDCl₃): δ=6.73 (m, 2 H), 6.59 (m, 1 H), 4.37 (m, 1 H), 4.17-4.25 (m, 2 H), 3.24 (m, 1 H), 3.16 (m, 1 H), 2.93 (m, 2 H), 2.30 (m, 1 H), 0.86 (d, 3 H, J=6.8 Hz), 0.80 (d, 3 H, J=6.8 Hz); LCMS (Conditions A): $t_R$=4.47 min: 595 (2M+H), 298 (M+H).

Preparation 2A

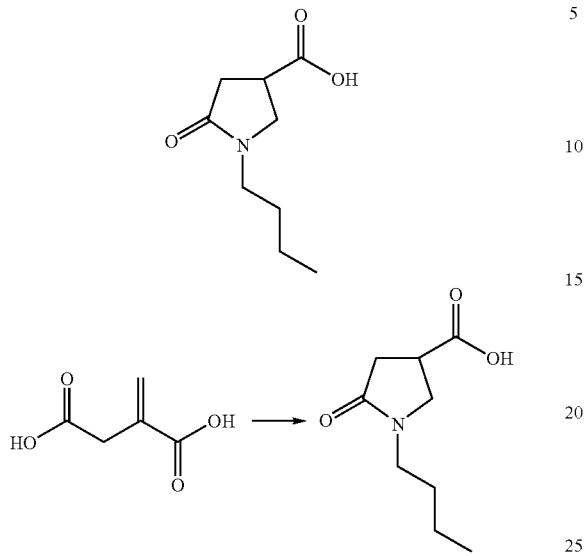

A mixture of itaconic acid (13.0 g, 100 mmol) and n-butylamine (7.31 g, 100 mmol) in toluene (100 ml) was heated in a sealed tube at 120° C. for 22 h. The mixture was cooled to RT and 1N NaOH (400 ml) was added. The aqueous layer was washed with $Et_2O$ (2×200 ml), acidified with conc. HCl (40 ml), and extracted with $Et_2O$ (3×200 ml). The combined $Et_2O$ layer was washed with brine, dried over $Na_2SO_4$, concentrated, and dried in vacuo to give the product (12.0 g, 65%). MS m/e 186 (M+H)$^+$.

Using an analogous procedure and the appropriate amine, the following acids were prepared in racemic form, unless otherwise indicated:

2B
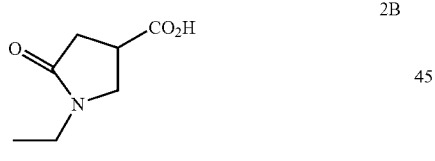

2C
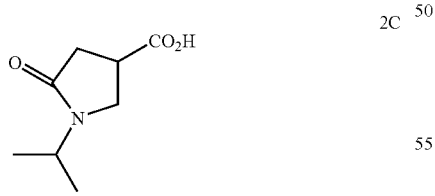

2D
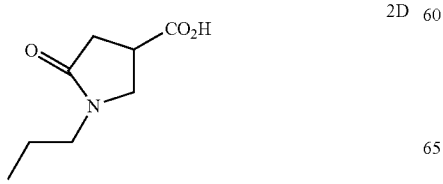

2E
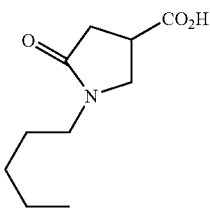

2F
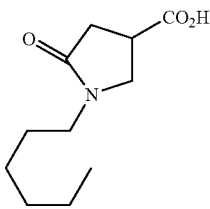

2G
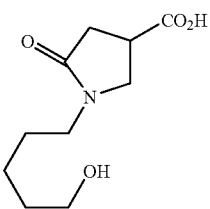

2H
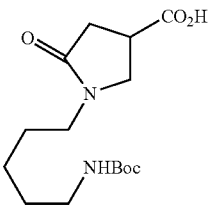

2I
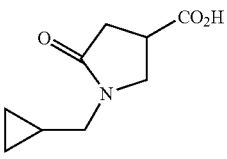

2J
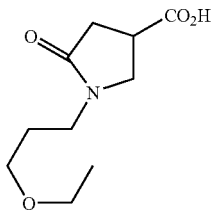

2K
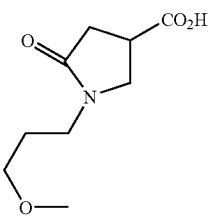

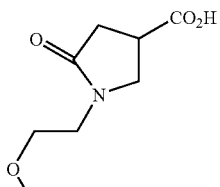 2L
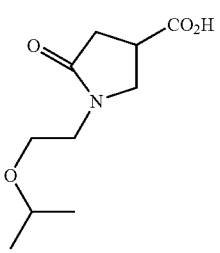 2M
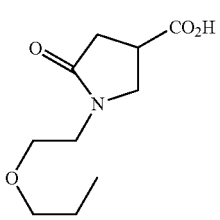 2N
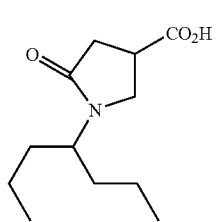 2O
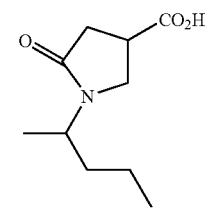 2P
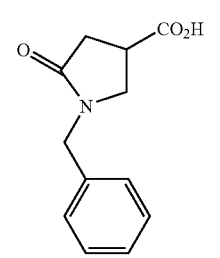 2Q
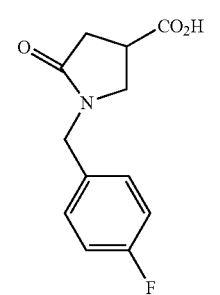 2R
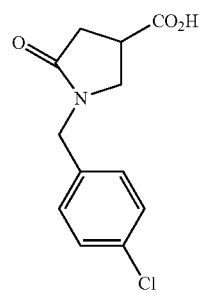 2S
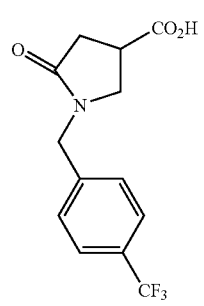 2T
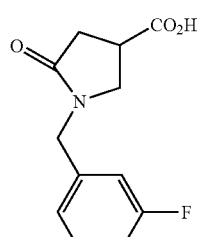 2U
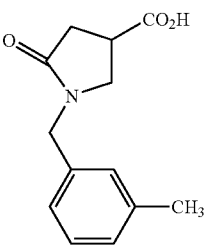 2V
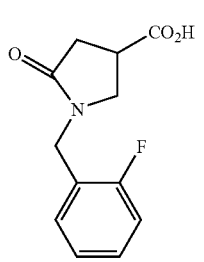 2W
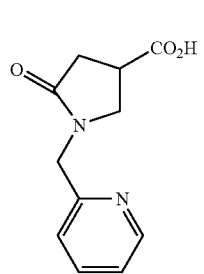 2X

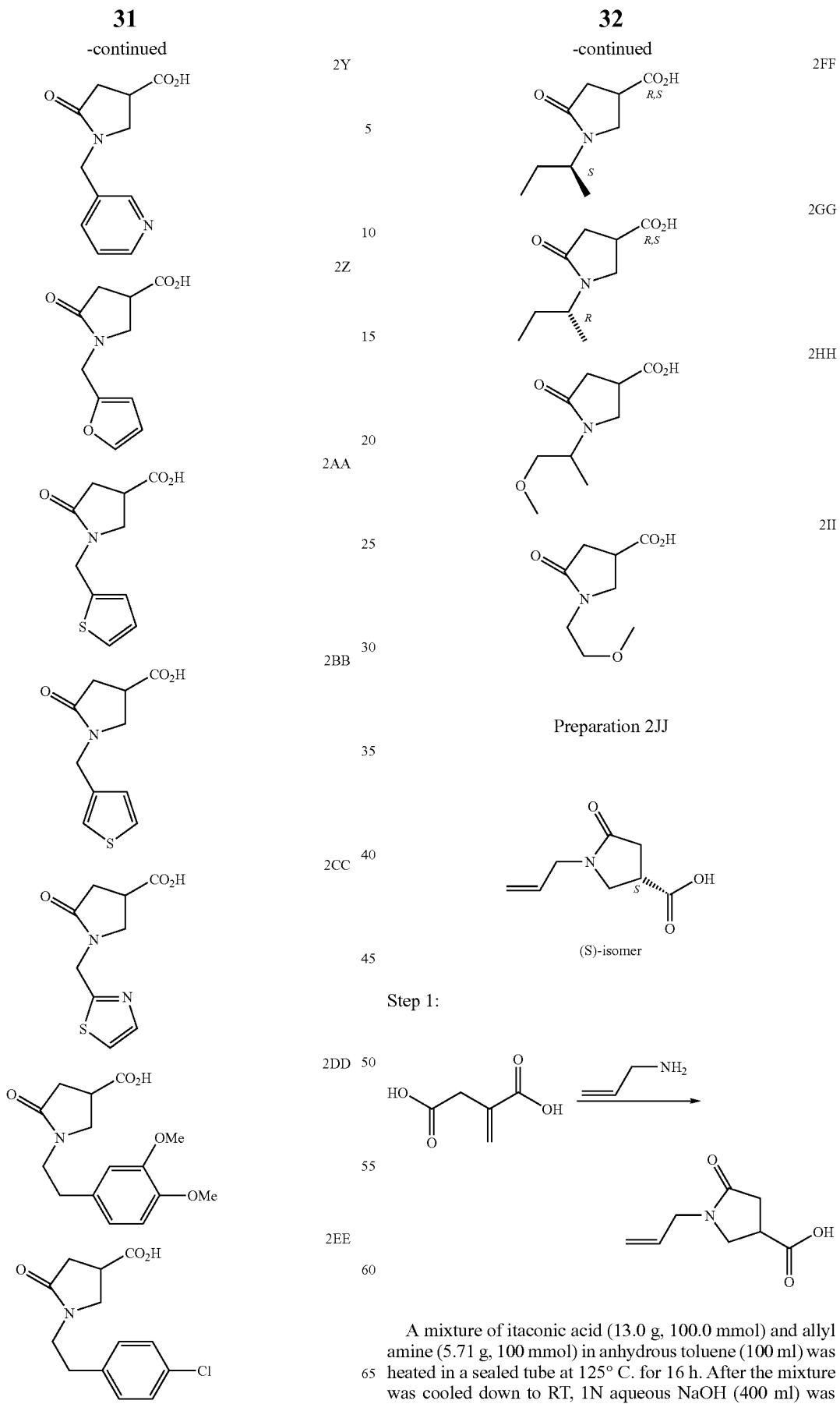
Preparation 2JJ
Step 1:
A mixture of itaconic acid (13.0 g, 100.0 mmol) and allyl amine (5.71 g, 100 mmol) in anhydrous toluene (100 ml) was heated in a sealed tube at 125° C. for 16 h. After the mixture was cooled down to RT, 1N aqueous NaOH (400 ml) was added and the aqueous layer was extracted with ether (2×200 ml). The aqueous layer was acidified with conc. HCl to pH 1 and extracted with ether (10×300 ml). The combined organic portion was concentrated and the residue was dissolved with CH$_2$Cl$_2$ (200 ml) and washed with brine. The organic layer was dried with MgSO$_4$, concentrated, and lyophilized to give a light yellow solid (9.60 g, 57%). MS m/e 170 (M+H)$^+$.

Step 2:

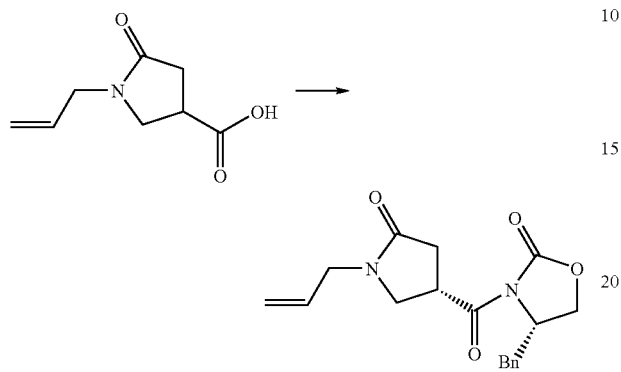

To a solution of the product of Step 1 (8.60 g, 50.9 mmol) and Et$_3$N (15.4 g, 153 mmol) in anhydrous THF (200 ml) at −45° C. was added pivaloyl chloride (6.45 g, 53.5 mmol). The mixture was stirred at −45° C. for 1 h and then added into a suspension of LiCl (4.75 g, 112 mmol) and (S)-4-benzyl-2-oxazolidinone (9.02 g, 50.9 mmol) in THF (100 ml). The resulting mixture was stirred at RT for 16 h and filtered. The filtrate was concentrated, dissolved in EtOAc (700 ml), and washed with 1N HCl (200 ml), sat'd NaHCO$_3$ (200 ml), and brine. The organic layer was dried (MgSO$_4$), concentrated, and purified by column chromatography (SiO$_2$, gradient 0-75% EtOAc/Hexanes) to give the product (7.20 g, 43%). MS m/e 329 (M+H)$^+$.

Step 3:

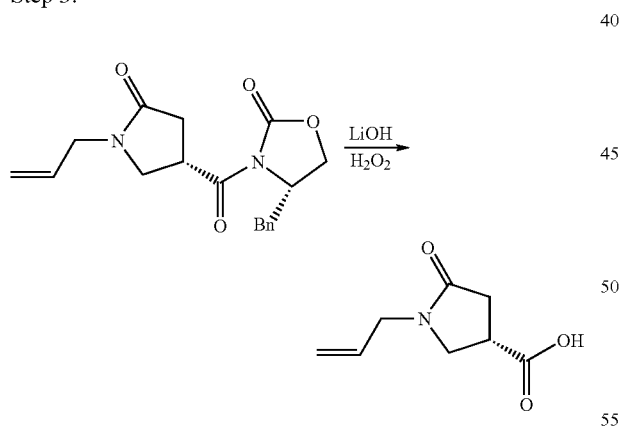

To a solution of the product of Step 2 (2.63 g, 8.01 mmol) in THF (30 ml) and water (8 ml) in an ice-water bath was added 30% H$_2$O$_2$ (4 ml) and LiOH (0.672 g, 16.0 mmol). The mixture was stirred at 0° C. for 7 h. 10% Aqueous sodium bisulfite (40 ml) was added and the mixture was stirred at RT for 16 h. The mixture was concentrated and the residue was partitioned between 1N NaOH (8 ml) and CH$_2$Cl$_2$ (2×100 ml). The aqueous layer was acidified to pH 2 at 0° C. and extracted with ether (5×100 ml). The combined organic portion was dried (MgSO$_4$) and concentrated to give the product (1.00 g, 74%). MS m/e 170 (M+H)$^+$.

Using the appropriate starting lactam and essentially the same procedure the following Preparations were obtained.

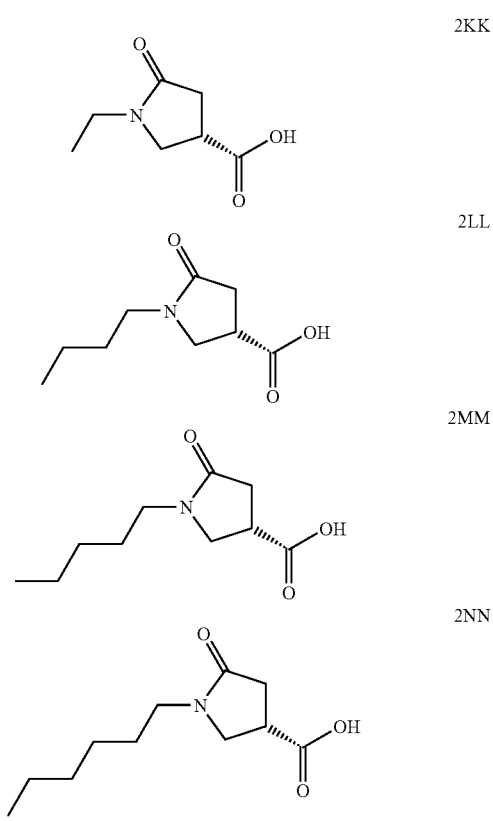

Preparation 3A

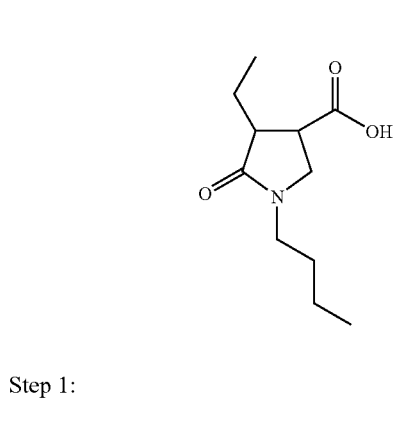

Step 1:

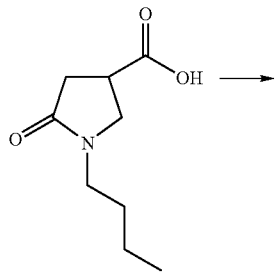

-continued

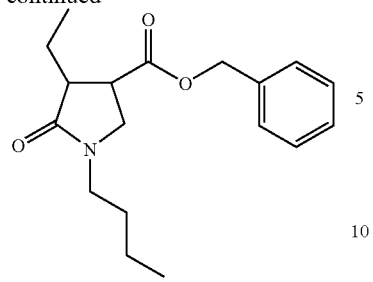

To an ice-cold solution of Preparation 2A (1.148 g, 6.20 mmol) in anhydrous THF (20 ml) was added 1.0M lithium bis(trimethylsilyl)amide in hexanes (13.0 ml). The mixture was stirred in ice-water bath for 30 min., at RT for 2 h, and then cooled in a dry ice-acetone bath. Iodoethane was added and the mixture was allowed to warm to RT slowly and stirred for 16 h. The mixture was diluted with EtOAc (45 ml) and washed with ice-cold water (60 ml). The aqueous layer was acidified with conc. HCl to pH=1-2 and extracted with EtOAc (2×60 ml). The combined organic layer was washed with brine (30 ml), dried (MgSO$_4$), and concentrated. The residue was taken up in CH$_2$Cl$_2$ (20 ml) and oxalyl chloride (0.53 ml, 6.0 mmol) was added along with 3 drops of DMF. The reaction mixture was stirred at RT for 16 h then cooled in an ice-water bath. To this reaction mixture was added Et$_3$N (1.7 ml, 12 mmol) and benzyl alcohol (0.875 g, 8.09 mmol). After stirring at RT for 24 h, the mixture was diluted with CH$_2$Cl$_2$ (50 ml) and washed with 5% citric acid (60 ml) and saturated NaHCO$_3$ solution (50 ml). The organic layer was dried (MgSO$_4$), concentrated, and purified by column chromatography (gradient hexanes to 1:4 EtOAc/hexanes) to give the product (0.608 g, 32%). MS m/e 304 (M+H)$^+$.

Step 2:

A mixture of the product of Step 1 (0.608 g) and 10% Pd/C (0.06 g) in EtOH (20 ml) was stirred under H$_2$ (1 atm) for 16 h. The mixture was filtered through a pad of Celite and concentrated to give the product (0.441 g, 100%). MS m/e 214 (M+H)$^+$.

Using an appropriate alkyl halide and an analogous procedure, the following acids were prepared:

3B

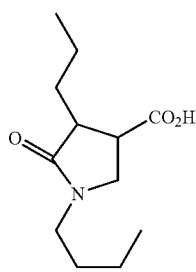

3C

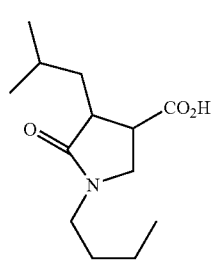

-continued

3D

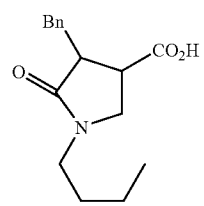

3E

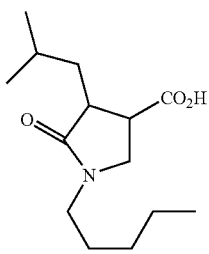

3F

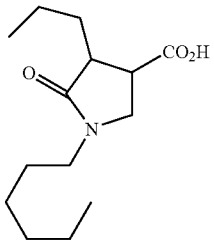

3G

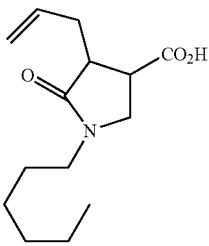

Preparations 3H-3M

Carboxylic acids 3H-3N were prepared in analogy to the published procedure (Baltaief et al., Tetrahedron, 1999, 55, 3949).

3H

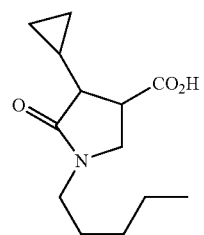

-continued

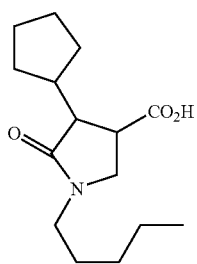

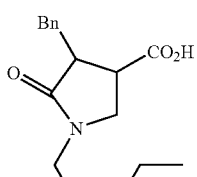

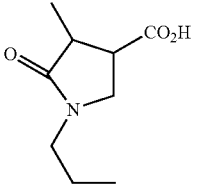

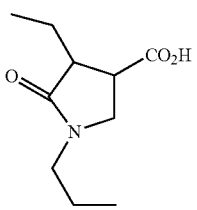

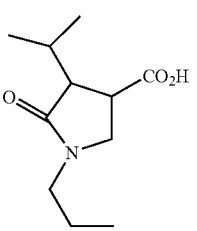

Preparation 4

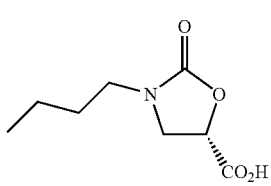

Step 1:

3I

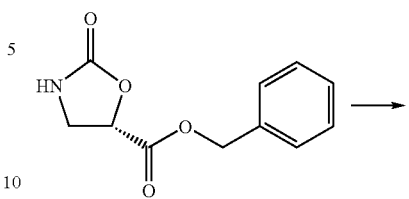

3J

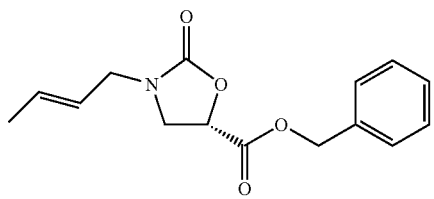

A mixture of benzyl (S)-2-oxazolidinone-5-carboxylate (750 mg, 3.39 mmol; prepared according to K. Danielmeier et al, *Tetrahedron: Asymmetry*, (1995), 6, 1181-1190), crotyl bromide (2.02 g, 15.0 mmol), and anhydrous $K_2CO_3$ (1.88 g, 13.6 mmol) in anhydrous acetone (20 ml) was stirred at RT for 24 h. The mixture was filtered and concentrated. The residue was dissolved in $CH_2Cl_2$ (100 ml), washed with water and brine, dried ($MgSO_4$), concentrated, and purified by column chromatography ($CH_2Cl_2$) to give the title compound (480 mg, 51%). MS m/e 276 $(M+H)^+$.

Step 2:

3L

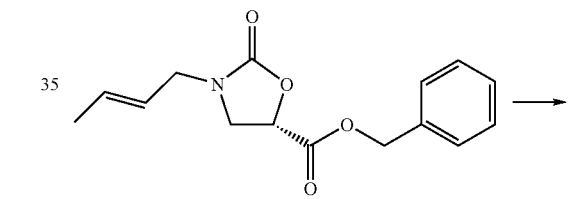

3M

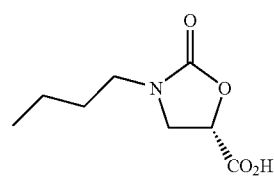

A mixture of the product of Step 1 (480 mg, 1.74 mmol) and 10% Pd/C (48 mg) in MeOH (25 ml) was stirred under $H_2$ (1 atm) for 3.5 h. The mixture was filtered and concentrated to give the title compound (340 mg, 100%). MS m/e 188 $(M+H)^+$.

Preparation 5A

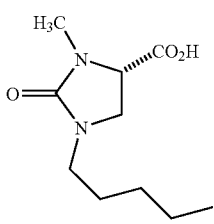

Step 1:

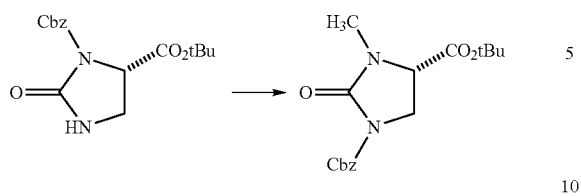

To a stirred ice-cold solution of tert-butyl (4S)-3-(benzyloxycarbonyl)-2-oxoimidazolidine-4-carboxylate (Hayashi et al., J. Med. Chem. 1989, 32, 289) (0.64 g, 2 mmol) in DMF (8 ml) was added NaH (60% dispersion, 84 mg, 2.1 mmol). After 40 min MeI (0.62 ml, 10 mmol) was added and the reaction mixture was allowed to warm to RT. After 16 h the reaction mixture was concentrated and the residue was partitioned between EtOAc (20 ml) and water. The organic layer was washed with sat'd NaCl, dried (MgSO$_4$), filtered and evaporated. The residue was subjected to column chromatography (SiO$_2$; hexanes—2:3 EtOAc/hexanes) to give the product (345 mg).

Step 2:

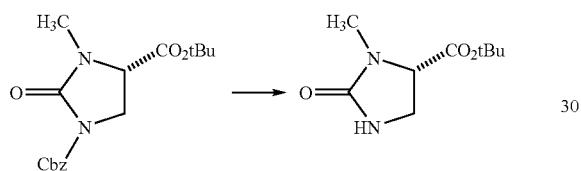

The product of Step 1 (335 mg, 1 mmol) and 10% Pd/C in MeOH (15 ml) was stirred under an atmosphere of H$_2$ for 18 h. The reaction mixture was filtered and the filtrate was evaporated to give the product (183 mg).

Step 3:

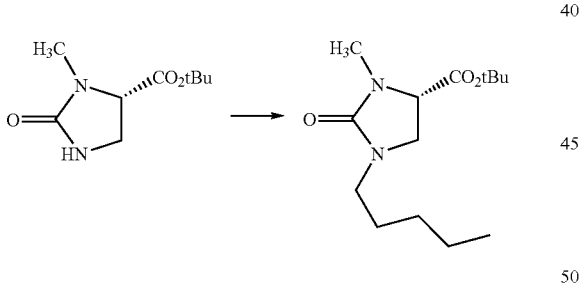

To an ice-cold suspension of NaH (60% dispersion, 35 mg, 0.9 mmol) in DMF (3 ml) was added a solution of the product of Step 2 (173 mg, 0.87 mmol) in DMF (2 ml). After 0.5 h, 1-iodopentane (0.57 ml, 4.3 mmol) was added and the resulting mixture was stirred at RT for 16 h. The reaction mixture was concentrated then partitioned between EtOAc (20 ml) and water. The organic layer was washed with sat'd NaCl, dried (MgSO$_4$), filtered and evaporated. The residue was subjected to column chromatography (SiO$_2$; hexanes—2:3 EtOAc/hexanes) to give the product (205 mg).

Step 4:

The product of Step 3 (200 mg, 0.74 mmol) in 1:4 TFA/CH$_2$Cl$_2$ (5 ml) was stirred for 2 days. The reaction mixture was evaporated and the residue was taken up in 1N HCl in Et$_2$O (2 ml), then evaporated to give the product (209 mg).

By using an analogous procedure to that of Preparation 5A, the following acids were prepared

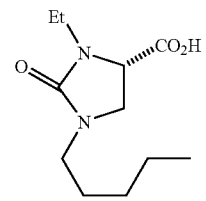

5B

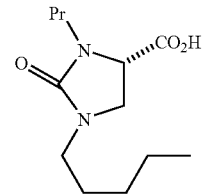

5C

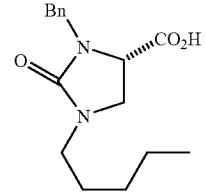

5D

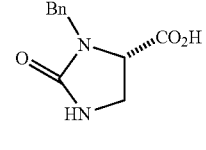

5E

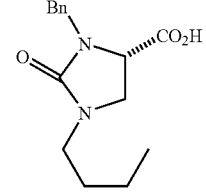

5F

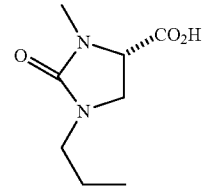

5G

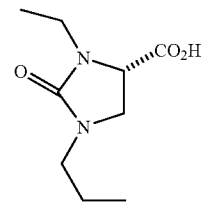

5H

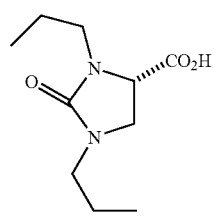

5I

-continued

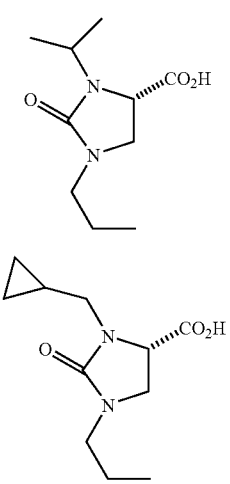

Preparation 6

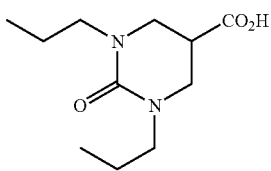

To a solution of 1-propylamine (1.68 ml, 20.5 mmol) in CH₃CN (10 ml) was added a solution ethyl 2-(bromomethyl)acrylate (1.32 g, 6.8 mmol) in CH₃CN (20 ml). After 18 h, Et₂O (100 ml) was added and the suspension was filtered. The filtrate was evaporated and the residue was taken up in EtOAc, washed with water and sat'd NaCl, dried (MgSO₄), filtered and evaporated to give a yellow oil (1.27 g). A mixture of this product (634 mg, 2.75 mmol) and carbonyldiimidazole (535 mg, 3.30 mmol) in THF (14 ml) was stirred for 0.75 h. The reaction mixture was partitioned between EtOAc (100 ml) and 1N HCl. The organic layer was washed with 1N HCl, sat'd NaCl, dried (MgSO₄), filtered and evaporated to give a yellow oil (131 mg). This oil was dissolved in THF (3 ml) and 3N NaOH (0.7 ml) was added. After 18 h, the reaction mixture was acidified with 6N HCl, concentrated, and the residue was subjected to reverse-phase HPLC (Conditions B) to give the product (46 mg) as a white solid.

Preparation 7

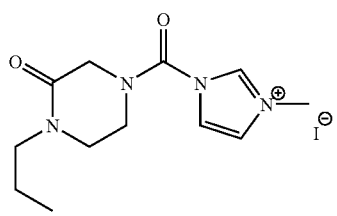

Step 1:

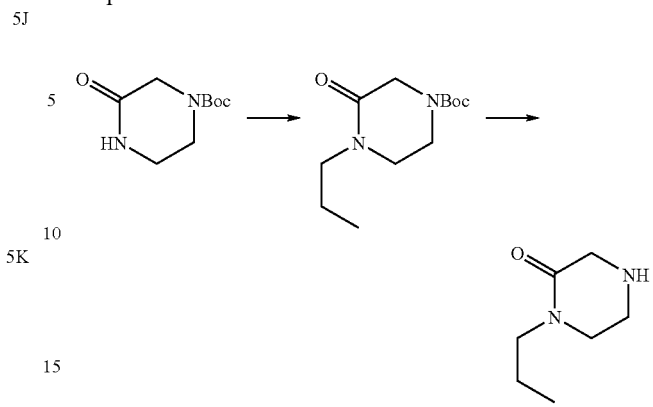

A THF-solution of 1-Boc-piperazin-3-one at 0° C. was treated with NaH (1.5 equiv) and propyl iodide (2 equiv). After stirring the reaction for 18 h at RT, the reaction was quenched with water, acidified with 1 M HCl, and washed with sat'd NaHCO₃. The organic layer was dried (MgSO₄), concentrated, and purified by column chromatography (SiO₂, gradient 4% to 11% hexanes/i-PrOH) to give the alkylated product. Treatment of this product with 20% TFA/CH₂Cl₂, followed by removal of volatiles in vacuo gave the product as a salt.

Step 2:

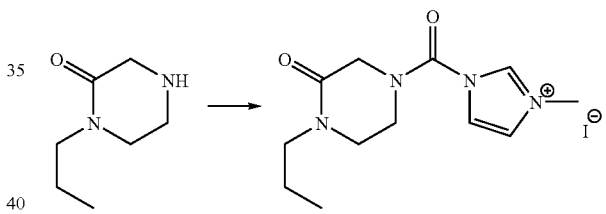

Et₃N (3 equiv) was added to a THF-solution of the product of Step 1 at RT, followed by carbonyldiimidazole (1.2 equiv). The reaction was heated for 18 h at 50° C., then cooled to RT and diluted with EtOAc. The organic layer was sequentially washed with water (4×) and sat'd NaCl (1×), then dried (MgSO₄) and concentrated under vacuum. The resulting residue was dissolved in CH₃CN and treated with excess CH₃I for 6 h at RT. After concentrating the reaction in vacuo, the product was obtained as a yellow foam that was used directly.

Preparation 8

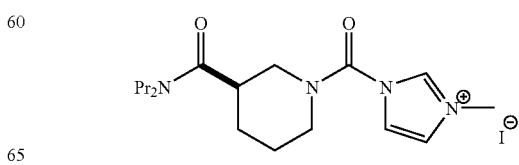

Step 1:

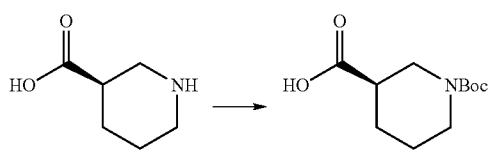

(R)-Nipecotic acid (1.05 g, 8.1 mmol) was dissolved in THF (20 ml) and $H_2O$ (20 ml). $(Boc)_2O$ (2.48 g, 11.4 mmol) and $NaHCO_3$ (0.96 g, 11.4 mmol) was added. The mixture was stirred at RT overnight. The mixture was diluted with $H_2O$ and ether. The aqueous layer was adjusted to pH=2 with concentrated HCl and extracted with $CH_2Cl_2$. The organic layers were combined, dried ($Na_2SO_4$), and concentrated to give N-Boc-(R)-nipecotic acid (1.8 g, 97%). LCMS (Conditions A) $t_R$=3.26 min, 230 (M+H).

Step 2:

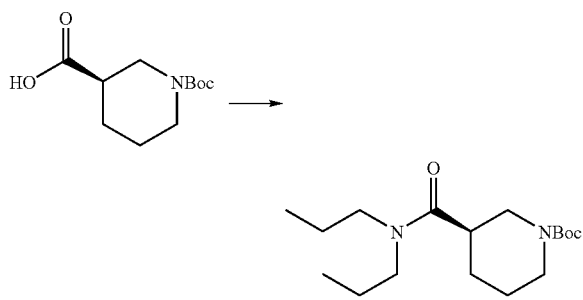

To a solution of the product of Step 1 (1.8 g, 7.9 mmol) and dipropylamine (10.9 ml, 78.6 mmol) in DMF (8 ml) were added PyBOP (5.32 g, 10.2 mmol) and DIEA (4.12 ml, 23.6 mmol). The mixture was stirred at RT overnight. It was diluted with EtOAC and hexane. After the mixture was washed with $H_2O$, the organic layer was dried over $Na_2SO_4$ and concentrated. The crude residue was purified by chromatography ($SiO_2$, 20% EtOAc/hexane) to give the product (2.19 g, 89%). $^1$H NMR (400 MHz, $CDCl_3$) δ 4.04 (m, 2 H), 3.38-3.00 (m, 4 H), 2.95-2.40 (m, 3 H), 1.80-1.50 (m, 8 H), 1.39 (s, 9 H), 0.875 (t, 3 H, J=7.2 Hz), 0.803 (t, 3 H, J=7.2 Hz). LCMS (Conditions A) $t_R$=4.50 min, 313 (M+H).

Step 3:

The product of Step 2 was subjected to 1:4 $TFA/CH_2Cl_2$ to remove the Boc group, then converted to Preparation 8 by essentially the procedure of Preparation 7, Step 2.

Preparation 9

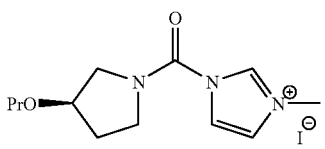

Step 1:

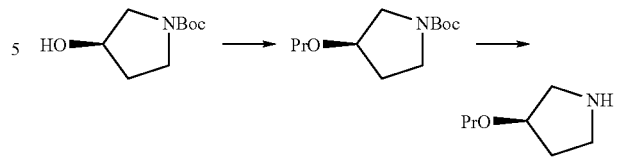

$CsOH—H_2O$ (1.2 equiv) and 4 Å molecular sieves (70 mg/mmol substrate) were added sequentially to a DMF solution of 3-(R)-hydroxy-1-Boc-pyrrolidine at RT. After 10 min, allyl bromide (2.0 equiv) was added and stirring continued for 18 h. The reaction was diluted with EtOAc, filtered, and acidified with 1 M HCl. The organic layer was washed with sat'd aq $NaHCO_3$ (2×) and sat'd NaCl (1×), then dried ($MgSO_4$) and concentrated. The residue was subjected to column chromatography ($SiO_2$, 2% to 4% i-PrOH/hexanes) to give the alkylated intermediate. $Pd(OH)_2$ was added to a solution of this intermediate in MeOH, and the suspension was stirred under $H_2$ for 18 h. The catalyst was removed by filtration and the filtrate was concentrated. The residue was treated with 20% $TFA/CH_2Cl_2$ at RT for 2 h, then evaporated in vacuo to give the product as a salt (100%).

Step 2:

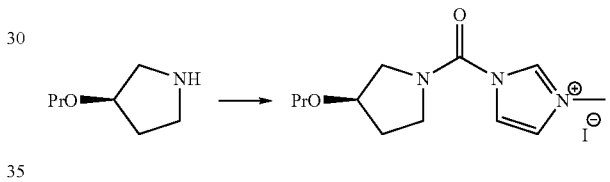

The product of Step 1 was converted to Preparation 9 by essentially the same procedure set forth in Preparation 7, Step 2.

Preparation 10A

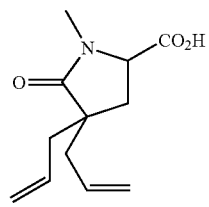

Step 1:

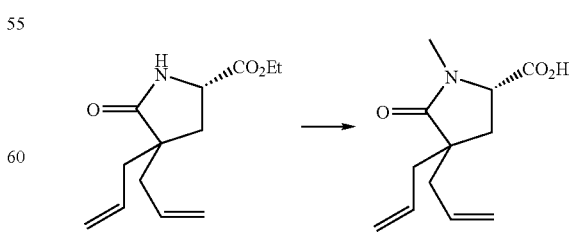

To an ice-cold solution of ethyl 2(S)-4,4-diallylpyroglutamate, which was prepared from ethyl 2(S)-1-(tert-butoxycarbonyl)-4,4-diallylpyroglutamate, (Ezquerra et al., *J.*

*Org. Chem.*, (1994), 59, 4327; 1.2 g, 3.6 mmol) and methyl iodide (0.25 ml, 4 mmol) in anhydrous THF (18 ml) was added NaH (60% dispersion; 216 mg, 6 mmol). After 0.5 h, the reaction mixture was allowed to warm to RT and stirred for 1 h. The reaction mixture was quenched with sat'd NaCl, and extracted with $Et_2O$ (×2). The combined organic layers were washed with sat'd NaCl, dried ($MgSO_4$), filtered and evaporated to give the methylated product (1.2 g) as an oil. This oil was dissolved in THF (20 ml) and 3 N NaOH (5 ml) was added. After 22 h, the reaction mixture was acidified with 6 N HCl and extracted with $Et_2O$ (×3). The combined organic layers were dried ($MgSO_4$), filtered and evaporated. Preparative HPLC (Conditions B) gave the product (215 mg) as an oil.

Preparation 10B

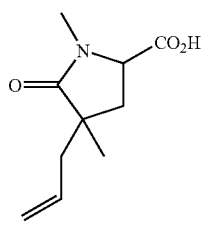

In analogy to Preparation 10A, Preparation 10B was obtained.

Preparation 11

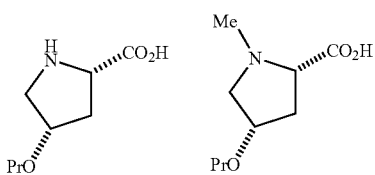

Step 1:

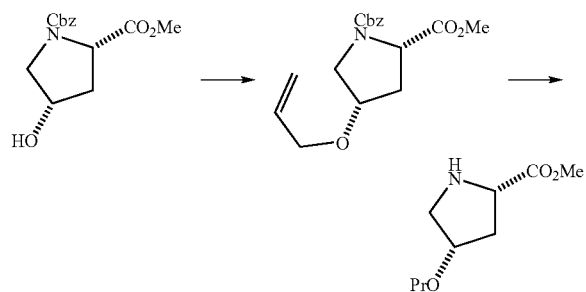

(2S,4S)-N-benzyloxycarbonyl-4-hydroxyproline methyl ester was treated with NaH/DMF and allyl bromide. The resulting intermediate in MeOH was stirred under 50 psi $H_2$ in the presence of 20% Pd(OH)$_2$/carbon and catalytic AcOH. After filtration and evaporation the product was obtained.

Step 2:

A mixture of the product of Step 1, 37% aqueous HCHO, NaOAc and 20% Pd(OH)$_2$/C in MeOH was stirred under 50 psi $H_2$. After 20 h at RT, the reaction mixture was filtered, concentrated, then dissolved in 3 M HCl. The aqueous layer was washed with $Et_2O$ (2×), and basified with $NaHCO_3$. After extracting with $CH_2Cl_2$ (3×), the organic layer was dried ($MgSO_4$), and concentrated. The residue was treated with 3 M NaOH/THF for 18 h at RT. After acidifying the reaction mixture with 4 M HCl/dioxane, the mixture was extracted with $CH_2Cl_2$, and the organic layer concentrated to give the product mixture that was used directly.

Preparation 12

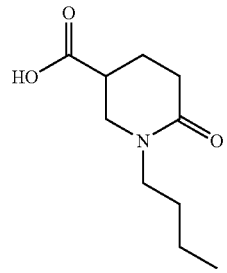

Step 1

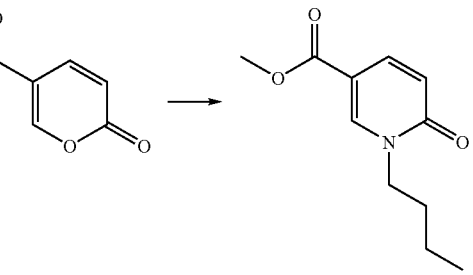

To a stirred, ice-cold solution of n-butylamine (3.29 g, 45 mmol) in MeOH (20 ml) was added an ice-cold solution of methyl coumalate (3.08 g, 20 mmol) in MeOH (25 ml) dropwise. After 18 h the reaction mixture was concentrated and the residue was subjected to column chromatography ($SiO_2$; 0%-1.5% MeOH/$CH_2Cl_2$) to give the product (2.3 g).

Step 2:

A mixture of the product of Step 1 (1.34 g, 6.4 mmol) and $PtO_2$ (134 mg) in MeOH (100 ml) was stirred under 50 psi $H_2$ for 24 h. Additional $PtO_2$ (400 mg) was added and the reaction mixture was stirred under 50 psi $H_2$ for 6 h. The reaction mixture was filtered and the filtrate was concentrated. Column chromatography of the residue ($SiO_2$; 0%-2% MeOH/$CH_2Cl_2$) gave methyl 1-butyl-6-oxopiperidine-3-carboxylate (820 mg). A mixture of methyl 1-butyl-6-oxopiperidine-3-carboxylate (800 mg, 3.8 mmol) and 1N NaOH (7.5 ml) in MeOH (15 ml) was stirred at RT for 1 h. The reaction mixture was acidified with 1N HCl and extracted with $Et_2O$ (2×100 ml). the combined organic layers were washed with sat'd NaCl, dried (Na$_2$SO$_4$), filtered and evaporated to give the product (590 mg) that was used without further purification.

Preparation 13

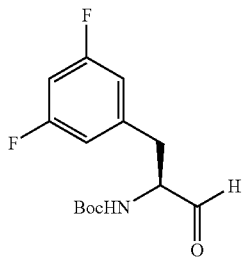

Step 1:

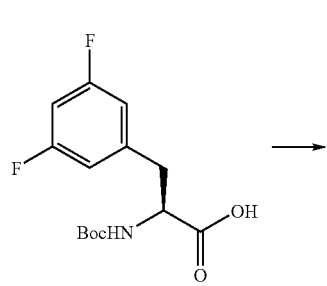

To a stirred, ice-cold mixture of (S)-Boc-3,5-difluorophenylalanine (20.00 g, 66.4 mmol) in MeOH (50 ml) and toluene (250 ml) was added (trimethylsilyl)diazo-methane (53 ml, 106 mmol, 2.0 M in hexane) in portions. After the addition, the reaction was stirred for about 0.5 h, quenched with glacial AcOH (1 ml) and concentrated in vacuo. The residue was used directly in the next step. The residue was dissolved in anhydrous THF (200 ml), cooled to 0° C., and LiAlH$_4$ (2.52 g, 66.4 mmol) was added in portions. After the addition, the reaction was allowed to stir at 0° C. for 20 min then quenched with of 15% aq. NaOH (2.0 ml) and H$_2$O (8.0 ml). The resulting slurry was filtered, the residue washed with THF, and the combined filtrate and washings were concentrated in vacuo to give the product as a white solid (17.65 g, 93%). $^1$H NMR (CDCl$_3$) δ 6.73 (m, 2H), 6.62 (m, 1H), 4.75 (s, br, 1H), 3.80 (s, br, 1H), 3.61 (m, 1H), 3.52 (m, 1H), 2.80 (m, 2H), 1.37 (s, 9H). MS m/e 288 (M+H)$^+$.

Step 2:

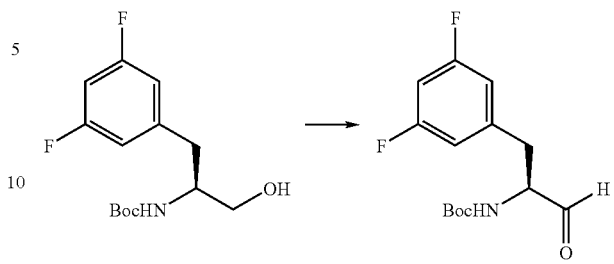

A flask charged with the product of Step 1 (3.00 g, 10.5 mmol), EtOAc (150 ml) and IBX (8.78 g, 31.4 mmol) was heated to 95° C. and stirred for 3.5 h. The reaction mixture was allowed to cool to RT, filtered and concentrated in vacuo to provide the product as white solid (2.98 g, 100%). $^1$H NMR (CDCl$_3$) δ 9.59 (s, 1H), 6.65 (m, 3H), 5.03 (m, 1H), 4.35 (m, 1H), 3.13 (m, 1H), 3.01 (m, 1H), 1.39 (s, 9H).

Preparation 14

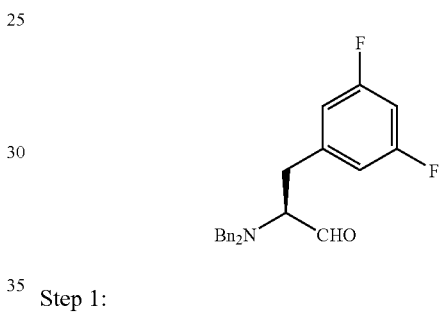

Step 1:

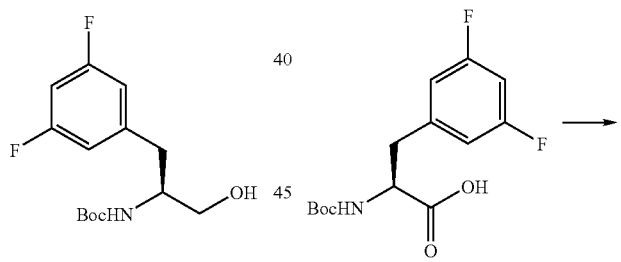

Trimethylsilyldiazomethane (2.0 M Hexanes, 95 ml, 190 mmol) was added to a solution of Boc-(L)-3,5-difluorophenylalanine (40 g, 133 mmol) in MeOH (50 ml) and toluene (250 ml) at 0° C. After 60 min at RT, AcOH was added to quench the excess trimethylsilyldiazomethane, and the reaction mixture was concentrated under vacuum to give the methyl ester in quantitative yield (42.3 g). 4 M HCl/dioxane (150 ml, 600 mmol) was added to a solution of the methyl ester (42.3 g) in 20% MeOH/CH$_2$Cl$_2$ (130 ml) at 0° C., and the reaction was stirred for 4 h at RT. The reaction was concentrated under vacuum to give the product HCl salt (33.4 g, quantitative). LCMS (Conditions A): $t_R$=2.62 min; 431 $(2M+H)^+$, 216 $(M+H)^+$.

Step 2:

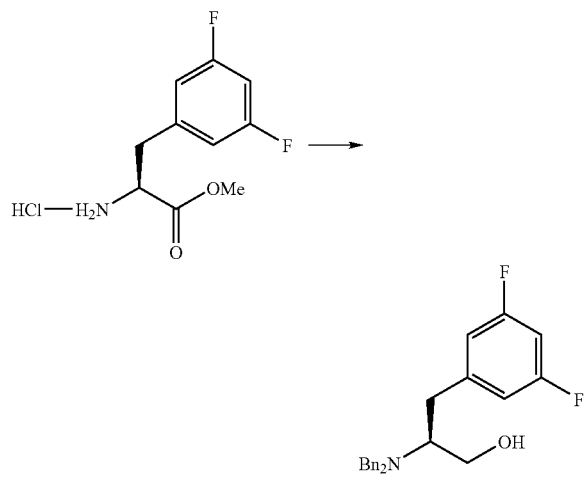

NaHCO$_3$ (55.9 g, 665 mmol) and BnBr (68.2 g, 399 mmol) were added to a solution of the product of Step 1 (33.4 g, 133 mmol) in THF (600 ml) and DMSO (150 ml) at RT. The reaction mixture was stirred for 24 h at 70° C., then cooled to RT and diluted with water (400 ml). After stirring for 1 h at RT, the layers were separated and the aqueous layer extracted with EtOAc (3×). The combined organic layers were washed (NaHCO$_3$), dried (MgSO$_4$) and concentrated, and the residue chromatographed (SiO$_2$, 0% to 30% EtOAc/Hexanes) to give the intermediate N,N-dibenzylated methyl ester (39.4 g, 75%). LCMS (Conditions A) $t_R$=5.90 min; 396 $(M+H)^+$.

LiAlH$_4$ (6.49 g, 171 mmol) was added to a solution of the methyl ester (45.0 g, 114 mmol) in THF (500 ml) at 0° C. After the addition was completed, the reaction mixture was stirred at RT for 5 h, then quenched with water (5 ml), 15% NaOH (10 ml) and an additional amount of water (7 ml). After vigorously stirring the suspension, the mixture was filtered, and the filtrate concentrated. The resulting residue was chromatographed (SiO$_2$, 0% to 50% EtOAc/Hexanes) to give the product (34.8 g, 71%). LCMS (Conditions A) $t_R$=4.53 min; 368 $(M+H)^+$.

Step 3:

DMSO (4.45 ml, 62.7 mmol) in CH$_2$Cl$_2$ (10 ml) was added to a solution of oxalylchloride (2.70 ml, 31.3 mmol) in CH$_2$Cl$_2$ (60 ml) at −78° C. After 10 min, a solution of the product of Step 2 (10.0 g, 27.2 mmol) in CH$_2$Cl$_2$ (40 ml) was added. The reaction mixture was stirred for 90 min at −78 DC, followed by addition of DIEA (18.8 ml, 108 mmol). The reaction mixture was stirred for 2 h at RT, then quenched with water. The aqueous layer was extracted with CH$_2$Cl$_2$, and the combined organic layers washed (2× water, 2×NH$_4$Cl, 1× brine), dried (MgSO$_4$), and concentrated to give the product (10.32 g, >theoretical yield). $^1$H NMR (400 MHz, CDCl$_3$) δ=9.72 (s, 1 H), 7.33-7.24 (m, 10 H), 6.65-6.61 (m, 3 H), 3.82 (d, J=13.6 Hz, 2H), 3.68 (d, J=14 Hz, 2H), 3.51 (m, 1 H), 3.10 (m, 1 H), 2.86 (m, 1H).

Preparation 15

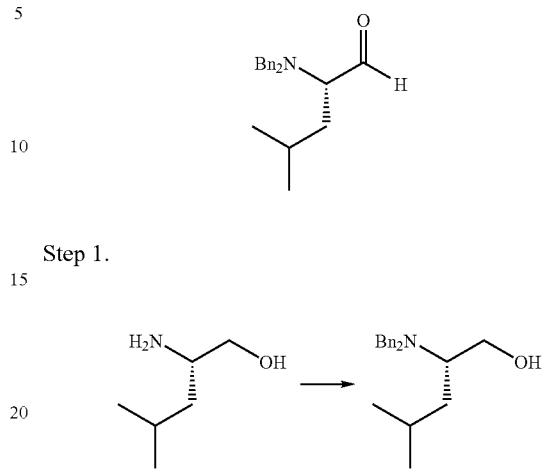

Step 1.

L-Leucinol (5.27 g, 45.0 mmol) was added to a stirred solution of potassium carbonate (17.76 g, 128.5 mmol) in water (25 ml) at RT and the mixture was heated to 65° C. A solution of benzyl bromide (15.44 g, 90.27 mmol) in EtOH (12 ml) was added and the mixture was stirred at 65° C. for 1 h. The mixture was diluted with CH$_2$Cl$_2$ (50 ml) and water (25 ml), the aqueous layer was extracted with CH$_2$Cl$_2$ (50 ml) and the combined organic layers were dried (MgSO$_4$), concentrated, and purified by column chromatography (SiO$_2$, gradient EtOAc/Hexanes 0-8%) to give the product (12.63 g, 94%). MS m/e 298 $(M+H)^+$.

Step 2:

The product of Step 1 was converted to the aldehyde by essentially the procedure of Preparation 14, Step 3, and was used directly.

Preparation 16

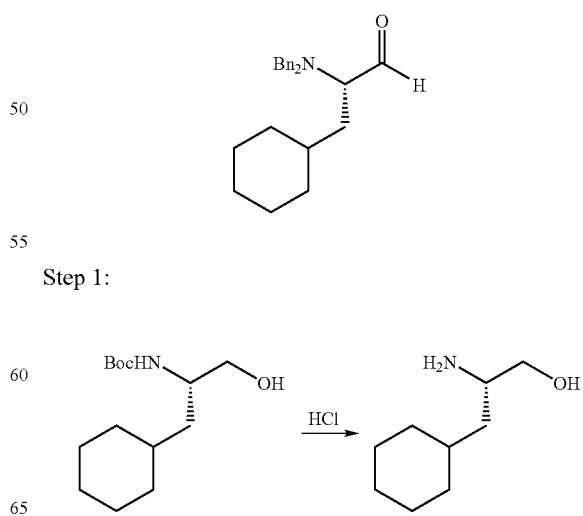

Step 1:

A mixture of (S)-2-t-butoxycarbonylamino-3-cyclohexyl-1-propanol (4.00 g, 15.5 mmol) in CH$_2$Cl$_2$ (10 ml) and 4N HCl in dioxane (10 ml) was stirred at RT for 16 h. The mixture was diluted with CH$_2$Cl$_2$ (40 ml) and washed with aqueous NH$_4$OH (30 ml). The aqueous layer was extracted with CH$_2$Cl$_2$ (40 ml) and the combined organic layer was dried (MgSO$_4$) and concentrated to give the product (2.78 g, 100%). MS m/e 158 (M+H)$^+$.

Step 2

The product of Step 1 was dibenzylated in analogy to the procedure of Preparation 15, Step 1. The dibenzylated product was converted to the product aldehyde in analogy to the procedure of Preparation 14, Step 3.

Example 1

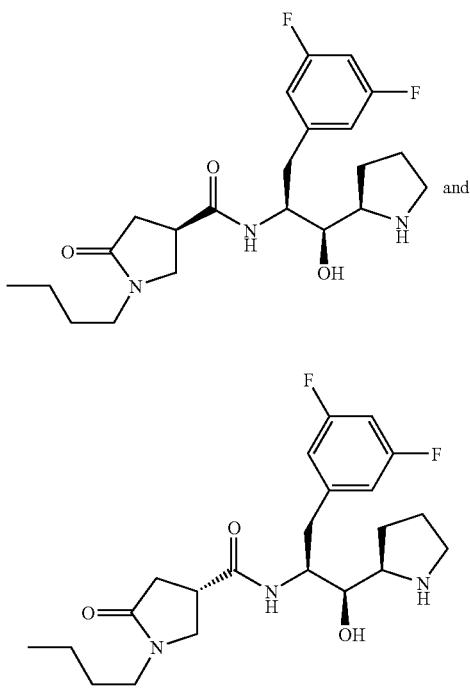

Step 1:

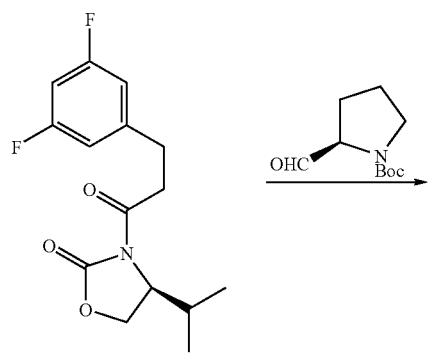

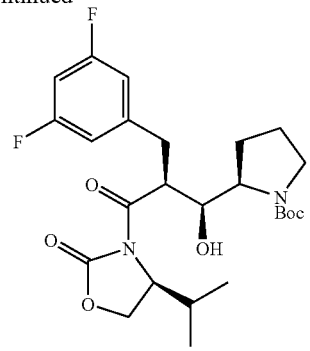

In analogy to the literature procedure (Pettit et al. *Synthesis* (1996), 719-725), NEt$_3$ (2.0 ml, 14.44 mmol) was added to a solution of Preparation 1 (3.31 g, 11.16 mmol) in CH$_2$Cl$_2$ (46 ml) at 0° C., followed by dropwise addition of Bu$_2$BOTf (1.0 M in CH$_2$Cl$_2$, 12.0 ml, 12 mmol). After 45 min at 0° C., the yellow solution was cooled to −78° C., and a solution of N-(tert-butoxycarbonyl)-D-prolinal (2.46 g, 12.34 mmol) in CH$_2$Cl$_2$ (5 ml) was added. The reaction was stirred for 1 h at −78° C., 2 h at 0° C. and 1 h at 23° C., and was quenched with MeOH (75 ml)-phosphate buffer (pH 7.0, 25 ml). After cooling the solution to −10° C., a solution of H$_2$O$_2$ (30% in water, 25 ml)-MeOH (50 ml) was added such that the internal temperature remained below 4° C. After stirring for 60 min at 23° C., the volatiles were removed in vacuo, and the aqueous residue was extracted with Et$_2$O (3×), dried (Na$_2$SO$_4$) and concentrated under reduced pressure. Purification of the residue by chromatography (SiO$_2$, 20→30% EtOAc/hexanes) gave the product (3.03 g, 61%) along with recovered imide (1.98 g, 6.66 mmol). $^1$H NMR (400 MHz, CDCl$_3$) δ 6.83 (m, 2 H), 6.51 (m, 1 H), 4.57 (m, 1 H), 4.33 (m, 1 H), 3.94-4.15 (m, 3 H), 3.80 (m, 1 H), 3.23-3.39 (m, 4 H), 2.99 (t, 1 H, J=12.8 Hz), 1.98 (m, 1 H), 1.97 (m, 1 H), 1.76 (m, 3 H), 1.48 (s, 9 H), 0.73 (d, 3 H, J=6.8 Hz), 0.29 (d, 3 H, J=6.8 Hz); LCMS (Conditions A): t$_R$=4.65 min, 497 (M+H)$^+$, 441 (M-Bu+H)$^+$, 397 (M-Boc+H)$^+$.

Step 2:

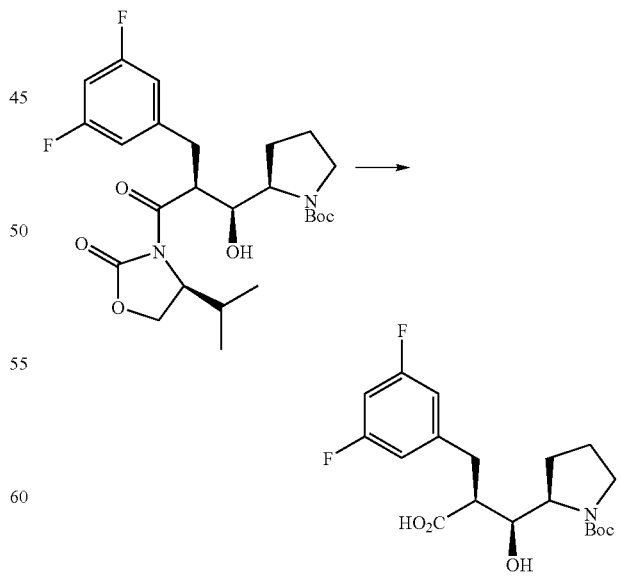

To a solution of the product of Step 1 (3.91 g, 7.89 mmol) in THF (45 ml) and water (11 ml) at 0° C. was added H$_2$O$_2$ (30% in water, 3.9 ml), followed by an aqueous solution of LiOH (378 mg, 15.78 mmol in 24 ml water, sonicated to completely dissolve LiOH). After 18 h at 0° C., the reaction was quenched with saturated aqueous $Na_2SO_3$ and stirred at 23° C. for 2 h. After removal of all volatiles, the residue was diluted with $NaHCO_3$, extracted with $CH_2Cl_2$ (3×), acidified to pH 2 (1 N HCl), salted out with NaCl (s) and extracted with $Et_2O$ (3×). The combined organic layers were washed with water (1×) and brine (1×), dried ($Na_2SO_4$) and concentrated in vacuo to yield the product (2.24 g, 5.80 mmol, 74%); $^1H$ NMR (400 MHz, $CDCl_3$) δ 6.71 (m, 2 H), 6.57 (m, 1 H), 4.09 (m, 1 H), 3.90 (m, 1 H), 3.49 (m, 1 H), 3.10-3.23 (m, 2 H), 2.86 (m, 1 H), 2.64 (m, 1 H), 1.47-2.00 (m, 4 H), 1.48 (s, 9 H); LCMS (Conditions A): $t_R$=3.93 min, 386 $(M+H)^+$, 330 $(M-Bu+H)^+$, 286 $(M-Boc+H)^+$.

Step 3:

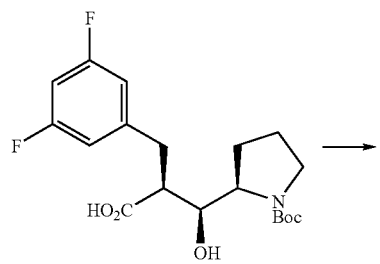

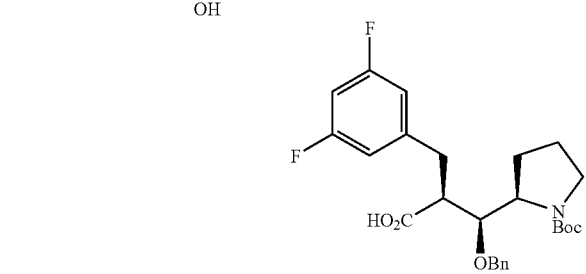

To a solution of the product of Step 2 (2.23 g, 5.80 mmol) in DMF (20 ml) at −78° C. was added NaH (60%, 510 mg, 12.75 mmol), followed by benzyl bromide (810 μl, 6.81 mmol). The reaction was warmed to 23° C. over 18 h. The volatiles were removed in vacuo, and the residue was taken up in water-$Et_2O$. The aqueous layer was extracted with $Et_2O$ (2×), adjusted to pH 3 (1 M HCl), extracted with EtOAc (3×), and the combined organic layers were dried ($MgSO_4$) and concentrated under reduced pressure. Purification of the residue by chromatography ($SiO_2$, 10→50% EtOAc/hexanes containing 1% AcOH) gave recovered starting material (372 mg, 0.97 mmol) and the product (616 mg, 22%); $^1H$ NMR (400 MHz, $CDCl_3$, complicated by the presence of rotamers) δ 8.0-9.0 (bs, 1 H), 7.21 (m, 5 H), 6.68 (m, 2 H), 6.60 (m, 1 H), 4.50-4.64 (m, 2 H), 3.60-3.83 (m, 1 H), 3.37-3.60 (m, 2 H), 3.07-3.24 (m, 2 H), 2.82 (m, 1 H), 2.60 (m, 1 H), 1.96-2.08 (m, 1 H), 1.79-1.96 (m, 2 H), 1.66 (m, 1 H), 1.40 (m, 9 H); MS 498 $(M+Na)^+$, 420 $(M-Bu+H)^+$, 376 $(M-Boc+H)^+$.

Step 4:

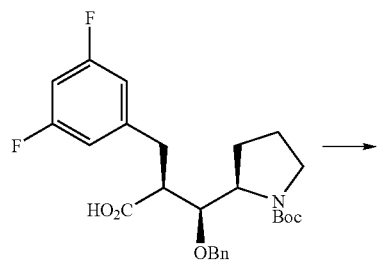

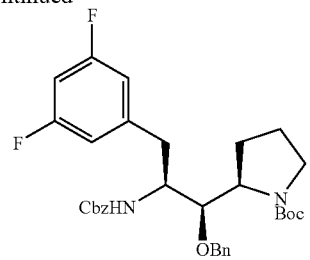

$NEt_3$ (155 μL, 1.12 mmol) and DPPA (145 μL, 0.67 mmol) were added to the product of Step 3 (265 mg, 0.56 mmol) in toluene (3 ml) at 23° C. After 3 h at 95° C., BnOH (240 μl, 2.24 mmol) was added, followed by stirring at 80° C. for 18 h. After removing the volatiles in vacuo, the residue was purified by chromatography ($SiO_2$, 5→10% EtOAc/hexanes) and normal-phase HPLC (1→10% iPrOH/hexanes) to give the product (103 mg, 32%). $^1H$ NMR (400 MHz, $CDCl_3$) δ 7.17-7.30 (m, 10 H), 6.57-6.70 (m, 3 H), 5.30 (m, 1 NH), 4.85-5.05 (m, 2 H), 4.40-4.56 (m, 2 H), 4.05 (m, 1 H), 3.65-3.95 (m, 2 H), 3.00-3.60 (m, 3 H), 2.40-2.60 (m, 1 H), 2.05 (m, 1 H), 1.55-1.95 (m, 3 H), 1.41 (s, 9 H); LCMS (Conditions A): $t_R$=5.18 min, 581 $(M+H)^+$, 525 $(M-Bu+H)^+$, 481 $(M-Boc+H)^+$.

Step 5:

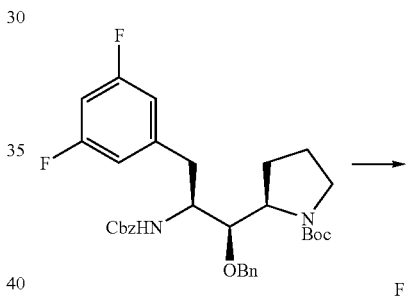

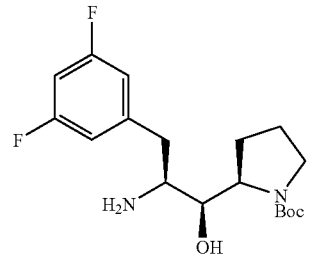

A solution of the product of Step 4 (100 mg, 172 μmol) in MeOH (4 ml) was hydrogenated over 20% $Pd(OH)_2$/C (40 mg) at 1 atm of $H_2$ pressure for 18 h. The mixture was filtered and concentrated under reduced pressure to yield the product (61 mg, 100%) which was used without further purification in the next step.

Step 6:

To EDC-resin (60 mg, 84 mmol at 1.45 mmol/g loading) was added a solution of the product of Step 5 (10 mg, 28 mmol in 500 μl of THF/$CH_3CN$/DMF, 2:2:1 v/v/v), followed by a solution of HOBt (5.7 mg, 42 μmol in 200 μl THF) and a solution of Preparation 2A (6.6 mg, 34 mmol in 700 μl THF/$CH_3CN$, 1:1 v/v). After gently shaking the reaction for 18 h at 23° C., PS-trisamine resin (39 mg, 170 μmol at 4.36 mmol/g loading) and PS-NCO resin (58 mg, 85 mmol at 1.47 mmol/g loading) was added. After 6 h of further shaking, the reaction was filtered, the resin washed with THF (2×1 ml), and the volatiles removed under vacuum. The product was deprotected using 20% TFA/CH$_2$Cl$_2$ (3 ml) for 6 h at 23° C., followed by removal of volatiles under vacuum. The resulting residue was exposed to 1 M HCl/MeOH (300 μl) for 30 min at 23° C., then concentrated under vacuum to give the product (7.7 mg, 17 μmol, 60%). $^1$H NMR (400 MHz, CD$_3$OD) δ 6.70-6.84 (m, 3 H), 3.99 (m, 1 H), 3.81-3.88 (m, 1 H), 3.60-3.68 (m, 2 H), 3.48 (m, 1 H), 3.43 (m, 1 H), 3.03-3.15 (m, 2 H), 2.79 (m, 1 H), 2.38-2.66 (m, 2 H), 1.90-2.08 (m, 5 H), 1.15-1.44 (m, 7 H), 0.87 (m, 3 H, J=7.6 Hz); LCMS (Conditions A) t$_R$=3.42 min (isomer 1) and t$_R$=3.63 min (isomer 2), 424 (M+H), 406 (M−H$_2$O+H).

By essentially the same procedure set forth in Example 1, substituting Preparations 2Q and 4, Examples 1B and 1C were prepared.

Example 1B

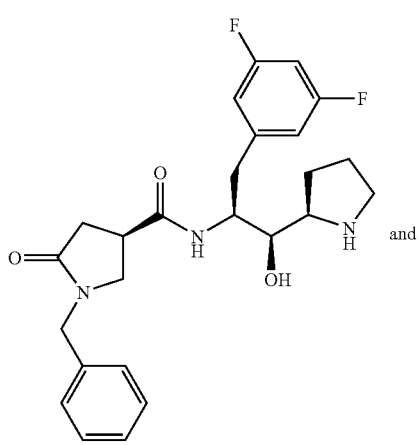
and
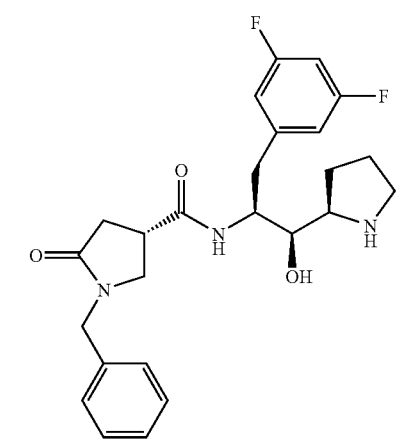

$^1$H NMR δ 7.12-7.30 (m, 5 H), 6.79 (m, 3 H), 6.55 (m, 1 H), 4.37 (m, 1 H), 4.30 (m, 1 H), 3.90-4.00 (m, 1 H), 3.80-3.85 (m, 1 H), 3.63 (m, 1 H), 3.54-3.60 (m, 1 H), 3.44 (m, 1 H), 3.03 (m, 1 H), 2.44-2.70 (m, 5 H), 1.80-2.11 (m, 6 H). Isomer 1: LCMS (Conditions A): t$_R$=3.58 min; 458 (M+H). Isomer 2: LCMS (Conditions A): t$_R$=3.74 min; 458 (M+H).

Example 1C

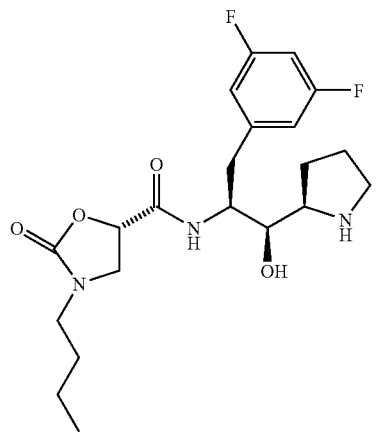

$^1$H NMR δ=6.70-6.80 (m, 3 H), 4.78 (m, 1 H), 4.07 (m, 1 H), 3.91 (m, 1 H), 3.66-3.72 (m, 2 H), 3.15-3.24 (m, 3 H), 3.00-3.05 (m, 2 H), 2.64 (m, 1 H), 1.80-2.09 (m, 5 H), 1.49 (m, 1 H), 1.39 (m, 2 H), 1.20-1.33 (m, 4 H), 0.90 (t, 3H, J=7.2 Hz). LCMS (Conditions A): t$_R$=3.81 min; 426 (M+H).

Example 1D

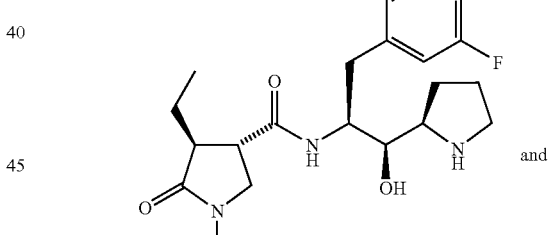
and
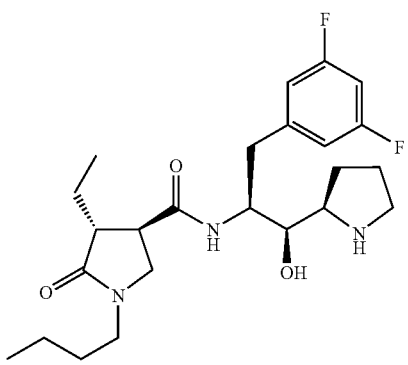

Step 1:

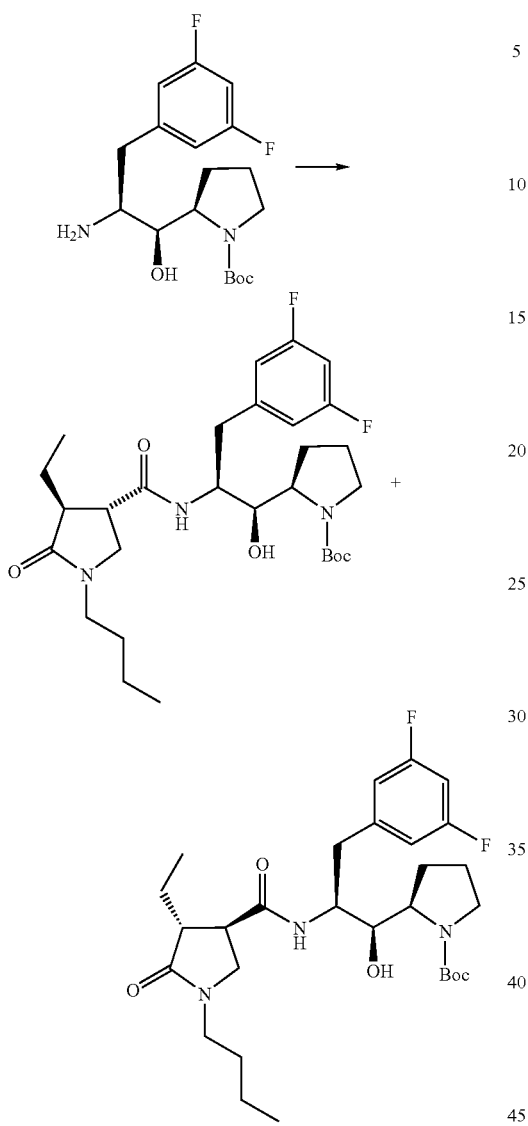

A mixture of Preparation 3A (30 mg, 0.14 mmol), Example 1, Step 5 (46 mg, 0.13 mmol), HOBt (18 mg, 0.13 mmol), EDCl (25 mg, 0.13 mmol), and Et$_3$N (19 μl, 0.14 mmol) in CH$_2$Cl$_2$ (5 ml) was stirred at RT for 16 h. The mixture was diluted with CH$_2$Cl$_2$ (50 ml) and washed with 0.5N NaOH (30 ml). The organic layer was dried (MgSO$_4$), concentrated, and purified by PTLC (1:20 MeOH/CH$_2$Cl$_2$) to give the desired product (33 mg, 46%). MS m/e 574 (M+Na)$^+$.

Step 2:

A solution of the product of Step 1 (33 mg, 0.060 mmol) and TFA (1 ml) in CH$_2$Cl$_2$ (5 ml) was stirred in an ice-water bath for 30 min then at RT for 4 h. The mixture was diluted with CH$_2$Cl$_2$ (40 ml) and washed with 5N NH$_4$OH (10 ml). The organic layer was dried (MgSO$_4$), concentrated, and purified by PTLC (15% 2M NH$_3$/MeOH-85% CH$_2$Cl$_2$) to give isomer 1 (5.5 mg, 20%) and isomer 2 (13 mg, 48%). Isomer 1: $^1$H NMR (400 MHz, CDCl$_3$) δ 6.97 (m, 1H), 6.71 (m, 2H), 6.61 (m, 1H), 4.11 (m, 1H), 3.88 (m, 1H), 3.51 (m, 1H), 3.38 (m, 1H), 3.05-3.30 (m, 6H), 2.87 (m, 1H), 2.60 (m, 1H), 2.50 (m, 1H), 1.80-2.10 (m, 4H), 1.55 (m, 1H), 1.15-1.50 (m, 6H), 0.85 (m, 3H), 0.74 (m, 3H). MS m/e 452 (M+H)$^+$.
Isomer 2: $^1$H NMR (400 MHz, CDCl$_3$) δ 6.55-6.80 (m, 4H), 3.80-4.30 (m, 3H), 3.61 (m, 1H), 2.45-3.35 (m, 11H), 1.60-1.90 (m, 5H), 1.15-1.45 (m, 5H), 0.85 (m, 6H). MS m/e 452 (M+H)$^+$.

Example 2A

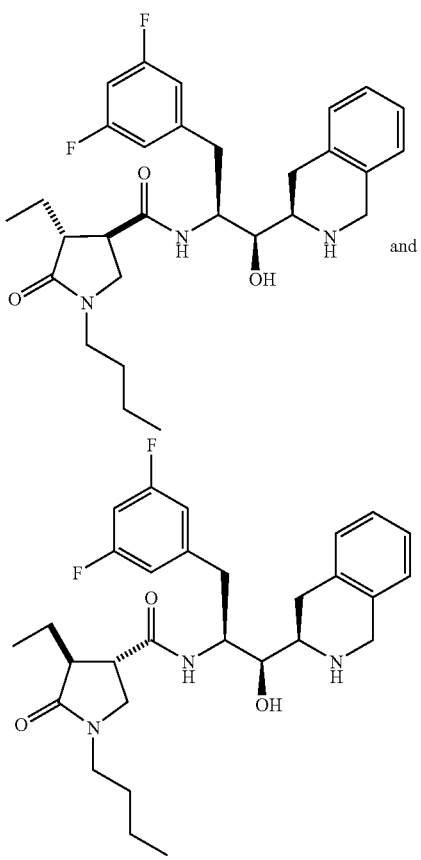

Step 1:

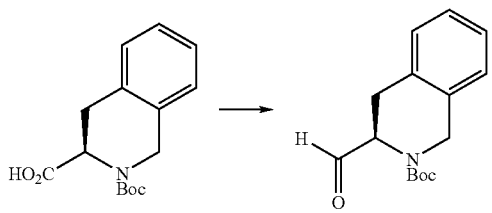

To a solution of N-Boc-D-1,2,3,4-tetrahydroisoquinoline-3-carboxylic acid (2.60 g, 9.38 mmol) in toluene/MeOH (5/1, 50 ml) added (trimethylsilyl)diazomethane (2 M in hexanes) until bright yellow color persisted in the reaction. The reaction was stirred for 5 min, then AcOH was added dropwise until the yellow color faded completely. The solution was concentrated, and this crude product was used without purification.

To a 0° C. solution of a portion of the above material (2.30 g, 7.90 mmol) was added LiAlH$_4$ (600 mg, 15.8 mmol) as a solid in two portions. The reaction was allowed to warm to RT overnight. After 18 h, the reaction was quenched by slow addition of water (1 ml), followed by aq. NaOH (1.5 ml, 25% w/v), and finally more water (2 ml). The resulting mixture was stirred vigorously for 1 h, then filtered and concentrated. The crude residue was purified by column chromatography (silica, 0→65% EtOAc/hexanes) to give the desired product (500 mg, 1.89 mmol, 24%). LCMS (Conditions A): $t_R$=4.2 min; (M+H)$^+$=264.

To a −78° C. solution of oxalyl chloride (215 μl, 318 mg, 2.51 mmol) in CH$_2$Cl$_2$ (5.5 ml) was added DMSO (222 μl, 245 mg, 3.13 mmol). After 5 min, a −78° C. solution of the product of the previous step (550 mg, 2.09 mmol) in CH$_2$Cl$_2$ (5 ml) was added via cannula. After 40 min at −78° C., DIEA (1.1 ml, 810 mg, 6.3 mmol) was added all at once, and the cooling bath was removed from the reaction. After 10 min, the mixture was diluted with water and additional CH$_2$Cl$_2$. The phases were separated, and the aqueous phase was extracted once with CH$_2$Cl$_2$. The organic portions were combined, washed with brine, dried over MgSO$_4$, filtered, and concentrated. The crude product was used in subsequent steps without further purification.

Step 2:

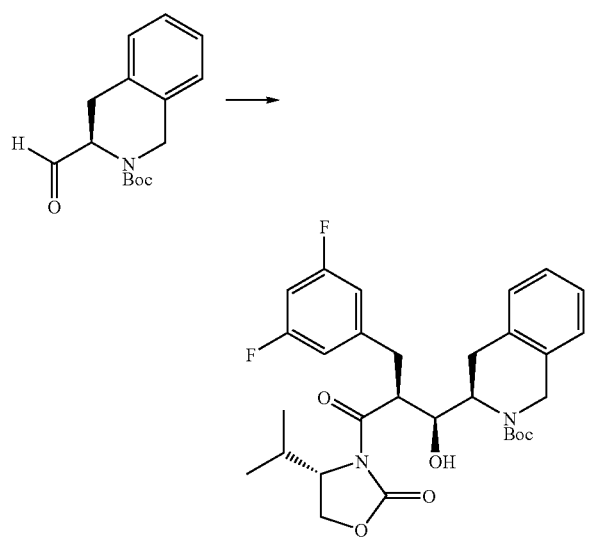

To a −20° C. solution of the product of Preparation 1 (745 mg, 2.51 mmol) in CH$_2$Cl$_2$ (10.5 ml) was added Et$_3$N (0.43 ml, 320 mg, 3.1 mmol). After 5 min, di-n-butylboron triflate (1 M in CH$_2$Cl$_2$, 2.72 ml, 2.72 mmol) was added via syringe over 2 min. The reaction was transferred to an ice/brine bath, stirred for 2 h, and then cooled to −78° C. A 0° C. solution of the product of the Step 1 (assumed 2.09 mmol) in CH$_2$Cl$_2$ (3 ml) was added dropwise via cannula over 5 min, followed by a CH$_2$Cl$_2$ rinse (1 ml). This mixture was warmed stepwise to RT as follows: 1.5 h at −78° C., 1.0 h at 0° C., 1.0 h at RT. The reaction mixture was then quenched by addition of pH 7 phosphate buffer (~10 ml) and MeOH (~10 ml). The resulting mixture was cooled in an ice/brine bath, and a solution of 35% H$_2$O$_2$/MeOH (1/2, 15 ml) was added slowly, such that the internal temperature of the reaction remained <5° C. After this addition, the mixture was warmed to RT and stirred for 45 min. The mixture was further diluted with MeOH and water, then partially concentrated. The mixture was diluted with EtOAc and brine. The phases were separated, and the aqueous portion was extracted with EtOAc (4×). The combined organic fractions were washed with sat. aq. NaHCO$_3$ and brine, then dried over MgSO$_4$, filtered, and concentrated. The crude material was purified by column chromatography (silica, 0→75% EtOAc/hexanes) to give the desired product (668 mg, 1.20 mmol, 57%). LCMS (Conditions A): $t_R$=5.3 min; (M+H)$^+$=559.

Step 3:

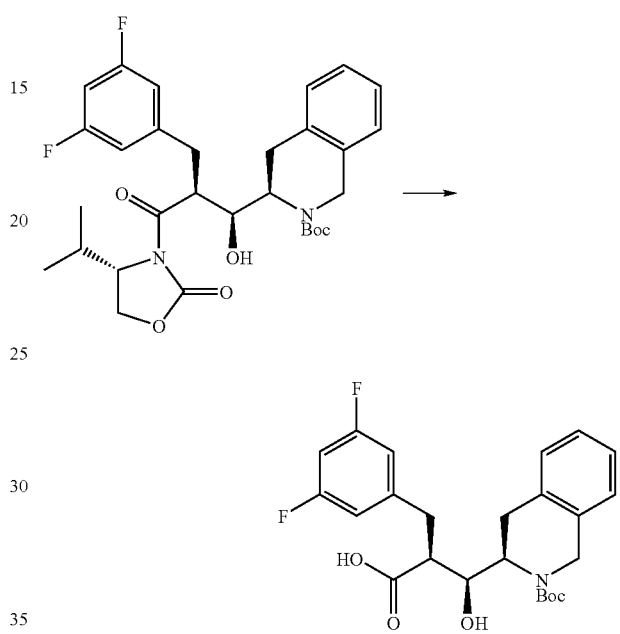

To a 0° C. solution of the product of Step 2 (610 mg, 1.09 mmol) in THF/water (5/1, 6 ml) was added 35% aq. H$_2$O$_2$ (0.44 ml) followed by a suspension of LiOH (77 mg, 1.8 mmol) in water (2 ml) that had been sonicated for 10 min. The reaction was stirred at 0° C. for 8 h, then diluted with an aq. Na$_2$SO$_3$ solution (1 g in 5 ml water) and let warm to RT overnight. The mixture was diluted with 1N HCl and CH$_2$Cl$_2$. The phases were separated and the aqueous extracted with CH$_2$Cl$_2$ (3×). The combined organic fractions were washed with brine, dried over MgSO$_4$, filtered, and concentrated. The crude residue was purified by column chromatography (silica, 0→100% EtOAc/hexanes) to give the desired compound (305 mg, 0.682 mmol, 63%). LCMS (Conditions A): $t_R$=4.5 min; (M+H)$^+$=448.

Step 4:

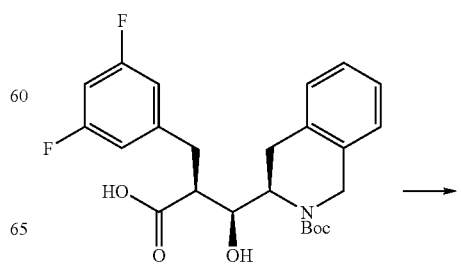

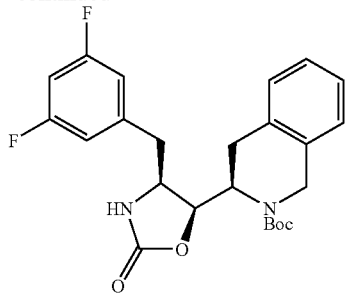

To a suspension of the product of Step 3 (305 mg, 0.682 mmol) in toluene (3.5 ml) was added Et₃N (0.19 ml, 140 mg, 1.4 mmol), followed by DPPA (0.18 ml, 225 mg, 0.82 mmol). The mixture became homogeneous. After five min, the mixture was heated to 80° C. in a pre-heated oil bath. After 4 h, the mixture was cooled to RT and concentrated directly without workup. This crude material was purified by column chromatography (silica, 0→100% EtOAc/hexanes) to give the desired product (300 mg, 0.68 mmol, 99%). LCMS (conditions A): $t_R$=4.9 min; (M+H)⁺=445.
Step 5:

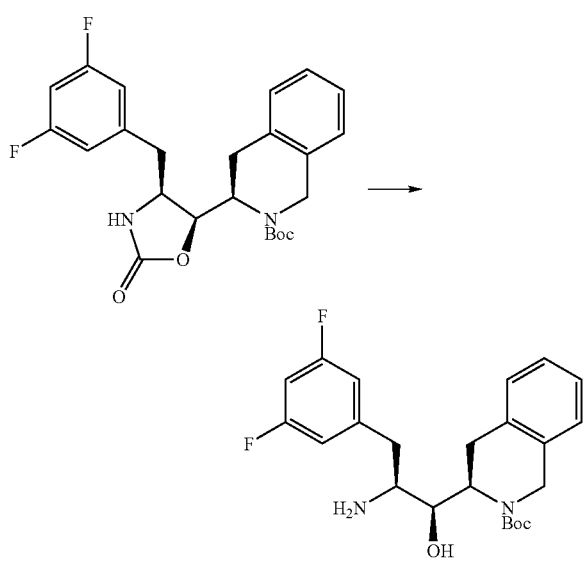

To a solution of the product of Step 4 (180 mg, 0.405 mmol) in ethanol (2 ml) was added 1 N aq. LiOH (2.0 ml, 2.0 mmol) The resulting mixture was heated to 85° C. After 4 h, the reaction mixture was cooled to RT and diluted with water and EtOAc. The phases were separated and the aqueous fraction was extracted with EtOAc (4×). The organic portions were combined, washed with brine, dried (MgSO₄), filtered, and concentrated. The crude residue was purified by HPLC (Conditions B) to give the product (138 mg, 0.297 mmol, 73%). LCMS (Conditions A): $t_R$=4.6 min; (M+H)⁺=419.
Step 6:

Reaction of the product of Step 5 (26 mg, 0.056 mmol) with Preparation 3A (13 mg, 0.059 mmol) by essentially the procedure set forth in Example 1D, Step 1, except that DMF was used in place of CH₂Cl₂, afforded the crude coupled product. The crude product was purified by HPLC (Conditions B) to give the desired couple product (17 mg, 0.028 mmol, 49%), as a 1:1 mixture of diastereomers. To a solution of the above material (14 mg, 0.023 mmol) in CH₂Cl₂ (1 ml) was added 4 N HCl/dioxane (1 ml). After 2 h, the reaction mixture was concentrated. This crude residue was purified by HPLC (Conditions C) to give the desired compound, a 1:1 mixture of diastereomers. LCMS (Conditions A): $t_R$=4.0 min; (M+H)⁺=514; ¹H NMR (CD₃OD, 300 MHz) δ 7.23 (m, 8 H), 6.90 (m, 4 H), 6.81 (m, 2 H), 4.52-4.24 (m, 6 H), 4.02 (br t, J=9.0 Hz, 2 H), 3.54 (m, 2 H), 3.38 (m, 3 H), 3.32-3.05 (m, 9 H), 2.67 (m, 5 H), 2.54 (m, 1 H), 2.28 (dt, $J_d$=4.8 Hz, $J_t$=7.2 Hz, 1 H), 1.61 (m, 1 H), 1.48-1.33 (m, 6 H), 1.30-1.14 (m, 6 H), 0.92 (t, J=7.2 Hz, 3 H), 0.85 (t, J=7.2 Hz, 3 H), 0.68 (t, J=7.5 Hz, 3 H), 0.55 (t, J=7.5 Hz, 3 H).

Example 2B

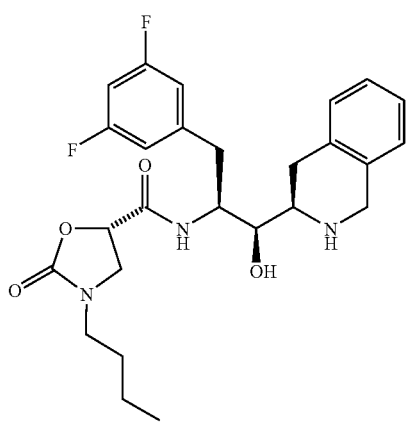

Using Preparation 4 and the compound of Example 2A, Step 5, the above compound was prepared. ¹H NMR (CD₃OD, 300 MHz) δ 7.22 (m, 4 H), 6.88-6.76 (m, 3 H), 4.80 (dd, J=9.9, 5.7 Hz, 1 H), 4.48 (d, J=15.6 Hz, 1 H), 4.31 (m, 2 H), 4.07 (br d, J=10.5 Hz, 1 H), 3.68 (m, 2 H), 3.39 (dd, J=13.8, 3.0 Hz, 1 H), 3.26-3.02 (m, 4 H), 2.72 (dd, J=13.8, 11.1 Hz, 1 H), 1.42 (m, 2 H), 1.26 (m, 2 H), 0.92 (t, J=7.2 Hz). MS m/e 488 (M+H)⁺.

Using the procedures set forth in Example 2A, Steps 1-6, substituting N-Boc-D-pipecolic acid for N-Boc-D-1,2,3,4-tetrahydroisoquinoline-3-carboxylic acid, the following examples were obtained.

Example 3A

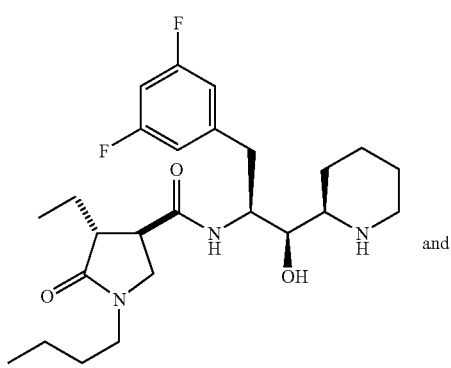

and

-continued

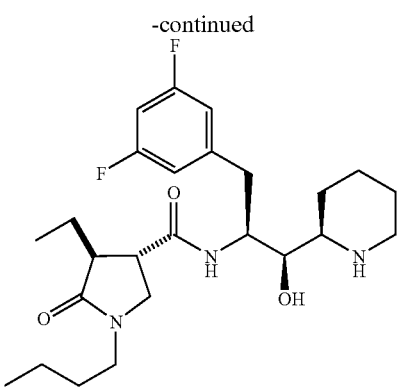

Isomer 1; ¹H NMR (CDCl₃, 400 MHz) δ 8.20 (m, 1H), 6.80 (m, 3H), 4.10 (m, 1H), 3.69 (m, 1H), 3.48 (m, 1H), 3.40-2.95 (m, 6H), 2.62 (m, 2H), 2.32 (m, 1H), 2.15-1.20 (m, 13H), 0.87 (m, 3H), 0.70 (m, 3H). MS m/e 466 (M+H)⁺. Isomer 2; ¹H NMR (CDCl₃) δ 8.22 (m, 1H), 6.81 (m, 3H), 4.10 (m, 1H), 3.70 (m, 1H), 3.40-2.90 (m, 7H), 2.80-2.50 (m, 4H), 2.10-1.15 (m, 12H), 0.88 (m, 6H). MS m/e 466 (M+H)⁺.

Example 3B

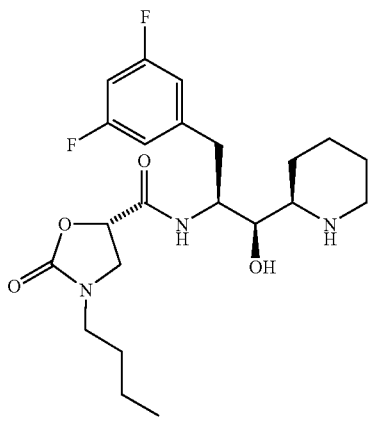

¹H NMR (CDCl₃, 400 MHz) δ 8.15 (m, 1H), 6.79 (m, 3H), 4.83 (m, 2H), 4.12 (m, 1H), 3.72 (m, 2H), 3.38-2.95 (m, 6H), 2.63 (m, 1H), 2.10-1.20 (m, 10H), 0.92 (m, 3H). MS m/e 440 (M+H)⁺.

Example 4A

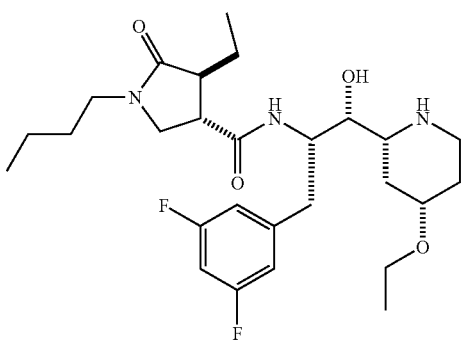

Step 1:

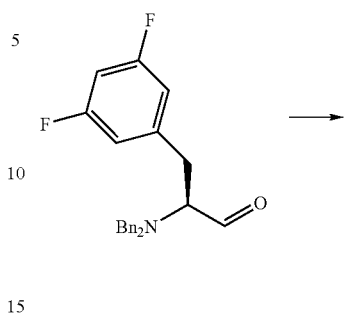

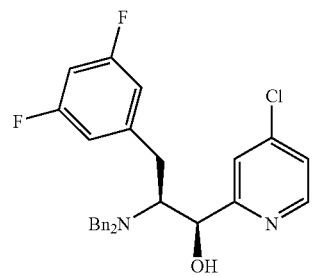

A solution of N,N-dimethylaminoethanol (2.60 ml, 26.2 mmol) in anhydrous hexane (50 ml) was cooled to −5° C. with stirring, to which nBuLi (2.5 M/hexane, 21.0 ml, 52.3 mmol) was added slowly. After the addition, the reaction mixture was warmed to 0° C. and stirred for 0.5 h. The reaction mixture was then cooled to −78° C., and 4-chloropyridine (3.00 g, 26.2 mmol) in anhydrous hexane (10 ml) was added slowly. The reaction mixture was stirred at −78° C. for 1.5 h, then a solution of Preparation 14 (7.97 g, 21.8 mmol) in anhydrous THF (20 ml) was added dropwise. After the addition, the reaction was allowed to warm to 0° C. and stirred at 0° C. for an additional 0.5 h. The reaction mixture was then poured into cold H₂O and extracted with CH₂Cl₂ (3×). The combined organic layers were dried over Na₂SO₄. The concentrated residue was purified by chromatography over silica gel (EtOAc/Hexane, 0%→25%) to afford the product as a light brown oil (4.45 g, 43%). ¹H NMR (CDCl₃, 400 MHz) δ 8.31 (d, J=2.8 Hz, 1H), 7.40-7.05 (m, 11H), 6.87 (d, J=16 Hz, 1H), 6.55 (m, 1H), 6.35 (m, 2H), 5.15 (s, br, 1H), 4.51 (s, br, 1H), 3.95 (d, J=14.0 Hz, 2H), 3.68 (d, J=14 Hz, 1H), 3.14 (m, 1H), 2.93 (m, 1H), 2.45 (m, 1H). MS (M+H)⁺=479 (M+H)⁺.

Step 2:

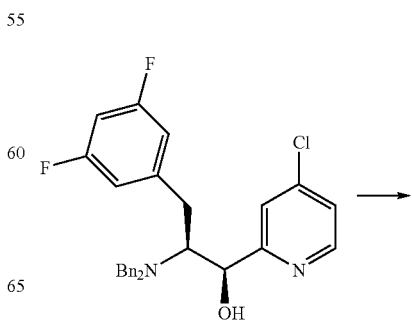

-continued

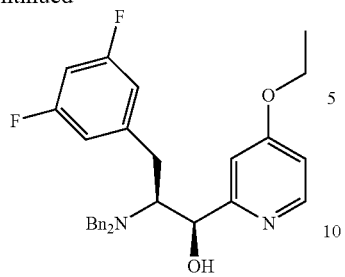

To a solution of the product of Step 1 (1.11 g, 2.32 mmol) in absolute ethanol (50 ml), sodium ethoxide (473 mg, 6.95 mmol) was added. The reaction mixture was heated to reflux for 3 h, then additional EtONa (315 mg, 4.63 mmol) was added. The mixture was refluxed for 19 h, then transferred to a glass pressure tube and additional EtONa (473 mg, 6.95 mmol) was added. The mixture was heated at 120° C. for 22 h and then 150° C. for 8 h. After the mixture had cooled to RT, it was poured to saturated $NH_4Cl$ and extracted with $CH_2Cl_2$ (3×). The combined organic layers were dried over $Na_2SO_4$. The concentrated residue was separated by PTLC (EtOAc/hexane, 1:4) to afford the product (0.75 g, 66%). $^1$H NMR ($CDCl_3$, 400 MHz) δ 8.21 (d, J=6.0 Hz, 1H), 7.40-7.05 (m, 10H), 6.62 (m, 1H), 6.58 (m, 1H), 6.31 (m, 2H), 6.20 (d, J=2.0 Hz, 1H), 5.19 (s, 1H), 4.06 (d, J=14.4 Hz, 2H), 3.90 (m, 1H), 3.78 (m, 1H), 3.69 (d, J=14.4 Hz, 2H), 3.10 (m, 1H), 2.92 (m, 1H), 2.35 (m, 1H), 1.35 (t, J=6.8, 3H). MS m/e 489 $(M+H)^+$.

Step 3:

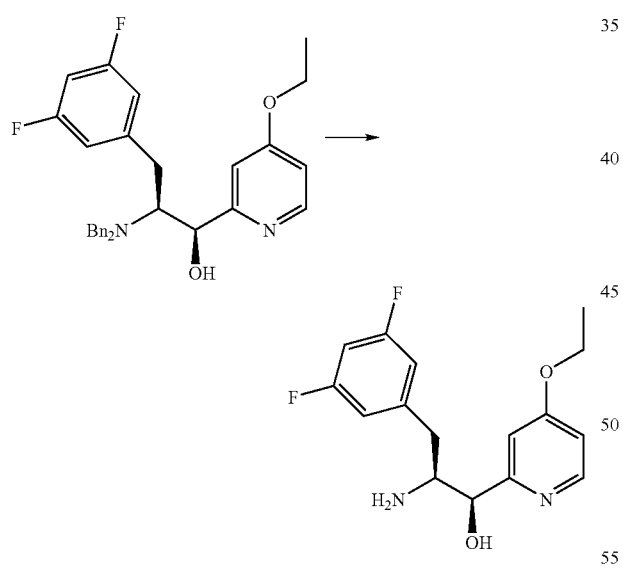

The product of Step 2 (161 mg, 0.330 mmol), 20% $Pd(OH)_2/C$ (161 mg), and AcOH (0.1 ml) in MeOH (10 ml) was stirred under 1 atm $H_2$ for 3 h at RT then filtered through celite. The concentrated residue was separated by PTLC (7M $NH_3$/MeOH: $CH_2Cl_2$, 1:10) to give the product (73.2 mg, 72%). $^1$H NMR ($CDCl_3$, 400 MHz) δ 8.30 (d, J=5.6 Hz, 1H), 6.84 (d, J=2.8 Hz, 1H), 6.69 (m, 1H), 6.63 (m, 2H), 6.58 (m, 1H), 4.66 (d, 1H), 4.05 (q, J=6.8 Hz, 2H), 3.38 (m, 1H), 2.63 (m, 1H), 2.38 (m, 1H), 1.40 (t, J=7.2 Hz, 3H). MS m/e 309 $(M+H)^+$.

Step 4:

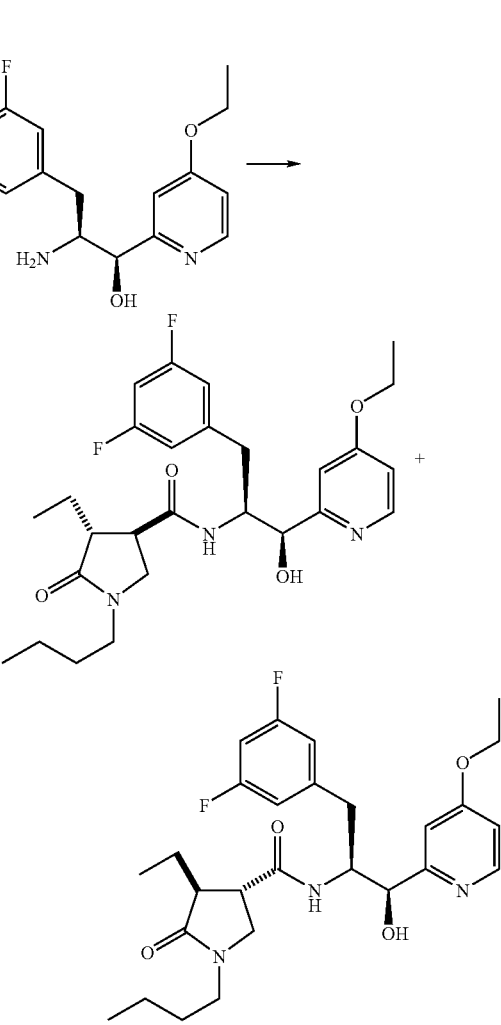

Reaction of the product of Step 3 with Preparation 3A by essentially the procedure set forth in Example 1D, Step 1 gave the separated diastereomeric products.

Isomer 1 (higher Rf): $^1$H NMR ($CDCl_3$, 400 MHz) δ 8.28 (d, J=5.6 Hz, 1H), 6.74 (s, 1H), 6.70 (m, 1H), 7.51 (m, 3H), 6.35 (m, 1H), 4.81 (d, J=2.8 Hz, 1H), 4.54 (m, 1H), 4.02 (m, 2H), 3.37 (m, 2H), 3.21 (m, 2H), 2.70-2.45 (m, 3H), 2.39 (M, 1H), 1.59 (m, 1H), 1.50-1.20 (m, 8H), 0.87 (t, J=8.6 Hz, 3H), 0.73 (t, J=8.6 Hz). MS m/e 504 $(M+H)^+$.

Isomer 2 (lower Rf): $^1$H NMR ($CDCl_3$, 400 MHz) δ 8.29 (d, J=5.6 Hz, 1H), 6.73 (m, 2H), 6.52 (m, 3H), 6.31 (m, 1H), 4.79 (m, 1H), 4.55 (m, 1H), 4.02 (m, 2H), 3.30-3.05 (m, 4H), 2.75-2.50 (m, 3H), 2.41 (m, 1H), 1.81 (m, 1H), 1.70-1.20 (m, 8H), 0.89 (m, 6H). MS m/e 504 $(M+H)^+$.

Step 5

A mixture of the product of Step 4 (Isomer 1, 17.0 mg, 0.034 mmol), $PtO_2$ (17.0 mg) and acetic acid (5 ml) was stirred under hydrogen balloon for 24 h and filtered through celite. The concentrated residue was separated by HPLC(C-18, 25 ml/min, 10→95% $MeCN/H_2O$ with 0.1% $HCO_2H$) to afford the product as a formate salt. LCMS (conditions A) $t_R$=2.71 min, m/e 510 $(M+H)^+$.

Using the appropriate starting materials and essentially the same procedure the following compounds were prepared:

| Example | Preparation | Structure | LCMS (conditions A) |
|---|---|---|---|
| 4B | 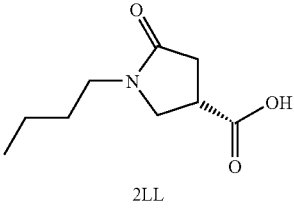<br>2LL | 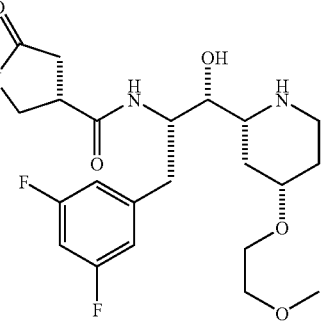 | $t_R$ = 2.63 min<br>m/e = 512<br>$(M + H)^+$ |
| 4C | 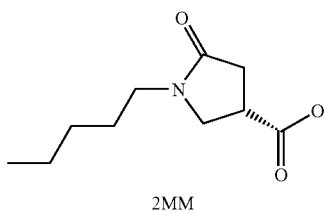<br>2MM | 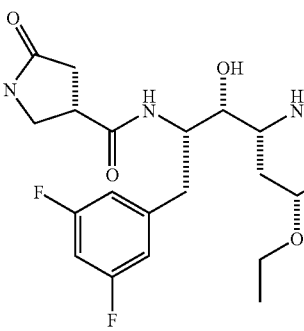 | $t_R$ = 3.02 min<br>m/e = 496<br>$(M + H)^+$ |

Example 5A

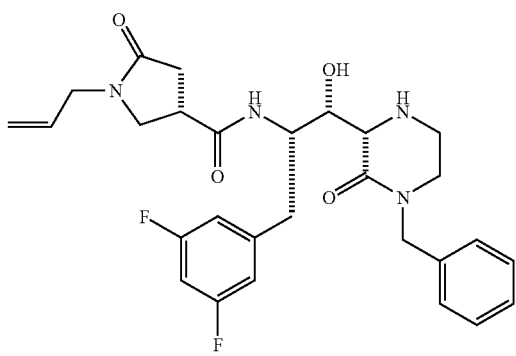

Step 1:

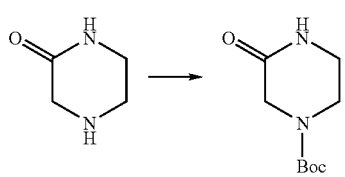

Piperazin-2-one (1 g, 10 mmol) was dissolved in $CH_2Cl_2$ (40 ml), and $Boc_2O$ (2.4 g, 11 mmol, 1.1 eq), $Et_3N$ (2.02 g, 20 mmol, 2 eq) and DMAP (0.024 g, 0.2 mmol, 2 mol %) were added. After the mixture was stirred at RT for 16 h, it was acidified with 1N HCl. The organic layer was separated, washed with saturated $NaHCO_3$, brine, dried ($Na_2SO_4$), and concentrated in vacuo to give the product (1.8 g, 90%) as a white solid. $^1$H NMR ($CDCl_3$, 300 MHz) δ 6.70 (1H, bs), 4.08 (2H, s), 3.62 (2H, t, J=6.0 Hz), 3.37 (2H, m), 1.46 (9H, s).

Step 2:

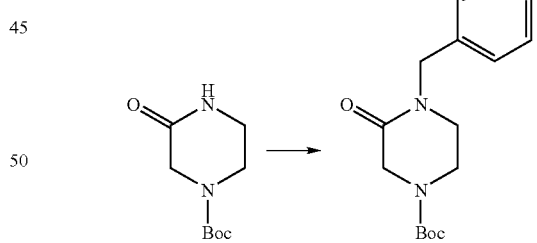

To a solution of the product of Step 1 (1.17 g, 5.87 mmol) in DMF (25 ml) at RT was added NaH (60% dispersion in mineral oil, 352 mg, 8.8 mmol, 1.5 eq) and the resulting mixture was stirred at RT for 2 h. Benzyl bromide (0.84 ml, 7.04 mmol, 1.2 eq) was added and the reaction was heated at 70° C. for 16 h. The reaction mixture was cooled to RT and the excess NaH was quenched carefully by the dropwise addition of MeOH. The solvent was evaporated in vacuo and the residue was chromatographed ($SiO_2$, 70% EtOAc/hexanes) to give the product (1.6 g, 95%) as a white solid. $^1$H NMR ($CDCl_3$, 300 MHz) δ 7.28 (5H, m), 4.62 (2H, s), 4.16 (2H, s), 3.58 (2H, m, J=5.1 Hz), 3.25 (2H, m, J=5.4 Hz), 1.46 (9H, s).

Step 3:

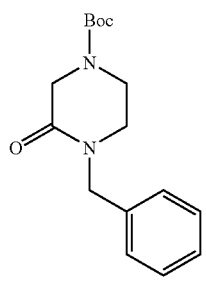

To a solution of diisopropylamine (3.712 g, 36.68 mmol) in anhydrous THF (20 ml) at −78° C. was added 2.5 M BuLi in hexanes (14.2 ml, 35.5 mmol). After 5 min, the solution was placed in an ice-water bath and stirred for 30 min. The mixture was cooled to −78° C. again and a solution of the product of Step 2 (8.875 g, 30.57 mmol) in THF (30 ml) was added and the mixture was stirred for 1.5 h at −78° C. A solution of Preparation 14 (12.1 g, 33.11 mmol) in THF (20 ml) was added and the resulting mixture was allowed to warm to RT overnight. The mixture was partitioned between ether (150 ml) and water (200 ml). The aqueous layer was extracted with ether (3×150 ml). The combined organic layers were dried (MgSO$_4$), concentrated, and purified by column chromatography (SiO$_2$, gradient 0-20% EtOAc/Hexanes) to give a light yellow solid (9.00 g, 41%). MS m/e 656 (M+H)$^+$.

Step 4:

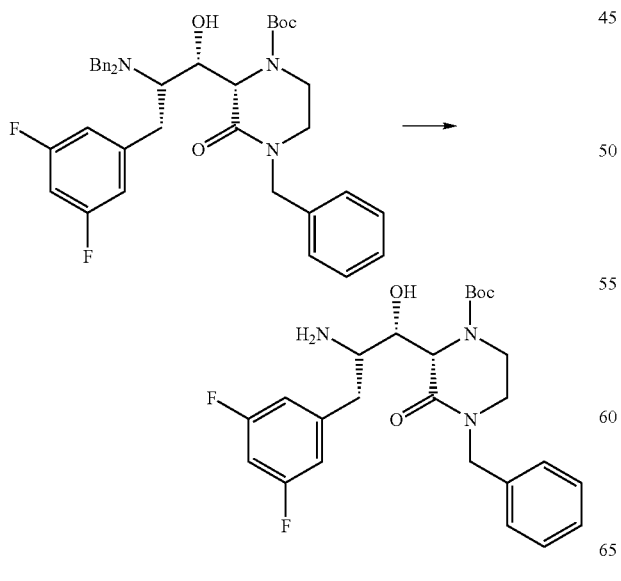

A mixture of the product of Step 3 (495 mg, 0.755 mmol), 20% Pd(OH)$_2$/C (493 mg), and a catalytic amount of acetic acid in EtOH (15 ml) was stirred under H$_2$ (1 atm) for 5 h at RT. The mixture was filtered through a pad of Celite and concentrated. The residue was dissolved in CH$_2$Cl$_2$ (50 ml) and washed with aq. NH$_4$OH (15 ml). The organic layer was dried (MgSO$_4$) and concentrated to give the product (326 mg, 91%). MS m/e 476 (M+H)$^+$.

Step 5:

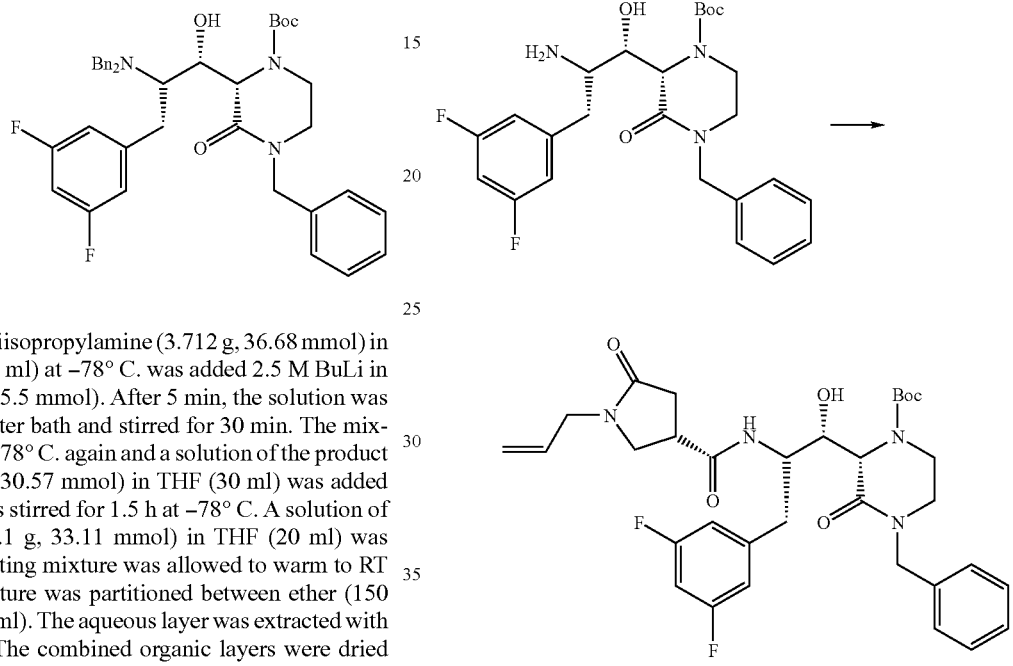

A mixture of the product of Step 4 (56 mg, 0.12 mmol), Preparation 2JJ (24 mg, 0.14 mmol), HOBt (19 mg, 0.14 mmol), EDCl (54 mg, 0.28 mmol), and triethylamine (57 mg, 0.57 mmol) in CH$_2$Cl$_2$ (5 ml) was stirred at RT for 17 h. The mixture was diluted with CH$_2$Cl$_2$ (50 ml), washed with 5% citric acid and saturated sodium bicarbonate, dried (MgSO$_4$), concentrated, and purified by PTLC (5% MeOH/CH$_2$Cl$_2$) to give the product (65 mg, 86%). MS m/e 627 (M+H)$^+$.

Step 6:

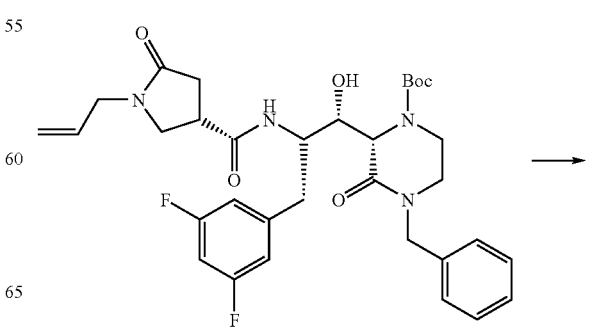

-continued

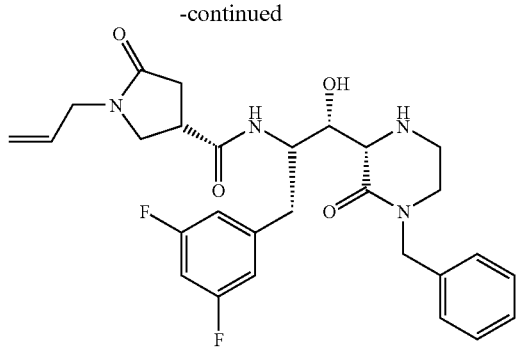

A solution of the product of Step 5 (15 mg, 0.024 mmol) and TFA (0.4 ml) in CH$_2$Cl$_2$ (3 ml) was stirred at RT for 1.5 h. The mixture was concentrated and purified by PTLC (5% 2M NH$_3$/MeOH-95% CH$_2$Cl$_2$) to give the product (11 mg, 89%). $^1$H NMR (CDCl$_3$) δ 7.15-7.35 (m, 5H), 6.72 (m, 2H), 6.61 (m, 1H), 6.42 (b, 1H), 5.64 (m, 1H), 5.31 (b, 1H), 5.14 (m, 2H), 4.62 (d, 1H, J=14.8 Hz), 4.51 (m, 2H), 4.03 (m, 1H), 3.80 (m, 2H), 3.50 (m, 1H), 3.37 (m, 3H), 3.15 (m, 2H), 3.02 (m, 1H), 2.92 (m, 3H), 2.39 (m, 2H). LCMS (Conditions A): t$_R$=2.74 min; m/e 527 (M+H)$^+$.

| Ex. | Preparation | Example | LCMS (conditions A) |
|---|---|---|---|
| 5B | 2KK | | t$_R$ = 2.48 min<br>m/e = 515<br>(M + H)+ |
| 5C | 2LL | | t$_R$ = 3.11 min<br>m/e = 543<br>(M + H)+ |
| 5D | 2MM | | t$_R$ = 3.35 min<br>m/e = 557<br>(M + H)+ |

| Ex. | Preparation | Example | LCMS (conditions A) |
|---|---|---|---|
| 5E | 2NN | | $t_R$ = 3.51 min<br>m/e = 571<br>(M + H)+ |
| 5F | 2C | | $t_R$ = 2.92 min<br>m/e = 529<br>(M + H)$^+$<br>$t_R$ = 2.90 min<br>m/e = 529<br>(M + H)$^+$ |
| 5G | 2FF | | $t_R$ = 3.06 min;<br>543 (M + H)$^+$<br>$t_R$ = 3.05 min;<br>543 (M + H)$^+$ |
| 5H | 2GG | | $t_R$ = 3.06 min;<br>543 (M + H)$^+$<br>$t_R$ = 3.08 min;<br>543 (M + H)$^+$ |

-continued

| Ex. | Preparation | Example | LCMS (conditions A) |
|---|---|---|---|
| 5I | 2E | | $t_R$ = 3.35 min; 557 (M + H)$^+$ $t_R$ = 3.37 min; 557 (M + H)$^+$ |
| 5J | 2F | | $t_R$ = 3.51 min; 571 (M + H)$^+$ $t_R$ = 3.55 min; 571 (M + H)$^+$ |
| 5K | 2I | | $t_R$ = 3.01 min; 541 (M + H)$^+$ $t_R$ = 3.03 min; 541 (M + H)$^+$ |

| Ex. | Preparation | Example | LCMS (conditions A) |
|---|---|---|---|
| 5L | 2II | | $t_R$ = 2.70 min; 545 (M + H)$^+$ $t_R$ = 2.72 min; 545 (M + H)$^+$ |
| 5M | 2O | | $t_R$ = 3.65 min; 585 (M + H)$^+$ $t_R$ = 3.64 min; 585 (M + H)$^+$ |
| 5N | 2P | | $t_R$ = 3.28 min; 557 (M + H)$^+$ $t_R$ = 3.27 min; 557 (M + H)$^+$ |

| Ex. | Preparation | Example | LCMS (conditions A) |
|---|---|---|---|
| 5O | 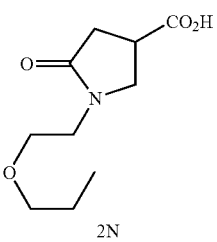<br>2N | 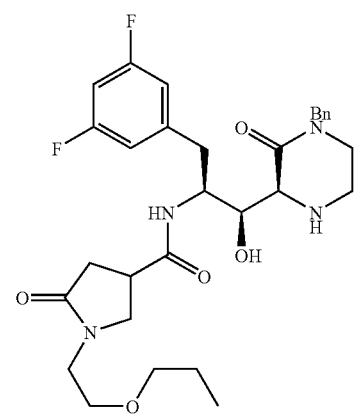 | $t_R$ = 3.07 min; 573 (M + H)$^+$<br>$t_R$ = 3.08 min; 573 (M + H)$^+$ |
| 5P | 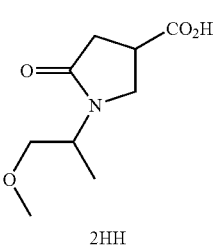<br>2HH | 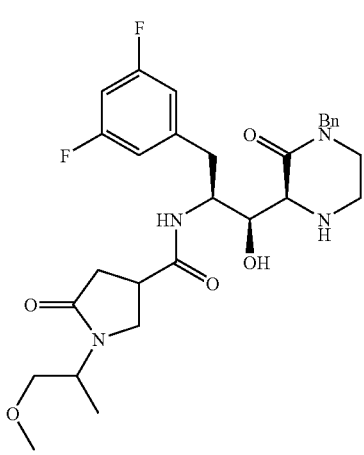 | $t_R$ = 2.85 min; 559 (M + H)$^+$<br>$t_R$ = 2.85 min; 559 (M + H)$^+$ |
| 5Q | 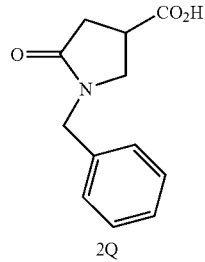<br>2Q | 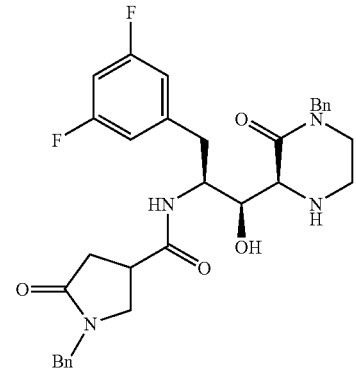 | $t_R$ = 3.26 min; 577 (M + H)$^+$<br>$t_R$ = 2.97 min; 577 (M + H)$^+$ |

-continued
| Ex. | Preparation | Example | LCMS (conditions A) |
|---|---|---|---|
| 5R | 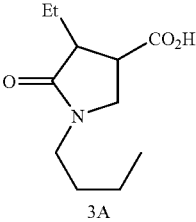<br>3A | 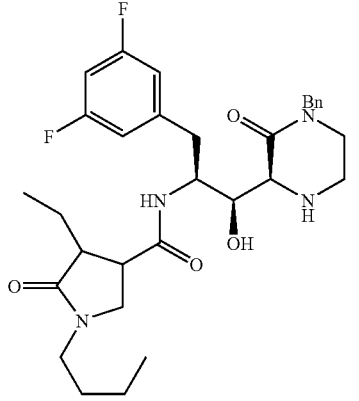 | $t_R$ = 3.35 min;<br>571 (M + H)$^+$<br>$t_R$ = 3.36 min;<br>571 (M + H)$^+$ |
| 5S | 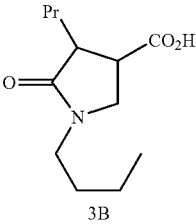<br>3B | 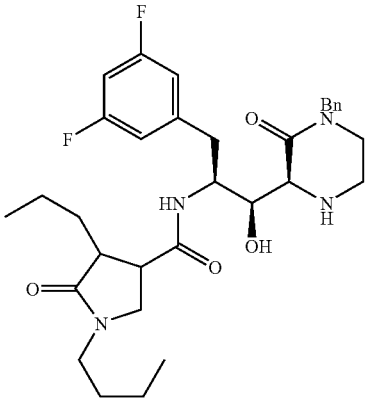 | $t_R$ = 3.34 min;<br>585 (M + H)$^+$ |
| 5T | 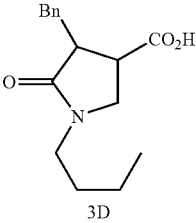<br>3D | 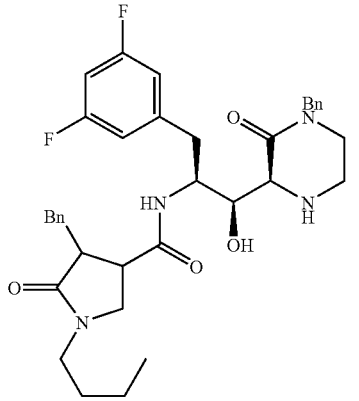 | $t_R$ = 3.74 min;<br>633 (M + H)$^+$ |

-continued
| Ex. | Preparation | Example | LCMS (conditions A) |
|---|---|---|---|
| 5U | 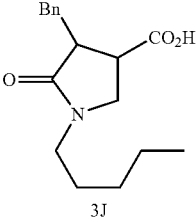 3J | 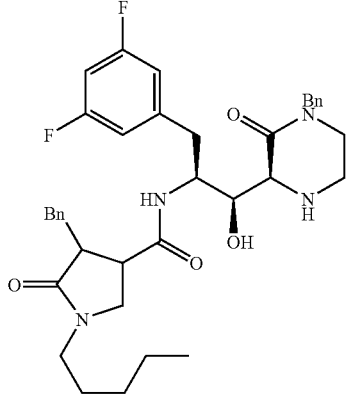 | $t_R$ = 3.91 min; 647 (M + H)$^+$ |
| 5V | 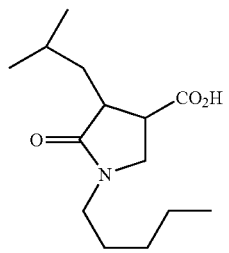 3E | 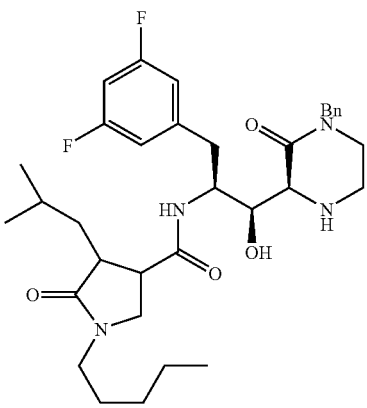 | $t_R$ = 3.81 min; 613 (M + H)$^+$ |
| 5W | 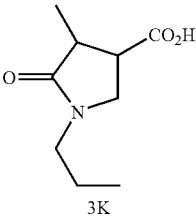 3K | 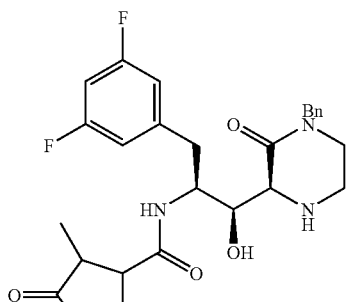 | $t_R$ = 2.72 min; 543 (M + H)$^+$ $t_R$ = 2.71 min; 543 (M + H)$^+$ |
| 5X | 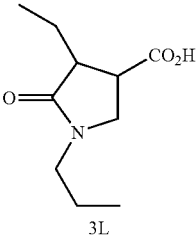 3L | 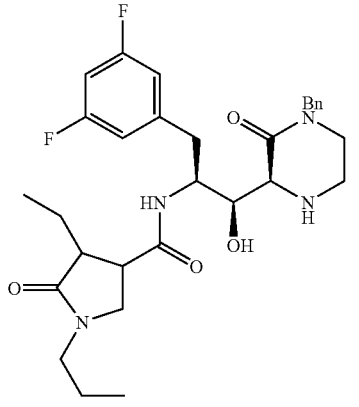 | $t_R$ = 2.84 min; 557 (M + H)$^+$ |

-continued
| Ex. | Preparation | Example | LCMS (conditions A) |
|---|---|---|---|
| 5Y | 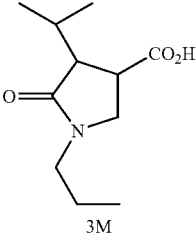<br>3M | 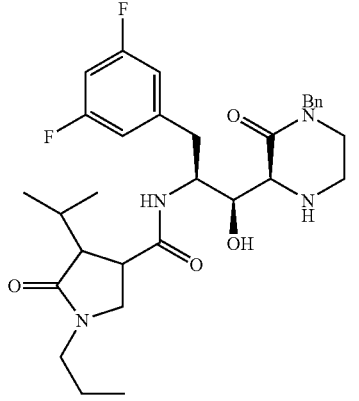 | $t_R$ = 2.98 min;<br>571 (M + H)$^+$<br>$t_R$ = 2.97 min;<br>571 (M + H)$^+$ |
| 5Z | 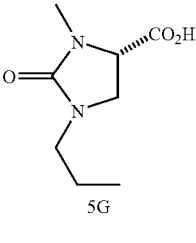<br>5G | 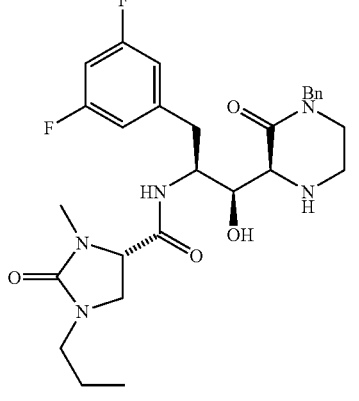 | $t_R$ = 3.07 min;<br>544 (M + H)$^+$ |
| 5AA | 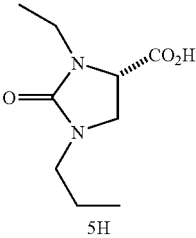<br>5H | 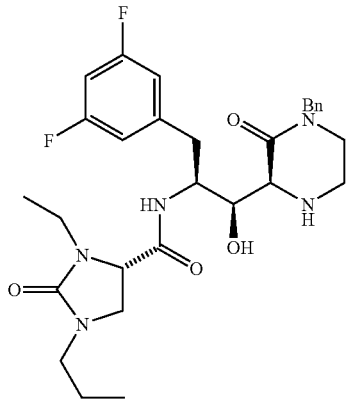 | $t_R$ = 2.83 min;<br>558 (M + H)$^+$ |

| Ex. | Preparation | Example | LCMS (conditions A) |
|---|---|---|---|
| 5BB | 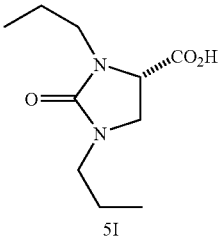<br>5I | 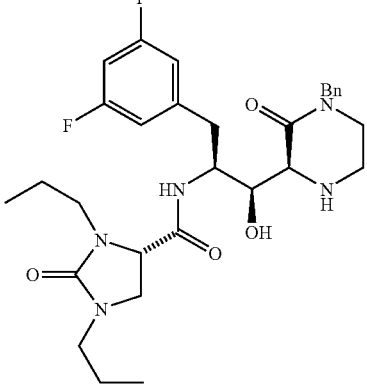 | $t_R$ = 2.94 min;<br>572 (M + H)$^+$ |
| 5CC | 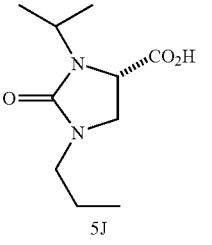<br>5J | 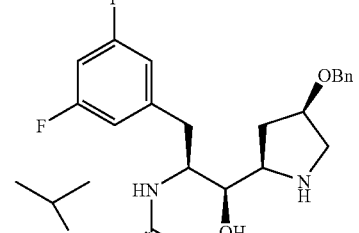 | $t_R$ = 3.20 min;<br>572 (M + H)$^+$ |
| 5DD | 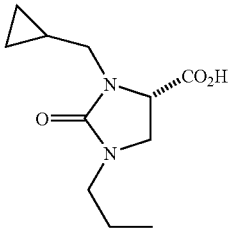<br>5K | 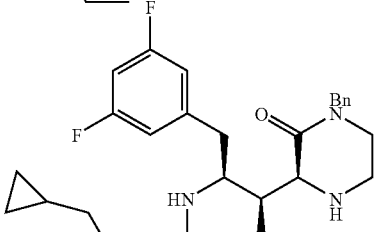 | $t_R$ = 3.33 min;<br>584 (M + H)$^+$ |
| 5EE | 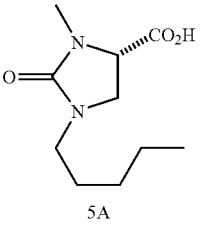<br>5A | 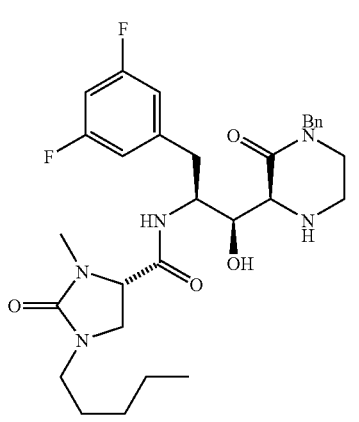 | $t_R$ = 3.10 min;<br>572 (M + H)$^+$ |

-continued
| Ex. | Preparation | Example | LCMS (conditions A) |
|---|---|---|---|
| 5FF | 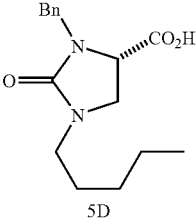 5D | 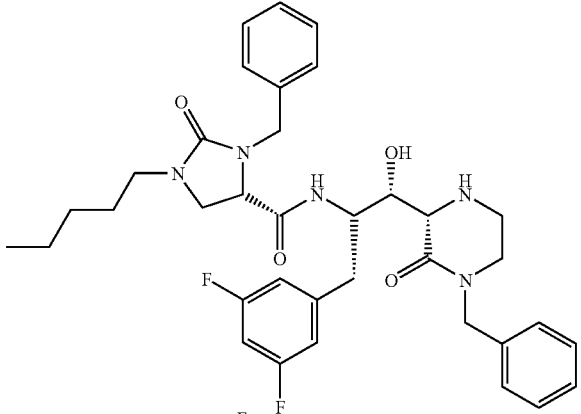 | $t_R$ = 3.91 min; m/e = 648 |
| 5GG | 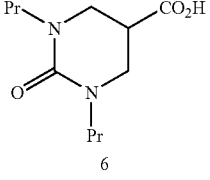 6 | 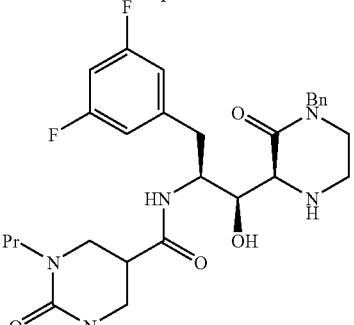 | $t_R$ = 3.20 min; 586 (M + H)$^+$ |
| 5HH | 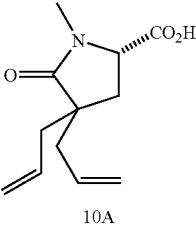 10A | 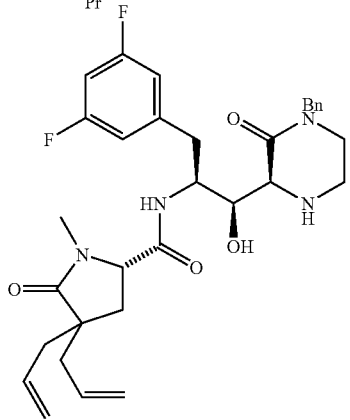 | $t_R$ = 3.12 min; 581 (M + H)$^+$ |
| 5II | 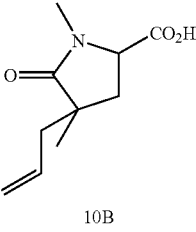 10B | 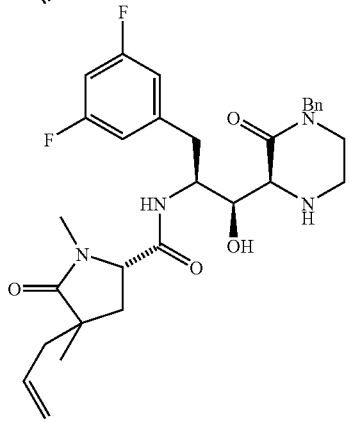 | $t_R$ = 2.85 min; 555 (M + H)$^+$ |

| Ex. | Preparation | Example | LCMS (conditions A) |
|---|---|---|---|
| 5JJ | 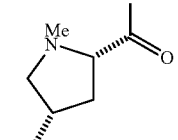 11 | 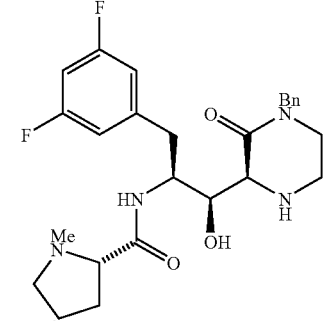 | $t_R$ = 2.58 min: 545 (M + H)$^+$ |
| 5KK | 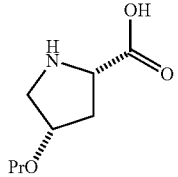 11 | 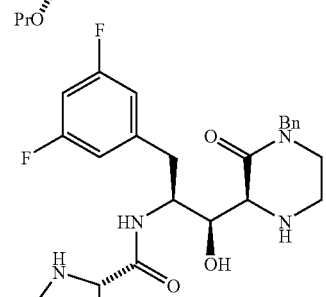 | $t_R$ = 2.08 min: 531 (M + H)$^+$ |
Example 5LL
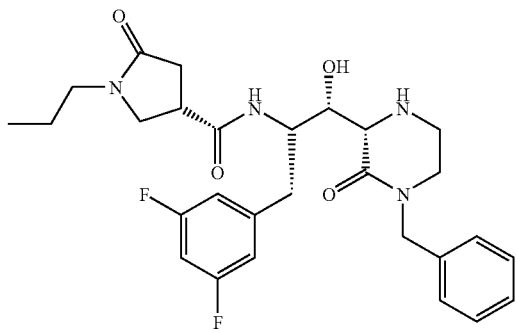
Step 1:
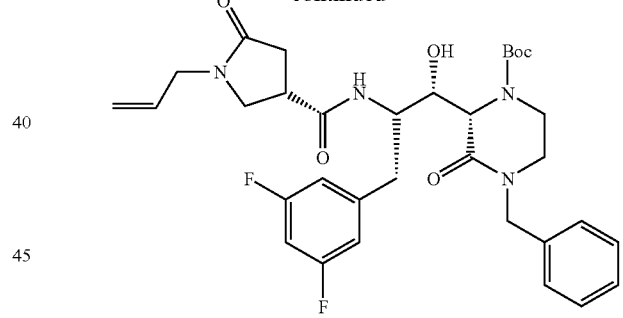
A mixture of the product of Example 5A, Step 4 (56 mg, 0.12 mmol), Preparation 2JJ (24 mg, 0.14 mmol), were coupled in analogy to the procedure of Example 5A, Step 5. The crude product was purified by PTLC (5% MeOH/CH$_2$Cl$_2$) to give the product (65 mg, 86%). MS m/e 627 (M+H)$^+$.
Step 2:
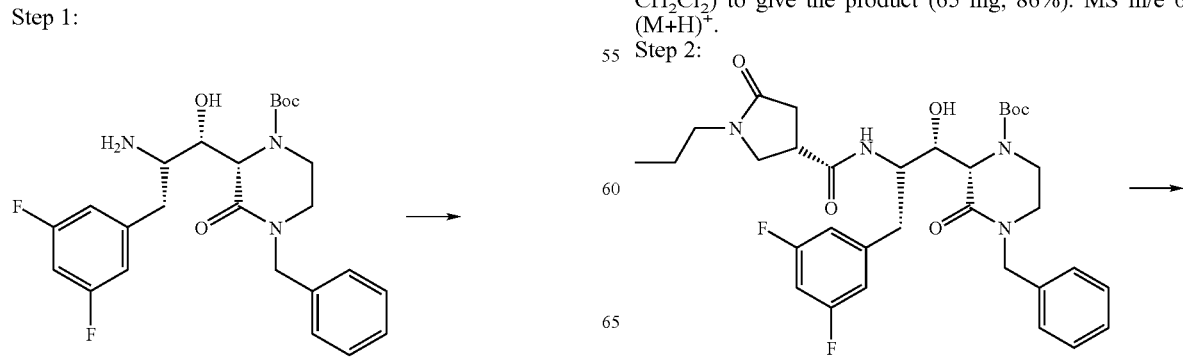

-continued

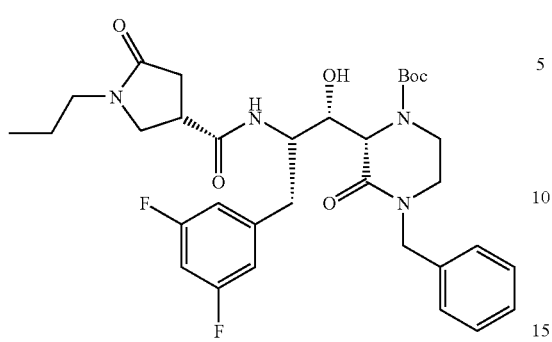

A mixture of the product of Step 1 (50 mg, 0.080 mmol) and 10% Pd/C (20 mg) in EtOH (5 ml) was stirred under H$_2$ (1 atm) for 4 h. The mixture was filtered and concentrated to give the product (46 mg, 91%).

Step 3:

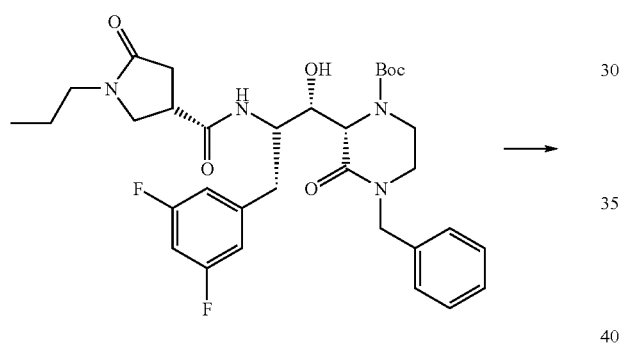

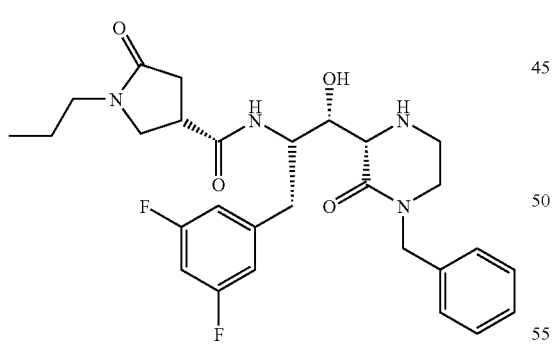

A solution of the product of Step 2 (46 mg, 0.073 mmol) and TFA (1 ml) in CH$_2$Cl$_2$ (4 ml) was stirred at RT for 1 h. The mixture was concentrated and purified by PTLC (8% 2M NH$_3$/MeOH—CH$_2$Cl$_2$) to give the product (24 mg, 62%). $^1$H NMR (CDCl$_3$) δ 7.15-7.35 (m, 5H), 6.72 (m, 2H), 6.60 (m, 1H), 6.37 (m, 1H), 4.62 (m, 1H), 4.49 (m, 2H), 3.94 (m, 1H), 2.7-3.5 (m, 12H), 2.34 (m, 2H), 1.44 (m, 3H), 0.83 (t, 3H, J=7.2 Hz). LCMS (Conditions A): t$_R$=2.64 min; m/e 529 (M+H)$^+$.

Example 5MM

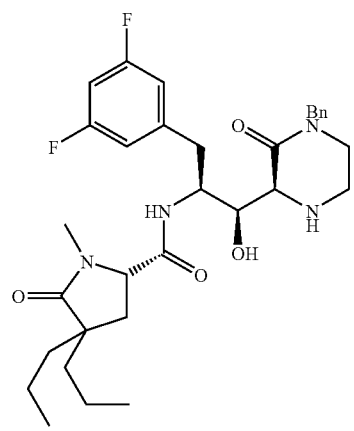

A suspension of Example 5HH (26 mg, 0.045 mmol) and Pd(OH)$_2$/C (40 mg) in MeOH (8 ml) was stirred under H$_2$ for 1.5 h. The reaction mixture was filtered and the filtrate was evaporated. PTLC of the residue gave the product (22 mg, 88%). LCMS (Conditions A) t$_R$=3.54 min; 585 (M+H)$^+$.

Example 5NN

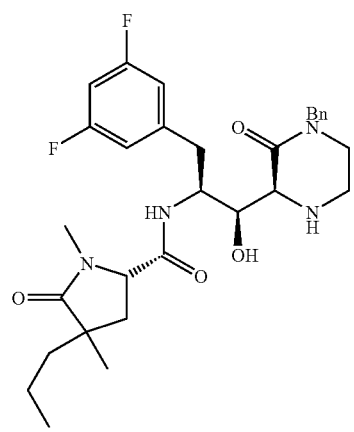

Example 5NN was prepared from Example 5II in analogy to Example 5MM. LCMS (conditions A) t$_R$=3.26 min; 557 (M+H)$^+$.

Example 6

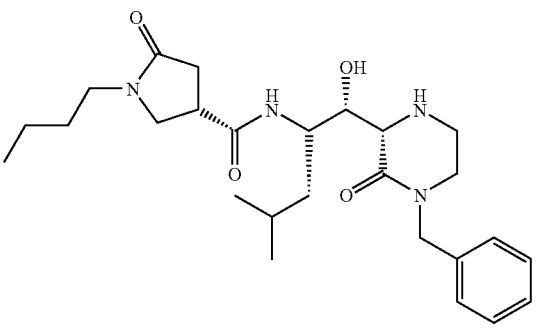

Preparation 15 was converted to the product in analogy to the procedure of Example 5A, except that Preparation 2LL was used in Step 5 in place of Preparation 2JJ. LCMS (conditions A) $t_R$=2.83 min; 473 (M+H)$^+$.

Example 7

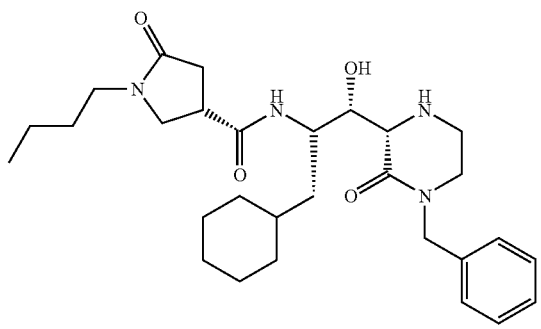

Preparation 16 was converted to the product in analogy to the procedure of Example 5A, except that Preparation 2LL was used in Step 5 in place of Preparation 2JJ. LCMS (conditions A) $t_R$=2.82 min; 513 (M+H)$^+$.

Example 8A

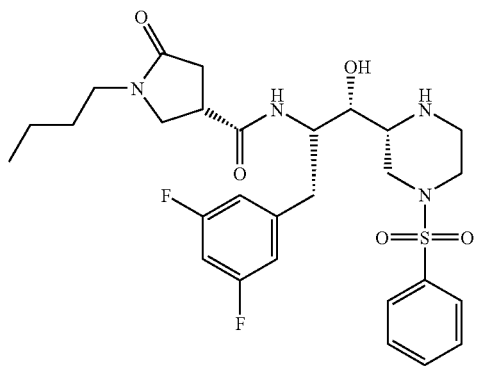

Step 1:

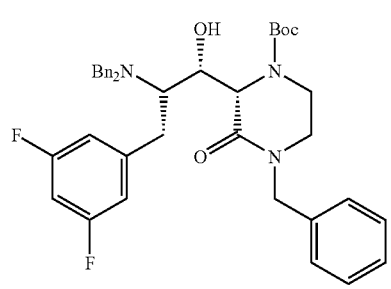

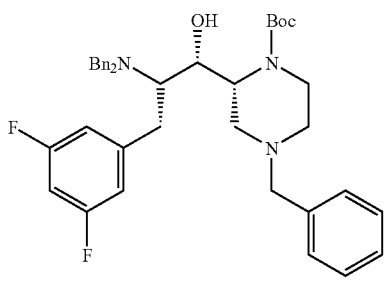

To a solution of the product of Example 5A, Step 3 (1.32 g, 2.01 mmol) in THF (27 ml) was added 2M BH$_3$—SMe$_2$ in THF (4.0 ml) and the mixture was heated to 60° C. for 2.5 h. The mixture was treated with saturated citric acid (25 ml) and extracted with EtOAc (3×40 ml). The combined organic layer was evaporated to dryness and the residue was partitioned between CH$_2$Cl$_2$ (100 ml) and aqueous NH$_4$OH (30 ml). The organic layer was dried (MgSO$_4$), concentrated, and purified by column chromatography (SiO$_2$, gradient EtOAc/hexanes 0-20%) to give the product (1.16 g, 90%). MS m/e 642 (M+H)$^+$.

Step 2:

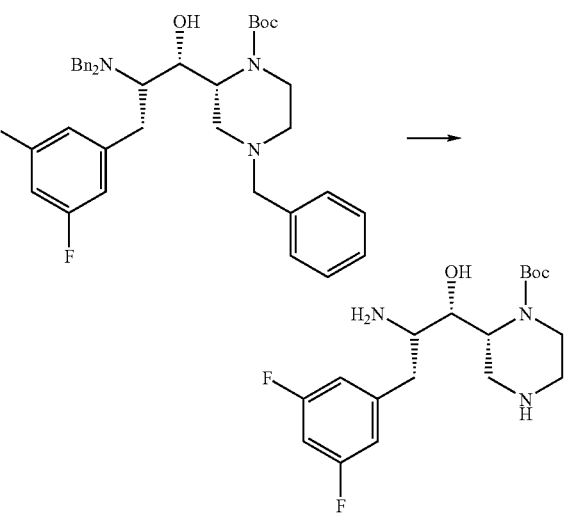

A mixture of the product of Step 1 (1.16 g, 1.81 mmol), 20% Pd(OH)$_2$/C (1.17 g), and catalytic amount of AcOH in EtOH (12 ml) was stirred under H$_2$ (1 atm) for 16 h. The mixture was filtered through a pad of Celite and concentrated. The residue was taken up in CH$_2$Cl$_2$ (40 ml) and washed with aqueous NH$_4$OH (20 ml). The organic layer was dried (MgSO$_4$) and concentrated to give the product (611 mg, 91%). MS m/e 372 (M+H)$^+$.

Step 3:

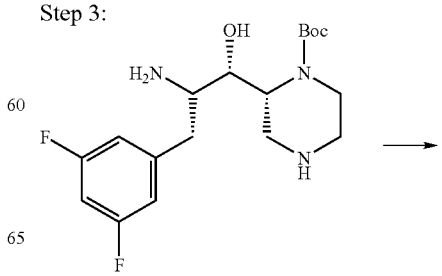

-continued

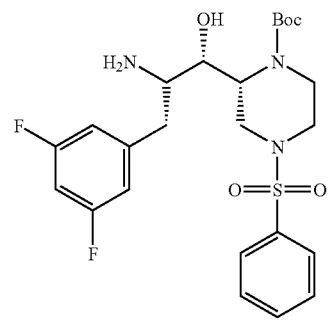

To a solution of the product of Step 2 (92 mg, 0.25 mmol) and Et₃N (35 μl, 0.25 mmol) in CH₂Cl₂ (5 ml) in an ice-water bath was added benzenesulfonyl chloride (43 mg, 0.25 mmol) in CH₂Cl₂ (3 ml) dropwise. The mixture was stirred in ice-water bath for 1.5 h, diluted with CH₂Cl₂ (40 ml), and washed with 1N NaOH (30 ml). The organic layer was dried (MgSO₄), concentrated, and purified by PTLC (5% MeOH/CH₂Cl₂) to give the product (106 mg, 84%). MS m/e 512 (M+H)⁺.

Step 4:

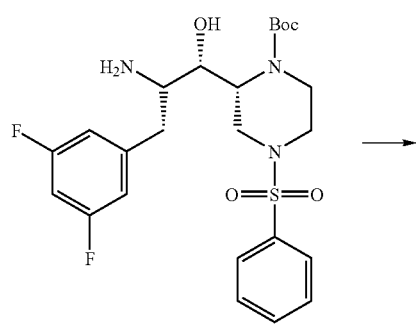

The product of Step 3 (106 mg, 0.207 mmol) and Preparation 2LL (43 mg, 0.23 mmol) were couple in analogy to the procedure of Example 5A Step 5. The crude product was purified by PTLC (3% MeOH/CH₂Cl₂) to give the product (52 mg, 37%). MS m/e 701 (M+Na)⁺.

Step 5:

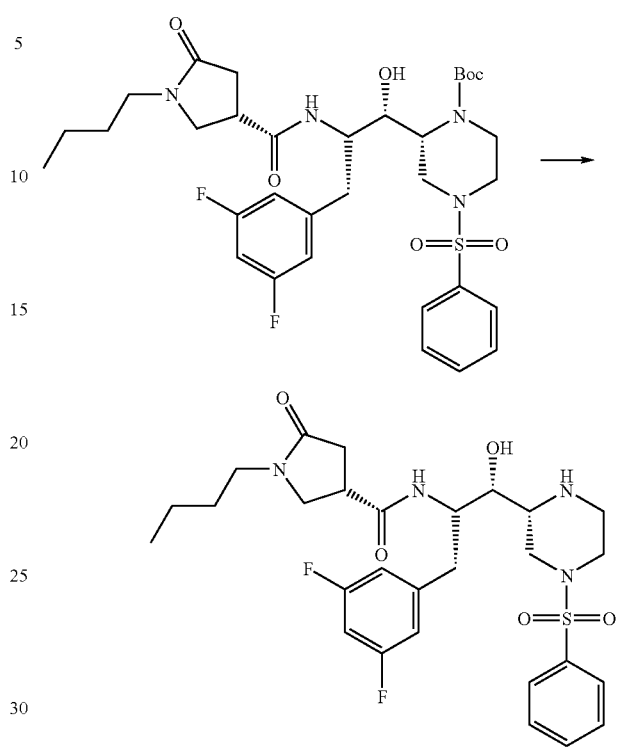

A mixture of the product of Step 4 (52 mg, 0.077 mmol) and TFA (0.9 ml) in CH₂Cl₂ (4 ml) was stirred in an ice-water bath for 30 min then at RT for 2 h. The mixture was diluted with CH₂Cl₂ (40 ml) and washed with aqueous NH₄OH (20 ml). The organic layer was dried (MgSO₄), concentrated, and purified by PTLC (5% MeOH/CH₂Cl₂) to give the product (37 mg, 83%). ¹H NMR (CDCl₃) δ 7.72 (m, 2H), 7.62 (m, 1H), 7.54 (m, 2H), 6.76 (m, 2H), 6.69 (d, 1H, J=8.8 Hz), 6.61 (m, 1H), 4.37 (m, 1H), 3.72 (m, 1H), 3.52 (m, 2H), 3.41 (m, 1H), 3.22 (m, 3H), 3.01 (m, 3H), 2.80 (m, 3H), 2.51 (m, 3H), 2.31 (m, 1H), 1.43 (m, 2H), 1.24 (m, 2H), 0.89 (m, 3H). LCMS (Conditions A): $t_R$=3.09 min; m/e 579 (M+H)⁺.

By essentially the same procedure set forth in Example 8A, the following example was prepared.

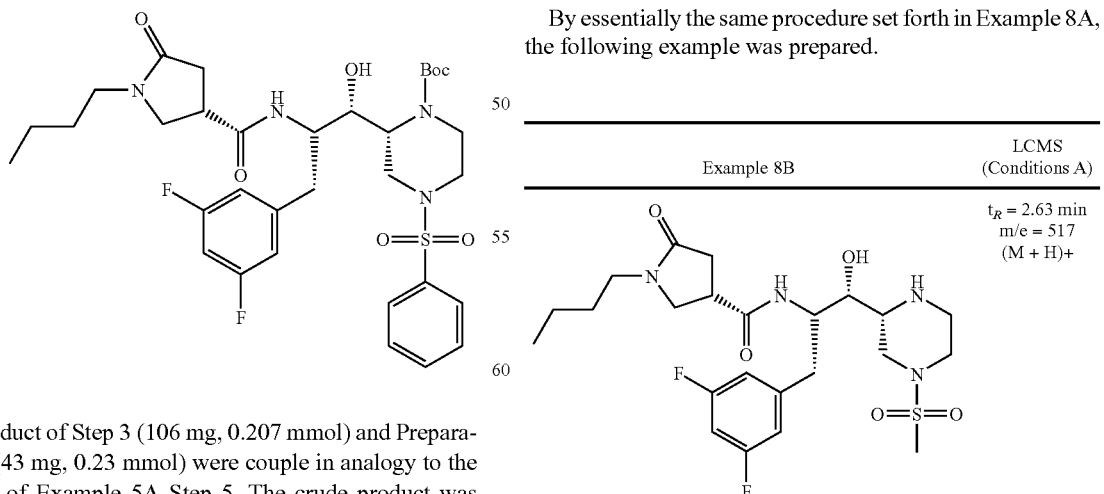

| Example 8B | LCMS (Conditions A) |
|---|---|
|  | $t_R$ = 2.63 min<br>m/e = 517<br>(M + H)+ |

Examples 8C-8III

The Examples in the Table below were prepared according to the following procedure:

Step 1:

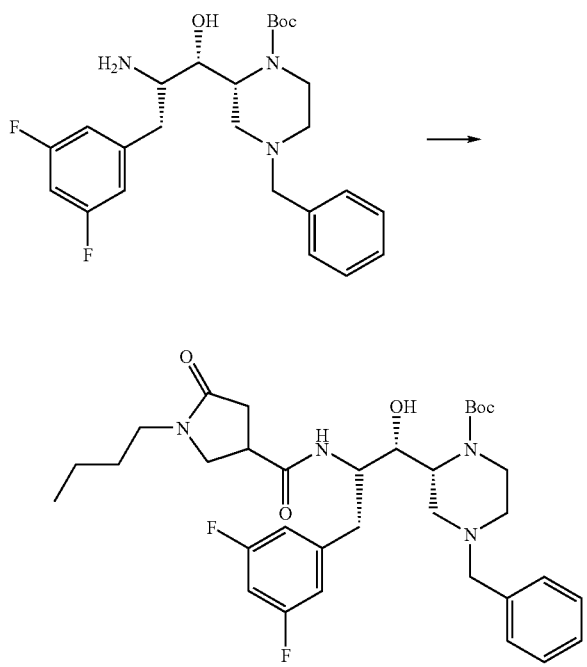

A mixture of the product of Example 10A, Step 1 (969 mg, 2.10 mmol), Preparation 2A (395 mg, 2.14 mmol), EDCl (403 mg, 2.10 mmol), HOBt (299 mg, 2.21 mmol), and triethylamine (297 mg, 2.93 mmol) in CH$_2$Cl$_2$ (25 ml) was stirred at RT for 16 h. The mixture was diluted with CH$_2$Cl$_2$ (50 ml) and washed with 1N NaOH (30 ml). The organic layer was dried (MgSO$_4$), concentrated, and purified by column chromatography (SiO$_2$, gradient MeOH/CH$_2$Cl$_2$ 0-3%) to give the product (1.25 g, 95%). MS m/e 629 (M+H)$^+$.

Step 2:

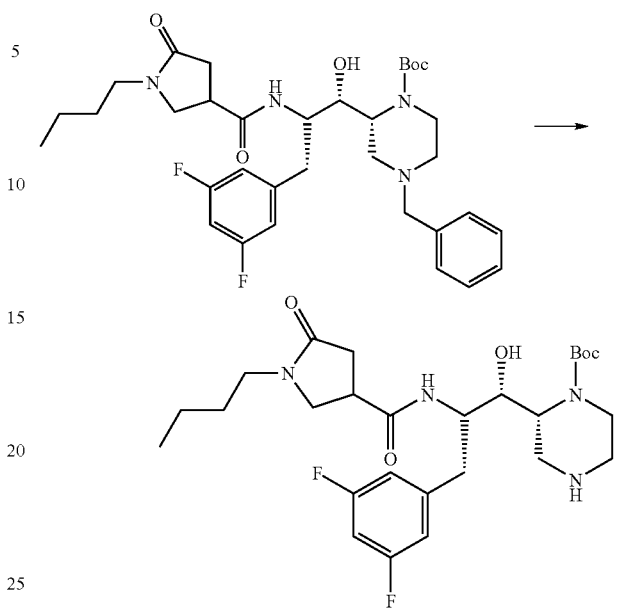

A mixture of the product of Step 1 (1.19 g, 1.89 mmol) and 20% Pd(OH)$_2$/C (1.20 g) in EtOH (20 ml) was stirred under H$_2$ for 4 h. The mixture was filtered through a pad of Celite and concentrated. The residue was partitioned between CH$_2$Cl$_2$ (100 ml) and 1N NaOH (20 ml). The organic layer was dried (MgSO$_4$) and concentrated to give the product (965 mg, 95%). MS m/e 539 (M+H)$^+$.

Step 3:

To a mixture of the product of Step 2 (10 mg, 19 mmol) and PS-DIEA (33 mg, 124 µmol) in CH$_3$CN/THF (7:3, 1 ml) was added the sulfonyl chloride (0.5 M in 1,2-dichloroethane, 56 µl, 28 µmol). The mixture was shaken at RT for 16 h and filtered into a well charged with PS-NCO (37 mg, 57 mmol) and PS-trisamine (32 mg, 135 µmol). The resulting mixture was shaken at RT for 24 h and filtered. The filtrate was concentrated and the residue was dissolved in 20% TFA/CH$_2$Cl$_2$ (1 ml). The solution was shaken at RT for 2.5 h and evaporated. 1N HCl/MeOH (400 µl) was added and the mixture was shaken for 30 min. The mixture was evaporated then dried in vacuo to give the product.

| Ex. | Structure | LCMS (condition A) |
|---|---|---|
| 8C | 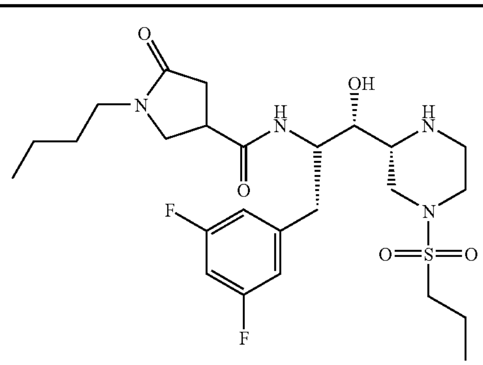 | $t_R$ = 3.07 min<br>m/e = 545<br>(M + H)$^+$ |

| Ex. | Structure | LCMS (condition A) |
|---|---|---|
| 8D | 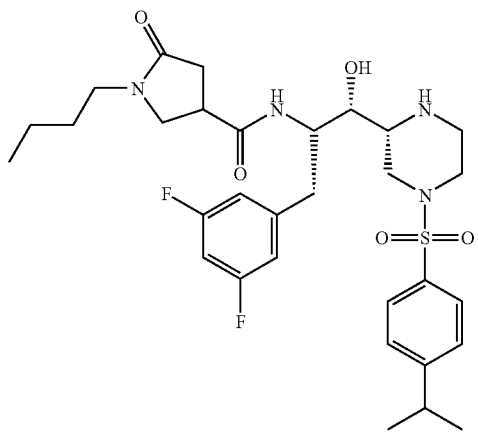 | $t_R$ = 3.52 min<br>m/e = 621<br>$(M + H)^+$ |
| 8E | 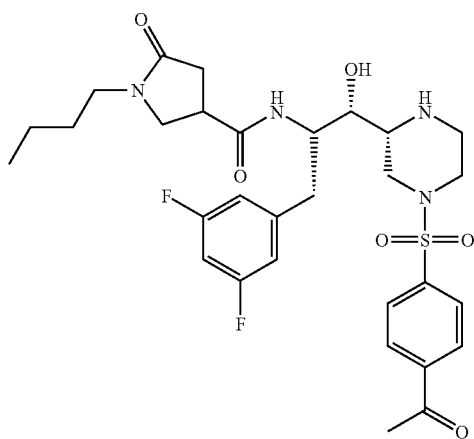 | $t_R$ = 3.92 min<br>m/e = 621<br>$(M + H)^+$ |
| 8F | 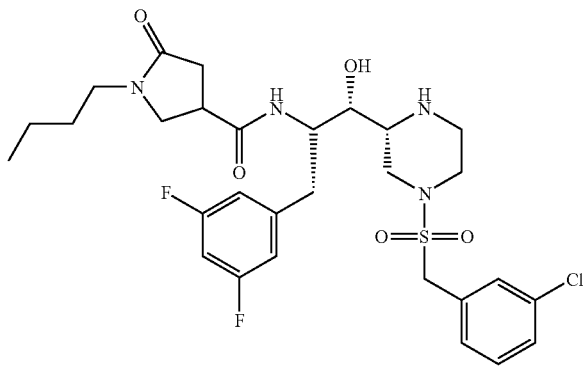 | $t_R$ = 4.15 min<br>m/e = 627<br>$(M + H)^+$ |

-continued

| Ex. | Structure | LCMS (condition A) |
|---|---|---|
| 8G | 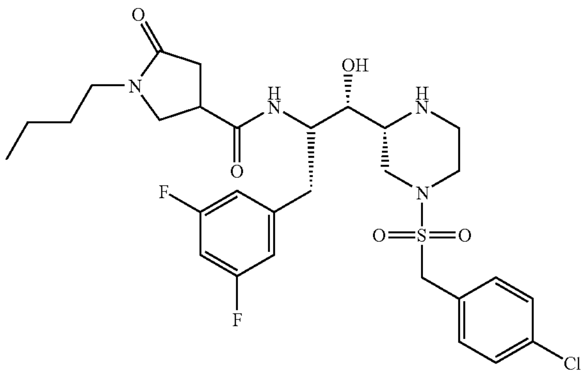 | $t_R$ = 4.12 min<br>m/e = 627<br>(M + H)⁺ |
| 8H | 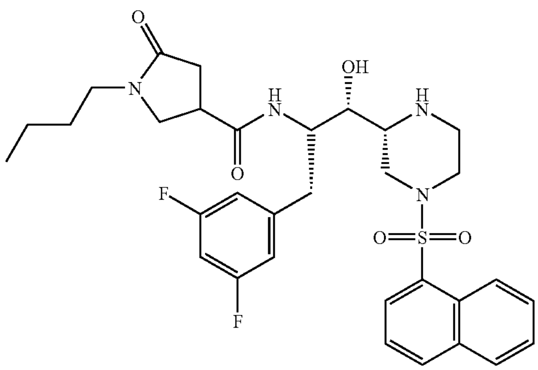 | $t_R$ = 4.13 min<br>m/e = 629<br>(M + H)⁺ |
| 8I | 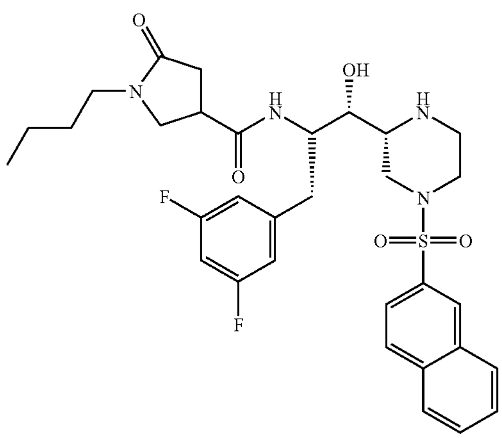 | $t_R$ = 4.18 min<br>m/e = 629<br>(M + H)⁺ |
| 8J | 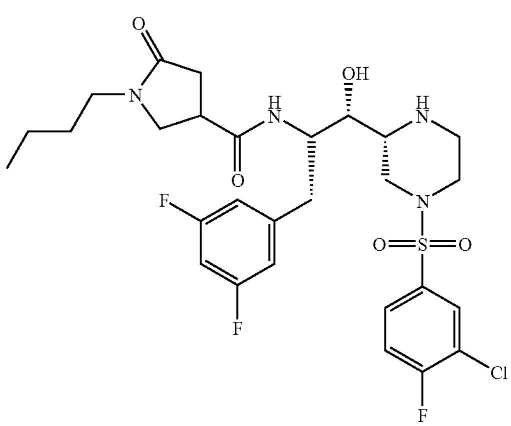 | $t_R$ = 4.15 min<br>m/e = 631<br>(M + H)⁺ |

| Ex. | Structure | LCMS (condition A) |
|---|---|---|
| 8K | 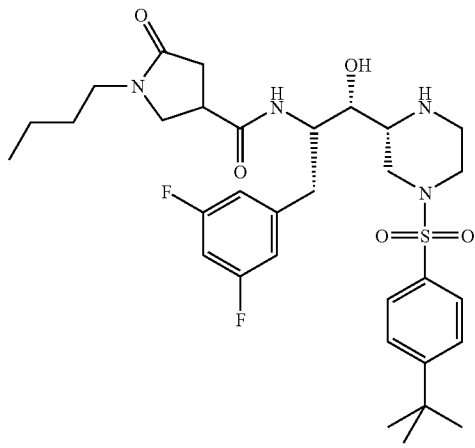 | $t_R$ = 4.37 min<br>m/e = 635<br>$(M + H)^+$ |
| 8L | 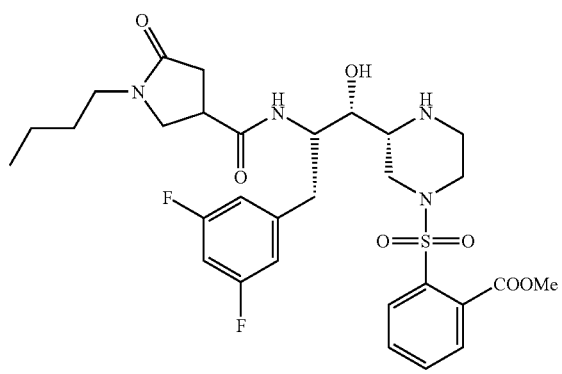 | $t_R$ = 3.92 min<br>m/e = 637<br>$(M + H)^+$ |
| 8M | 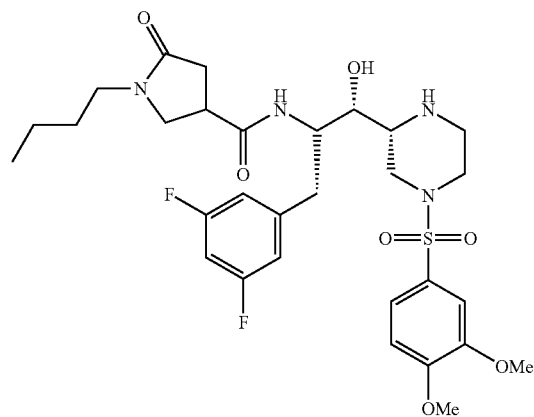 | $t_R$ = 3.89 min<br>m/e = 639<br>$(M + H)^+$ |

| Ex. | Structure | LCMS (condition A) |
|---|---|---|
| 8N | 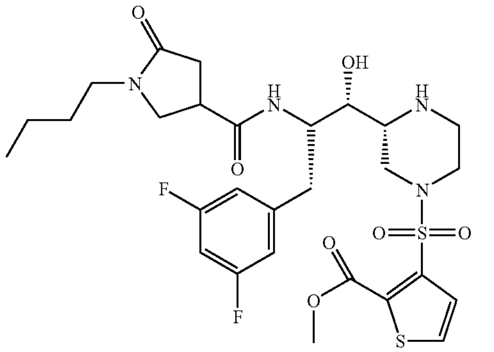 | $t_R$ = 3.88 min<br>m/e = 643<br>$(M + H)^+$ |
| 8O | 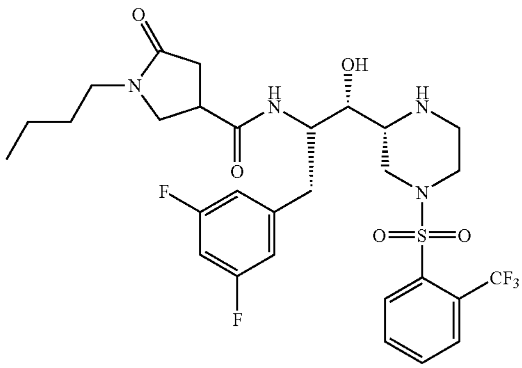 | $t_R$ = 4.04 min<br>m/e = 647<br>$(M + H)^+$ |
| 8P | 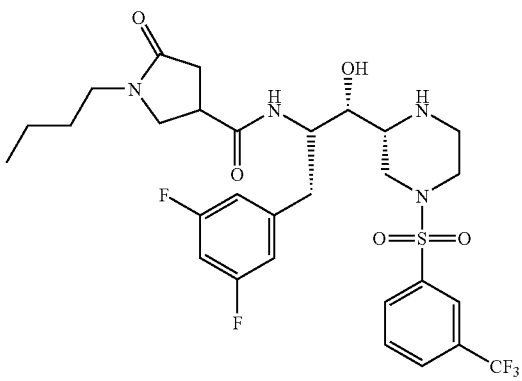 | $t_R$ = 4.18 min<br>m/e = 647<br>$(M + H)^+$ |
| 8Q | 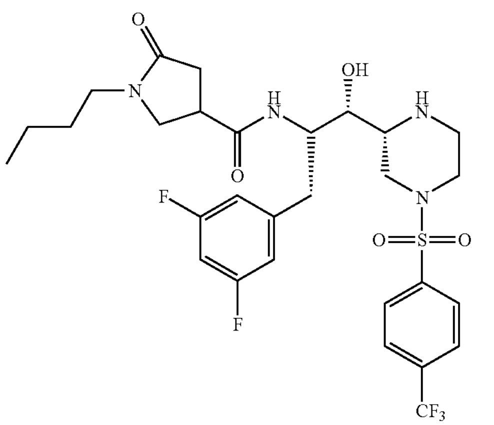 | $t_R$ = 4.23 min<br>m/e = 647<br>$(M + H)^+$ |

-continued

| Ex. | Structure | LCMS (condition A) |
|---|---|---|
| 8R | 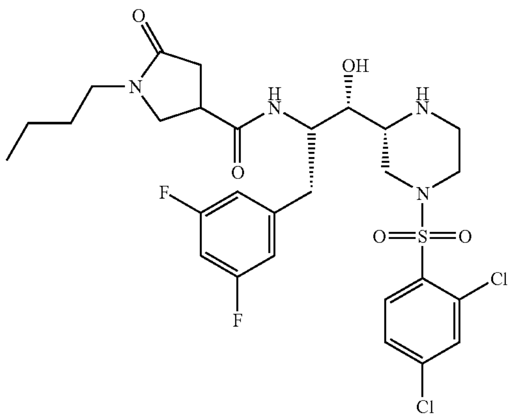 | $t_R$ = 4.18 min<br>m/e = 647<br>(M + H)$^+$ |
| 8S | 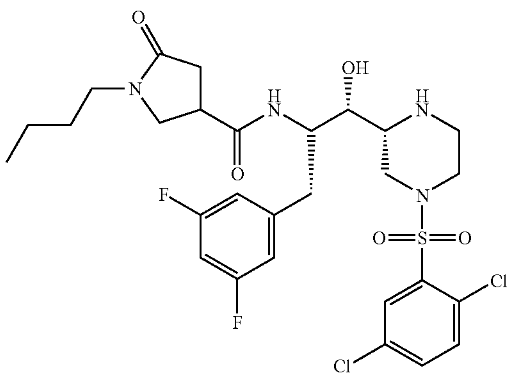 | $t_R$ = 4.15 min<br>m/e = 647<br>(M + H)$^+$ |
| 8T | 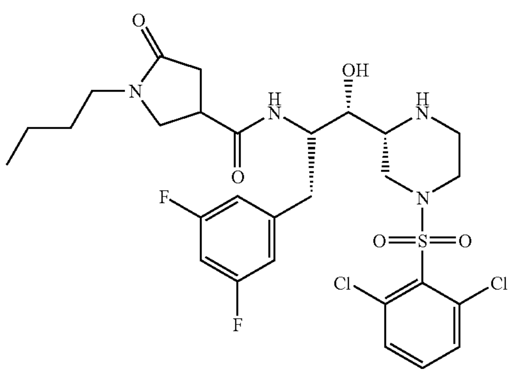 | $t_R$ = 4.02 min<br>m/e = 647<br>(M + H)$^+$ |
| 8U | 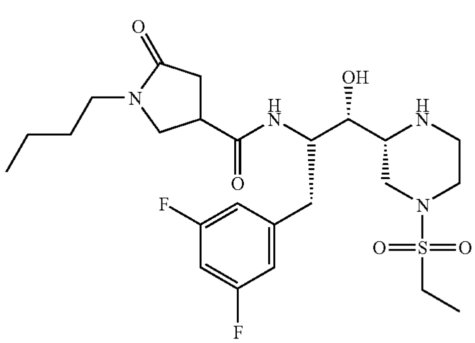 | $t_R$ = 3.63 min<br>m/e = 531<br>(M + H)$^+$ |

-continued

| Ex. | Structure | LCMS (condition A) |
|---|---|---|
| 8V | 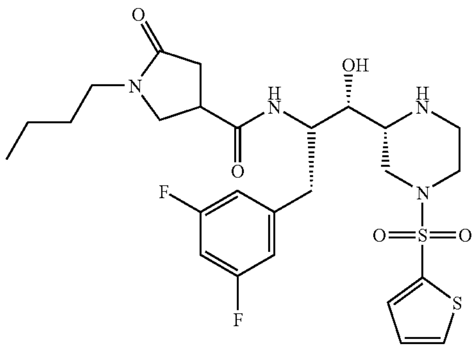 | $t_R$ = 3.86 min<br>m/e = 585<br>(M + H)⁺ |
| 8W | 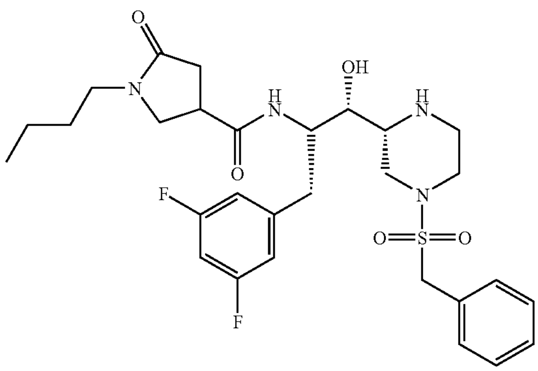 | $t_R$ = 3.92 min<br>m/e = 593<br>(M + H)⁺ |
| 8X | 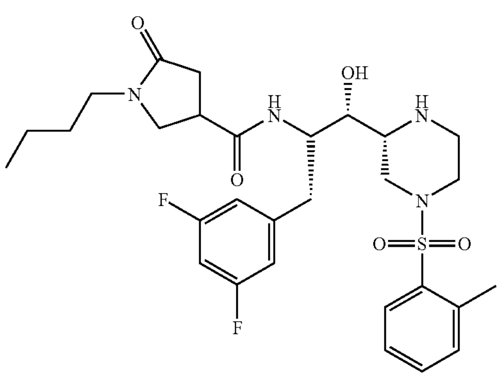 | $t_R$ = 3.97 min<br>m/e = 593<br>(M + H)⁺ |
| 8Y | 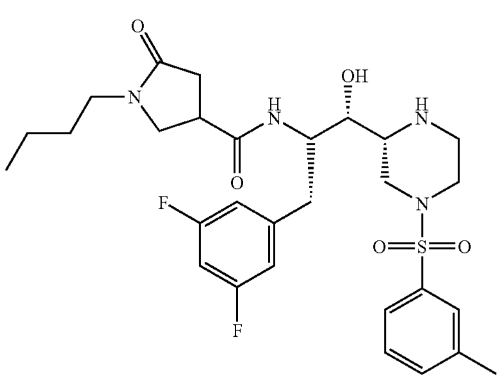 | $t_R$ = 4.03 min<br>m/e = 593<br>(M + H)⁺ |

| Ex. | Structure | LCMS (condition A) |
|---|---|---|
| 8Z | 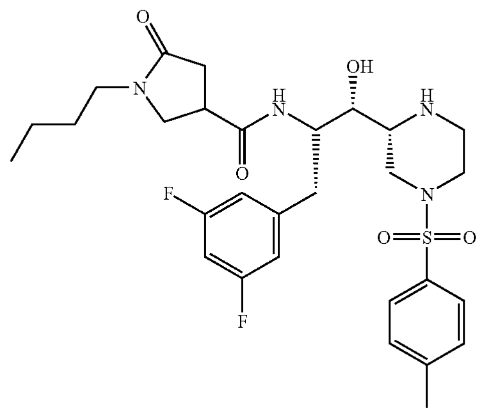 | $t_R$ = 4.01 min<br>m/e = 593<br>$(M + H)^+$ |
| 8AA | 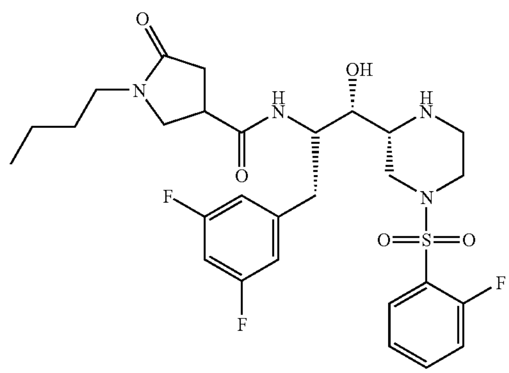 | $t_R$ = 3.87 min<br>m/e = 597<br>$(M + H)^+$ |
| 8BB | 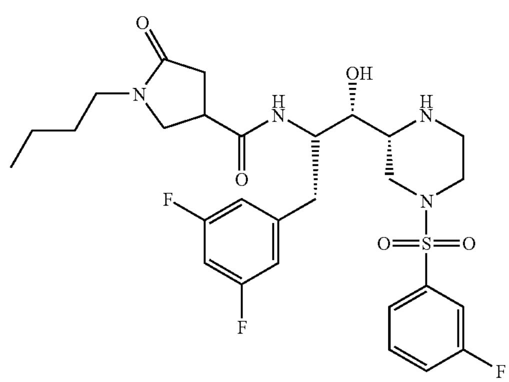 | $t_R$ = 3.95 min<br>m/e = 597<br>$(M + H)^+$ |
| 8CC | 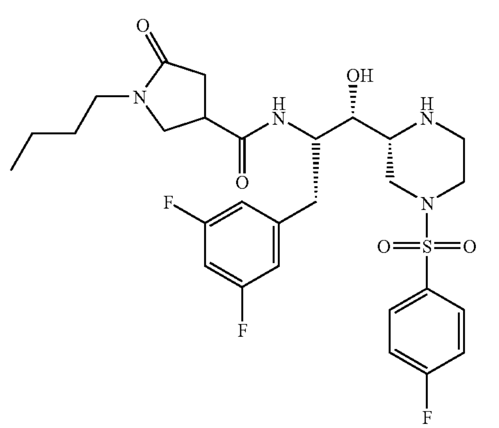 | $t_R$ = 3.97 min<br>m/e = 597<br>$(M + H)^+$ |

-continued
| Ex. | Structure | LCMS (condition A) |
|---|---|---|
| 8DD | 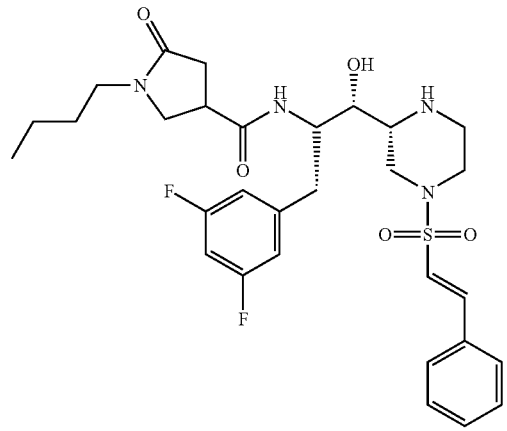 | $t_R$ = 4.11 min<br>m/e = 605<br>(M + H)$^+$ |
| 8EE | 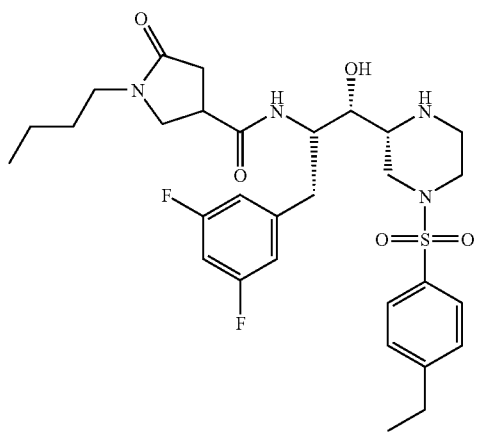 | $t_R$ = 4.15 min<br>m/e = 607<br>(M + H)$^+$ |
| 8FF | 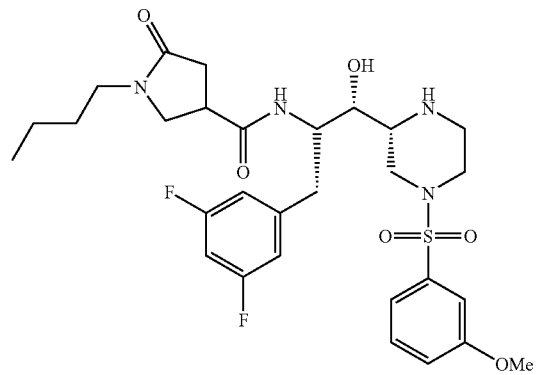 | $t_R$ = 3.99 min<br>m/e = 609<br>(M + H)$^+$ |

-continued

| Ex. | Structure | LCMS (condition A) |
|---|---|---|
| 8GG | 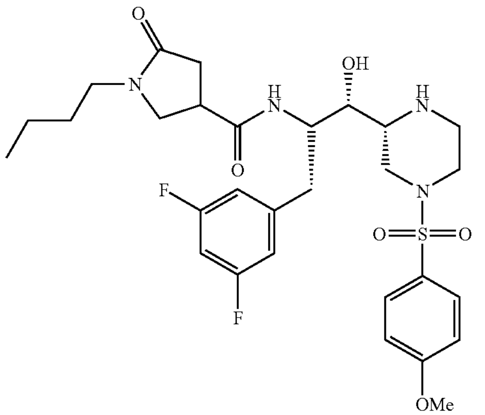 | $t_R$ = 3.96 min<br>m/e = 609<br>$(M + H)^+$ |
| 8HH | 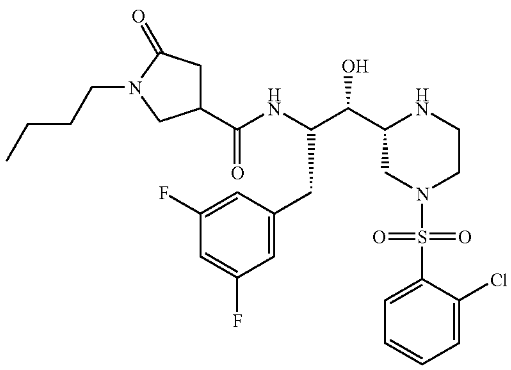 | $t_R$ = 3.94 min<br>m/e = 613<br>$(M + H)^+$ |
| 8II | 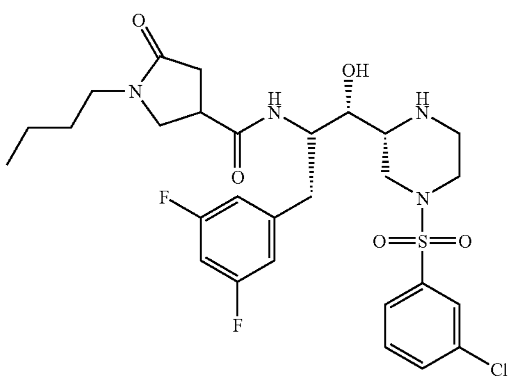 | $t_R$ = 4.07 min<br>m/e = 613<br>$(M + H)^+$ |
| 8JJ | 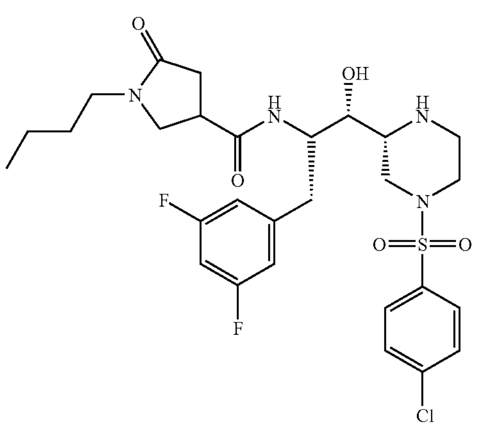 | $t_R$ = 4.11 min<br>m/e = 613<br>$(M + H)^+$ |

-continued
| Ex. | Structure | LCMS (condition A) |
|---|---|---|
| 8KK | 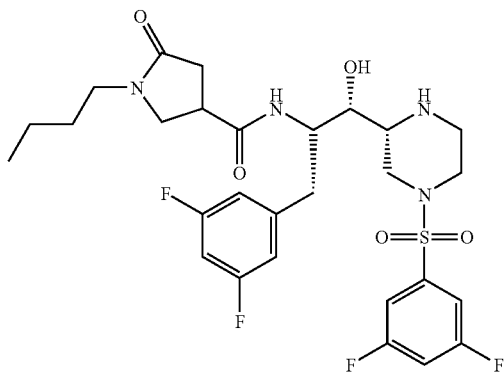 | $t_R$ = 4.05 min<br>m/e = 615<br>$(M + H)^+$ |
| 8LL | 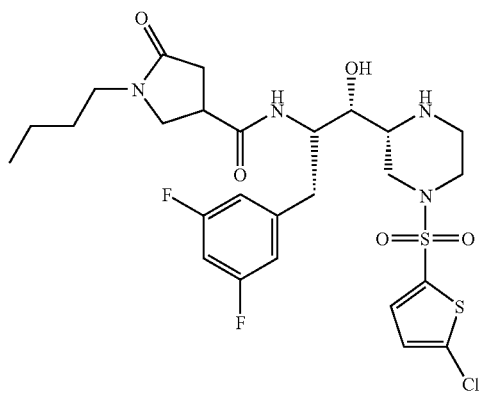 | $t_R$ = 4.07 min<br>m/e = 619<br>$(M + H)^+$ |
| 8MM | 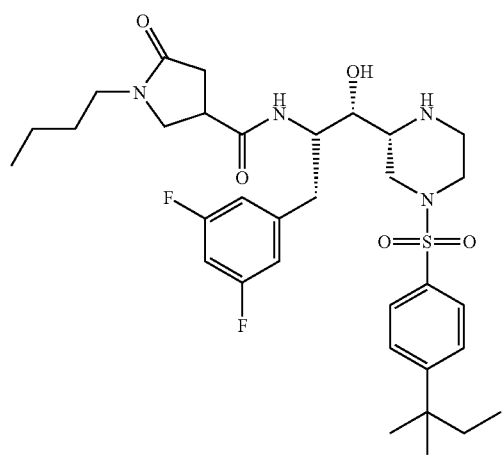 | $t_R$ = 4.49 min<br>m/e = 649<br>$(M + H)^+$ |

| Ex. | Structure | LCMS (condition A) |
|---|---|---|
| 8NN | 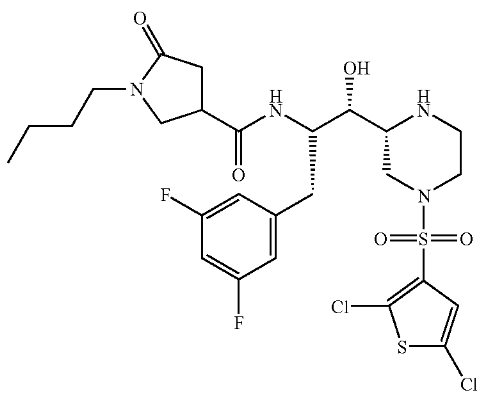 | $t_R$ = 4.20 min<br>m/e = 653<br>$(M + H)^+$ |
| 8OO | 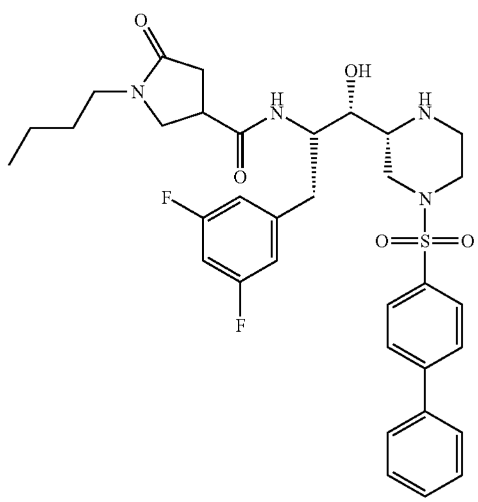 | $t_R$ = 4.36 min<br>m/e = 655<br>$(M + H)^+$ |
| 8PP | 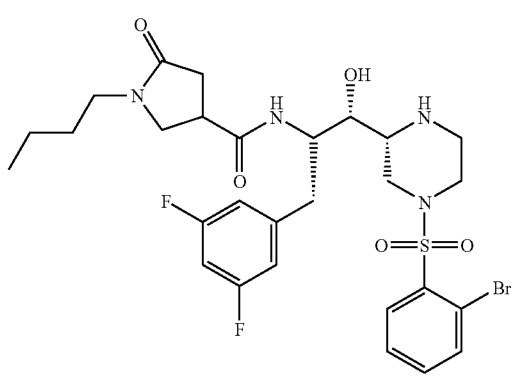 | $t_R$ = 3.98 min<br>m/e = 657<br>$(M + H)^+$ |

-continued
| Ex. | Structure | LCMS (condition A) |
|---|---|---|
| 8QQ | 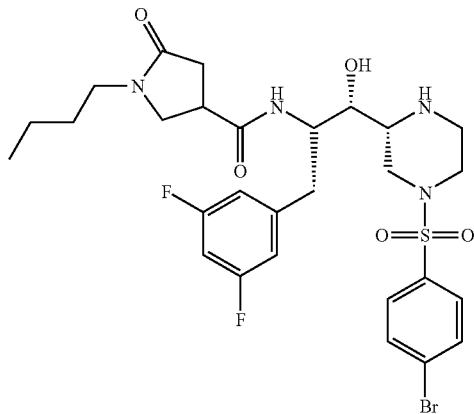 | $t_R$ = 4.13 min<br>m/e = 657<br>$(M + H)^+$ |
| 8RR | 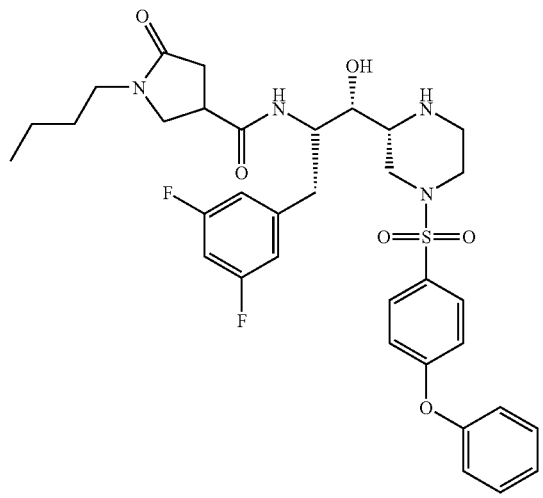 | $t_R$ = 4.41 min<br>m/e = 671<br>$(M + H)^+$ |
| 8SS | 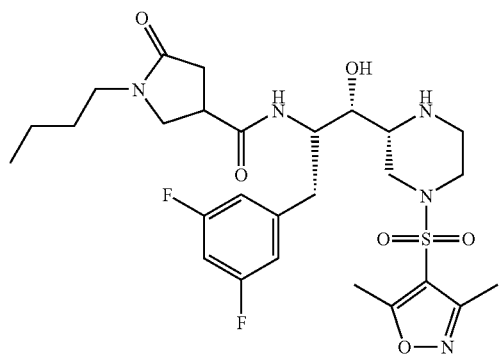 | $t_R$ = 3.88 min<br>m/e = 598<br>$(M + H)^+$ |

| Ex. | Structure | LCMS (condition A) |
|---|---|---|
| 8TT | 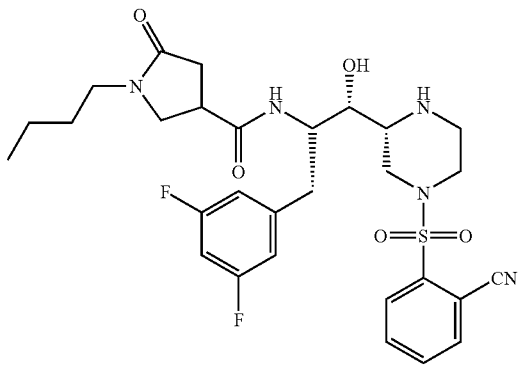 | $t_R$ = 3.87 min<br>m/e = 604<br>$(M + H)^+$ |
| 8UU | 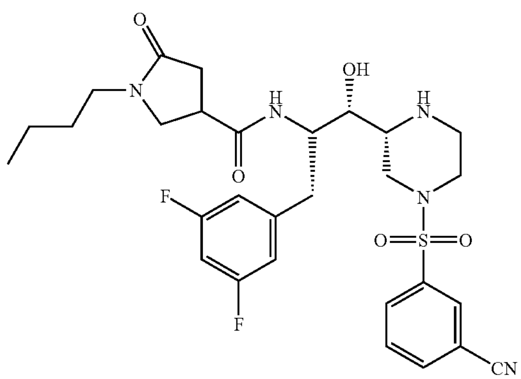 | $t_R$ = 3.93 min<br>m/e = 604<br>$(M + H)^+$ |
| 8VV | 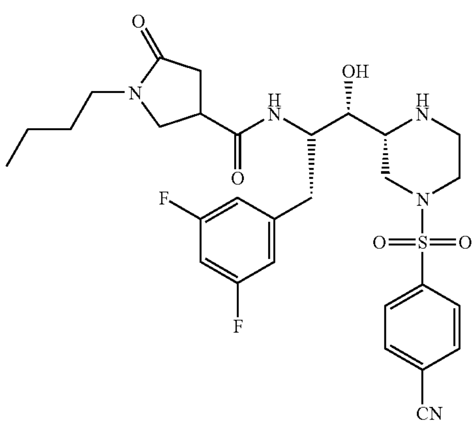 | $t_R$ = 3.97 min<br>m/e = 604<br>$(M + H)^+$ |
| 8WW | 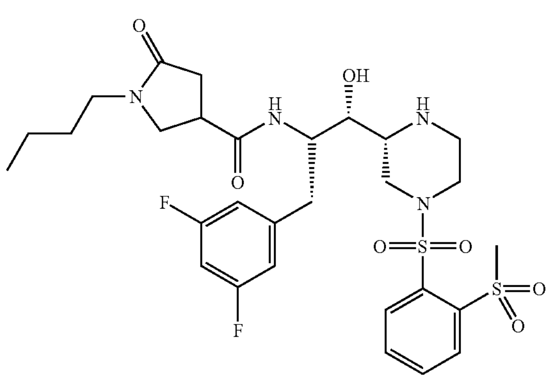 | $t_R$ = 3.83 min<br>m/e = 657<br>$(M + H)^+$ |

-continued

| Ex. | Structure | LCMS (condition A) |
|---|---|---|
| 8XX | 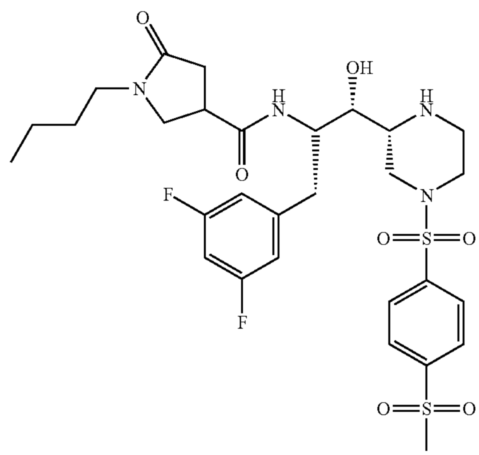 | $t_R$ = 3.83 min<br>m/e = 657<br>(M + H)+ |
| 8YY | 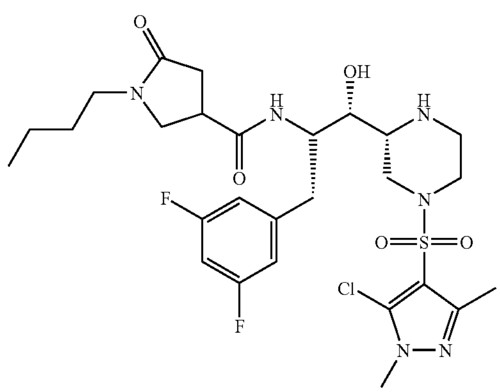 | $t_R$ = 3.82 min<br>m/e = 631<br>(M + H)+ |
| 8ZZ | 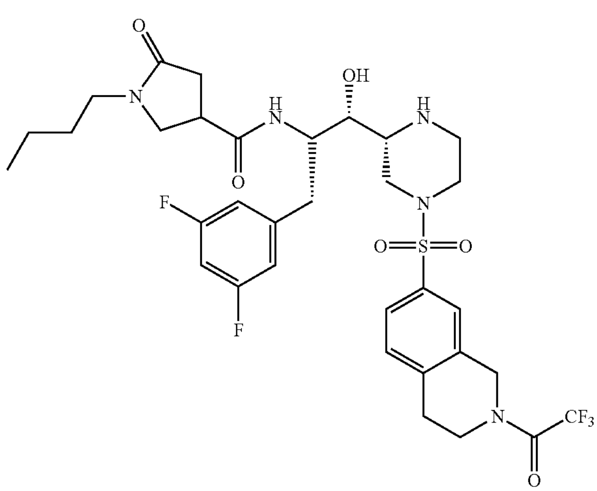 | $t_R$ = 4.18 min<br>m/e = 730<br>(M + H)+ |

-continued

| Ex. | Structure | LCMS (condition A) |
|---|---|---|
| 8AAA | 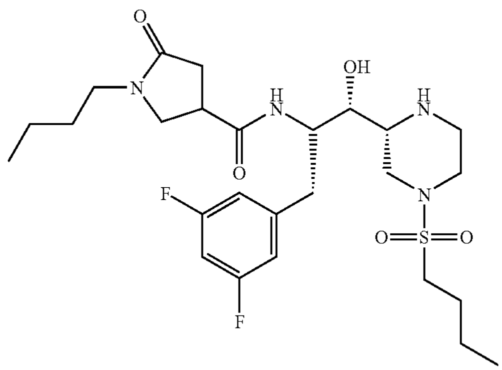 | $t_R$ = 3.91 min<br>m/e = 559<br>$(M + H)^+$ |
| 8BBB | 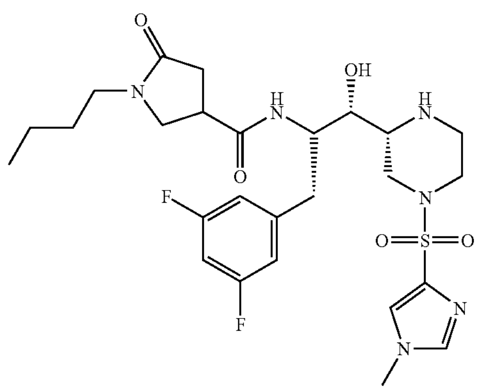 | $t_R$ = 3.57 min<br>m/e = 583<br>$(M + H)^+$ |
| 8CCC | 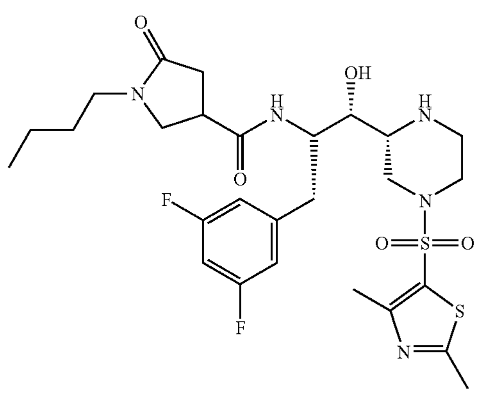 | $t_R$ = 3.80 min<br>m/e = 614<br>$(M + H)^+$ |
| 8DDD | 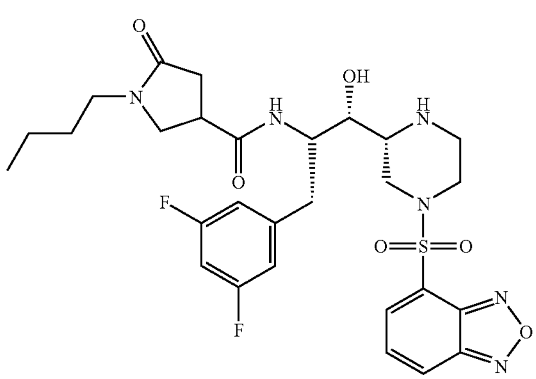 | $t_R$ = 3.92 min<br>m/e = 621<br>$(M + H)^+$ |

| Ex. | Structure | LCMS (condition A) |
|---|---|---|
| 8EEE | 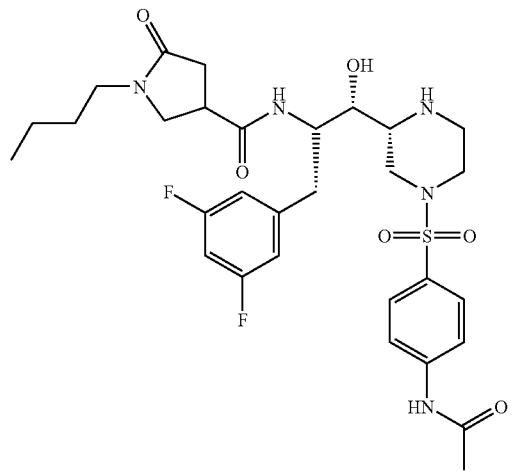 | $t_R$ = 3.72 min<br>m/e = 636<br>$(M + H)^+$ |
| 8FFF | 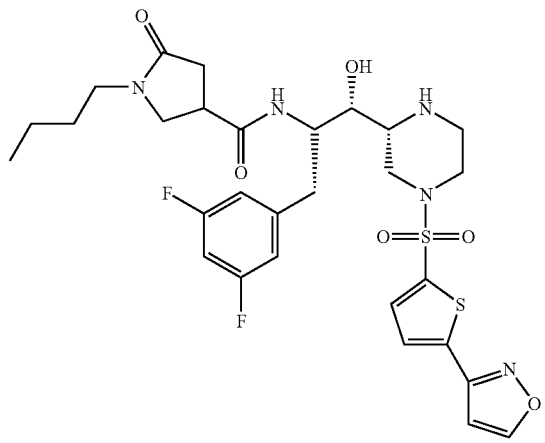 | $t_R$ = 4.02 min<br>m/e = 652<br>$(M + H)^+$ |
| 8GGG | 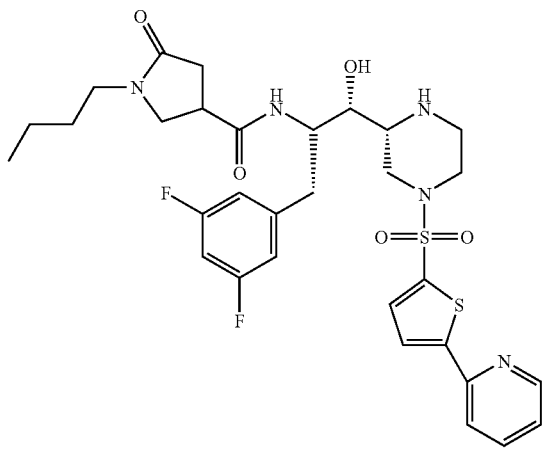 | $t_R$ = 4.09 min<br>m/e = 662<br>$(M + H)^+$ |

| Ex. | Structure | LCMS (condition A) |
|---|---|---|
| 8HHH | 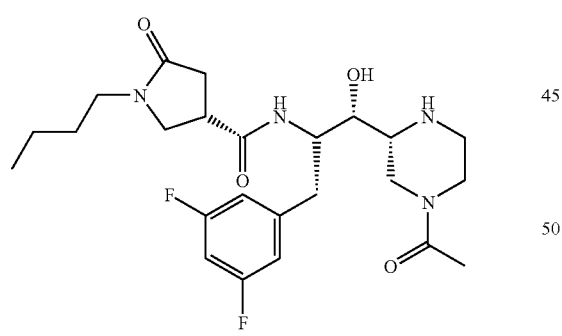 | $t_R$ = 3.76 min<br>m/e = 657<br>$(M + H)^+$ |
| 8III | 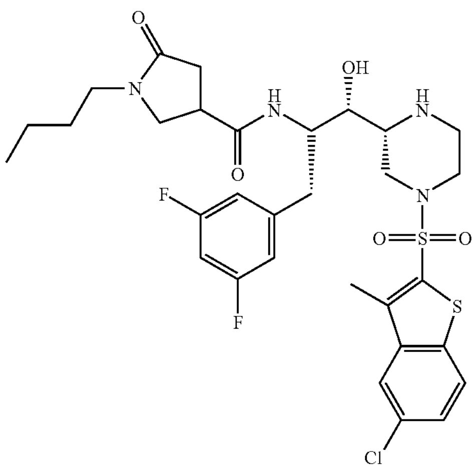 | $t_R$ = 4.44 min<br>m/e = 683<br>$(M + H)^+$ |

Example 9

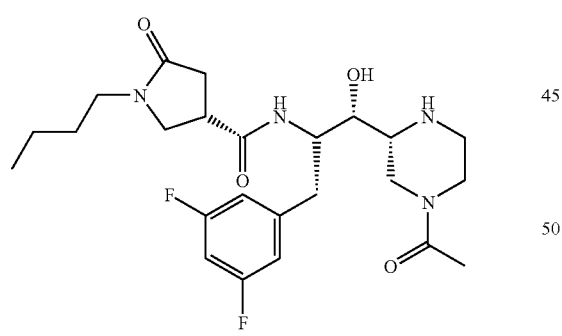

Step 1:

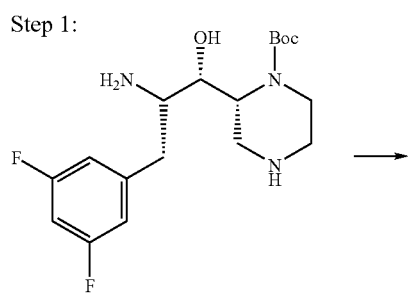

-continued

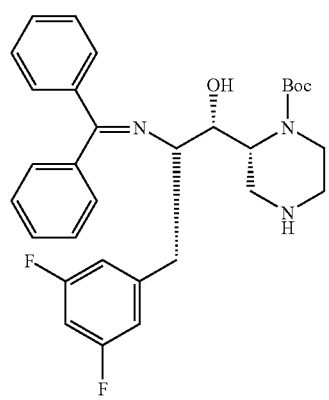

A mixture of the product of Example 8A, Step 2 (419 mg, 1.13 mmol) and benzophenone imine (240 mg, 1.28 mmol) in CH$_2$Cl$_2$ (20 ml) was refluxed for 16 h. The mixture was concentrated and purified by column chromatography (gradient MeOH/CH$_2$Cl$_2$ 0-6%) to give the product (376 mg, 62%). MS m/e 536 (M+H)$^+$.

Step 2:

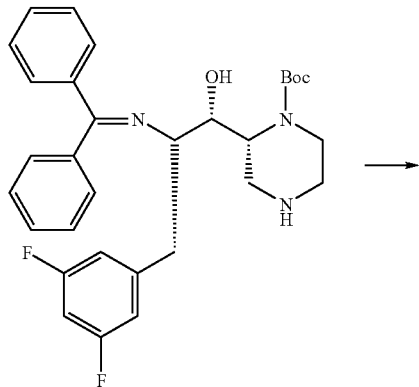

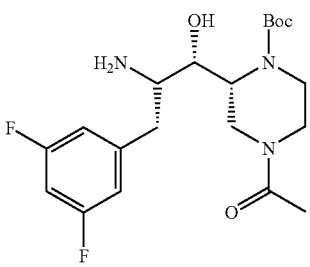

A solution of the product of Step 2 (116 mg, 0.200 mmol) and hydroxylamine hydrochloride (186 mg, 2.67 mmol) in EtOH (8 ml) and water (2 ml) was heated to 50° C. for 2 h. The mixture was concentrated and the residue was partitioned between $CH_2Cl_2$ (50 ml) and 1N NaOH (20 ml). The organic layer was dried ($MgSO_4$), concentrated, and purified by PTLC (8% $MeOH/CH_2Cl_2$) to give the product (89 mg, 100%). MS m/e 414 (M+H)$^+$.

Step 4:

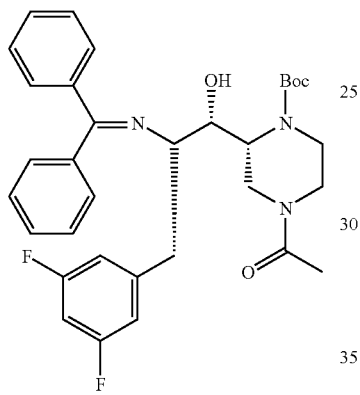

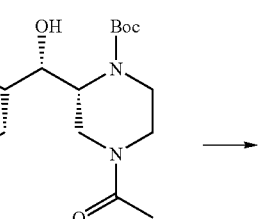

A mixture of the product of Step 1 (133 mg, 0.248 mmol), $Et_3N$ (35 Pl, 0.25 mmol), and acetic anhydride (25 mg, 0.25 mmol) in $CH_2Cl_2$ (10 ml) was stirred in an ice-water bath for 30 min then at RT for 16 h. The mixture was diluted with $CH_2Cl_2$ (40 ml) and washed with 1N NaOH (20 ml). The organic layer was dried ($MgSO_4$), concentrated, and purified by PTLC (3% $MeOH/CH_2Cl_2$) to give the product (116 mg, 81%). MS m/e 578 (M+H)$^+$.

Step 3:

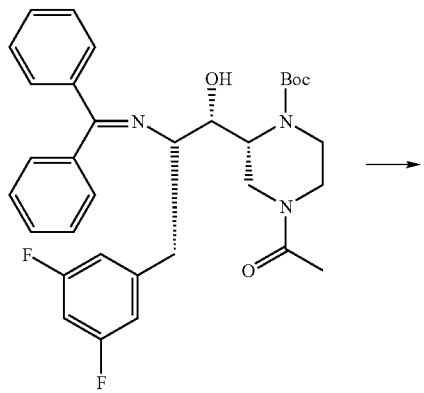

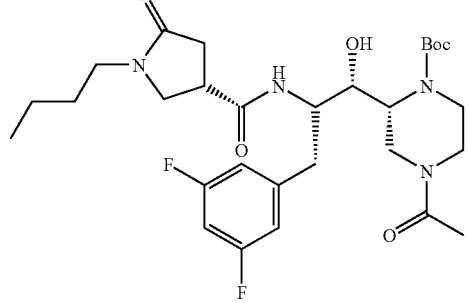

A mixture of the product of Step 3 (89 mg, 0.22 mmol) and Preparation 2LL (39 mg, 0.21 mmol) were coupled in analogy to the procedure of Example 5A Step 5. The crude product was purified by PTLC (5% $MeOH/CH_2Cl_2$) to give the product (49 mg, 39%). MS m/e 581 (M+H)$^+$.

Step 5:

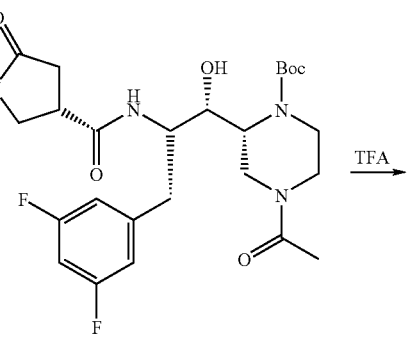

-continued

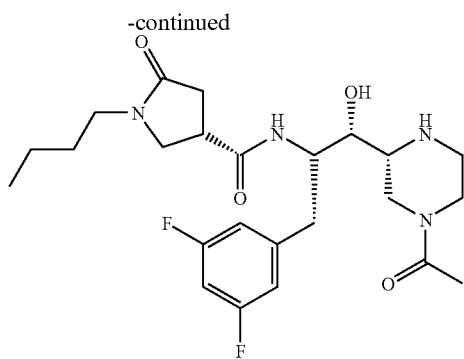

A mixture of the product of Step 4 (49 mg, 0.084 mmol) and TFA (0.9 ml) in $CH_2Cl_2$ (4 ml) was stirred in an ice-water bath for 30 min then at RT for 3 h. The mixture was diluted with $CH_2Cl_2$ (40 ml) and washed with aqueous $NH_4OH$ (15 ml). The organic layer was dried ($MgSO_4$), concentrated, and purified by PTLC (8% $MeOH/CH_2Cl_2$) to give the product (30 mg, 73%). $^1H$ NMR ($CDCl_3$) δ 7.21 (d, 1H, J=8.8 Hz), 6.75 (m, 2H), 6.62 (m, 1H), 4.0-4.4 (m, 3H), 2.9-3.7 (m, 11H), 2.71 (m, 3H), 2.45 (m, 1H), 2.28 (m, 1H), 2.09 (s, 3H), 1.44 (m, 2H), 1.26 (m, 2H), 0.88 (m, 3H). LCMS (Conditions A): $t_R$=2.17 min; m/e 481 $(M+H)^+$.

By essentially the same procedure set forth in Example 9A, the following examples were prepared.

| EX. | Structure | LCMS (Conditions A) |
|---|---|---|
| 9B | 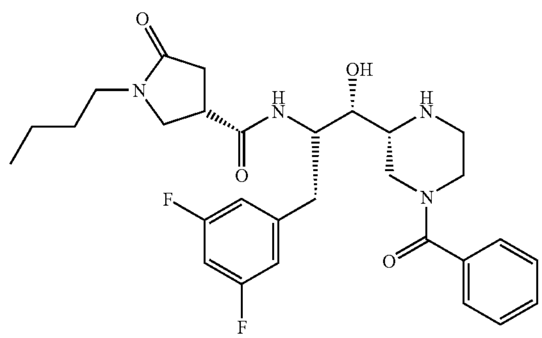 | $t_R$ = 2.86 min<br>m/e 543 $(M + H)^+$ |
| 9C | 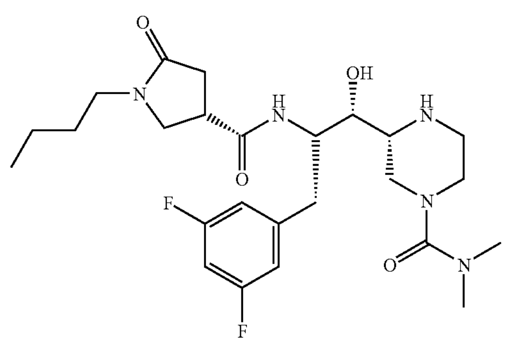 | $t_R$ = 2.60 min<br>m/e 510 $(M + H)^+$ |
| 9D | 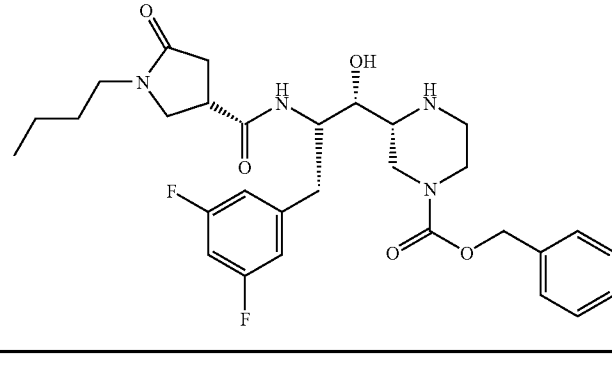 | $t_R$ = 2.98 min<br>m/e 573 $(M + H)^+$ |

Example 10A

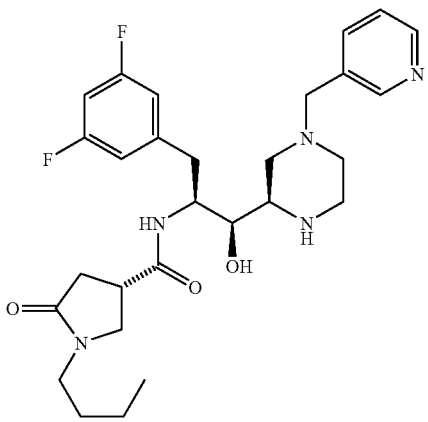

Step 1:

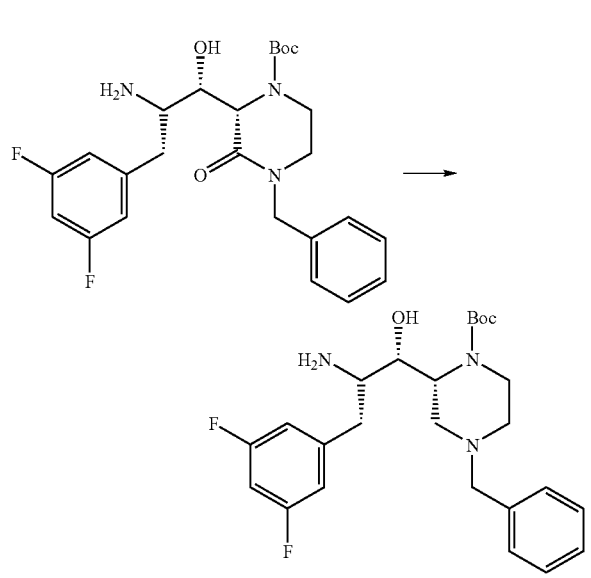

To a solution of the product of Example 5A, Step 4 (326 mg, 0.687 mmol) in THF (3 ml) was added 2M BH₃—SMe₂ in THF (2.0 ml) and the mixture was heated to 60° C. for 16 h. The mixture was treated with saturated citric acid (40 ml) and extracted with EtOAc (3×30 ml). The combined organic layer was evaporated to dryness and the residue was partitioned between CH₂Cl₂ (60 ml) and aqueous NH₄OH (20 ml). The organic layer was dried (MgSO₄) and concentrated to give the product (190 mg, 60%). MS m/e 462 (M+H)⁺.

Step 2:

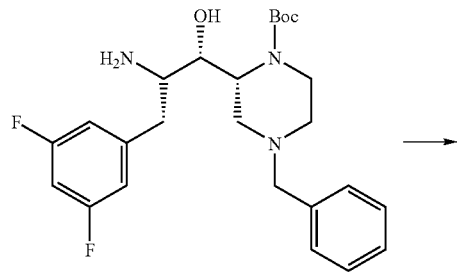

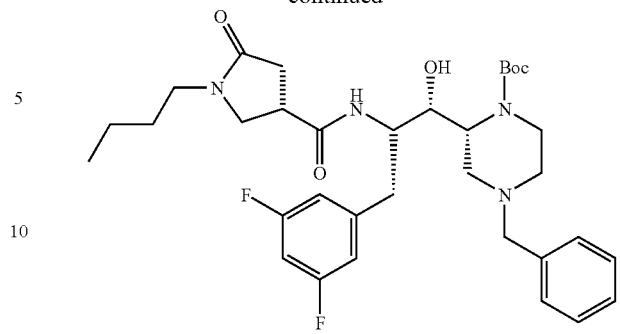

A mixture of the product of Step 1 (527 mg, 2.80 mmol) and Preparation 2LL were couple in analogy to the procedure of Example 5A Step 5 to give the product (832 mg, 70%) as a yellow oil.

Step 3:

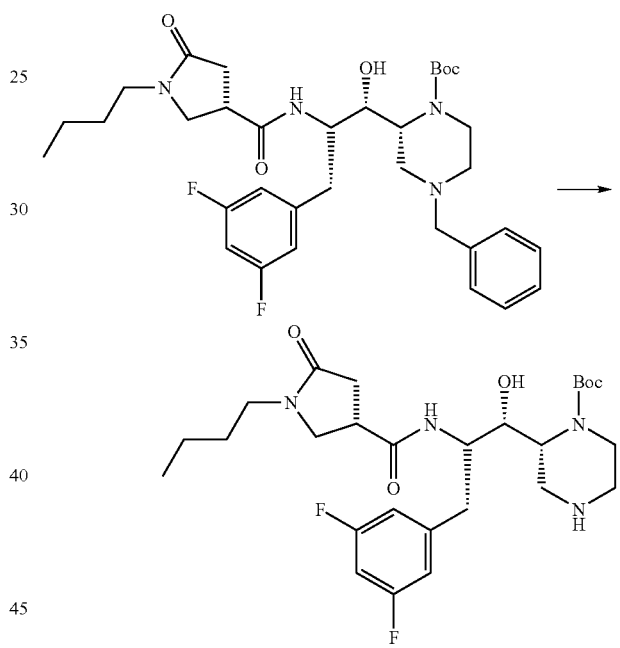

A suspension of the product of Step 2 (832 mg, 1.32 mmol) and Pd(OH)₂/C (670 mg) in MeOH (15 ml) was stirred under a H₂ atmosphere for 6 h. The reaction mixture was filtered and evaporated to give the product (617 mg, 87%). MS m/e 539 (M+H)⁺.

Step 4:

A mixture of the product of Step 3 (18 mg, 0.034 mmol), K₂CO₃ (25 mg, 0.18 mmol) and 3-picolyl chloride hydrochloride (13 mg, 0.08 mmol) in DMF (1 ml) was stirred at RT for 18 h. The reaction mixture was filtered, concentrated and the residue was subjected to preparative HPLC (Conditions B) to give the alkylated product. The product was stirred with 1:4 TFA/CH₂Cl₂ (2 ml) for 2 h, then concentrated. The residue was dissolved in 1N HCl/MeOH and evaporated to give the hydrochloride salt of the product (9 mg) as a light yellow solid. LCMS (Conditions A) $t_R$=2.13 min, m/e 530 (M+H)⁺.

Using the appropriate alkylating reagent and essentially the same procedure described for Example 10A, the following Examples were prepared.

| Ex. | Reagent | Structure | LCMS (Conditions A) |
|---|---|---|---|
| 10B | bromoacetamide | (structure) | $t_R$ = 2.15 min; 496 (M + H)$^+$ |
| 10C | 2-chloro-N,N-dimethylacetamide | (structure) | $t_R$ = 2.28 min; 524 (M + H)$^+$ |
| 10D | 2-chloro-N,N-diethylacetamide | (structure) | $t_R$ = 2.38 min; 552 (M + H)$^+$ |
| 10E | 1-(2-chloroacetyl)pyrrolidine | (structure) | $t_R$ = 2.28 min; 550 (M + H)$^+$ |

| Ex. | Reagent | Structure | LCMS (Conditions A) |
|---|---|---|---|
| 10F | | 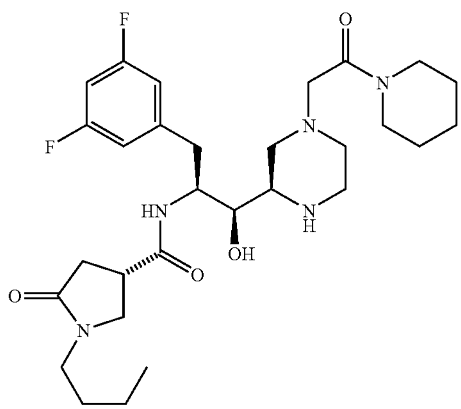 | $t_R$ = 2.41 min; 564 (M + H)$^+$ |
| 10G | | 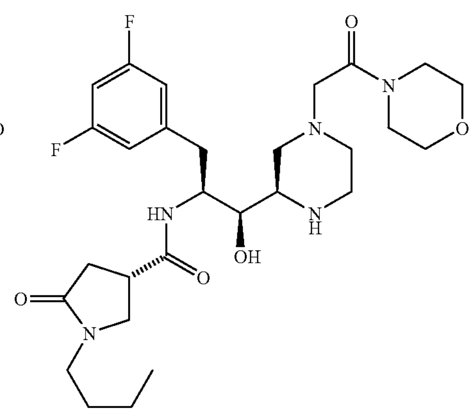 | $t_R$ = 2.17 min; 566 (M + H)$^+$ |
| 10H | | 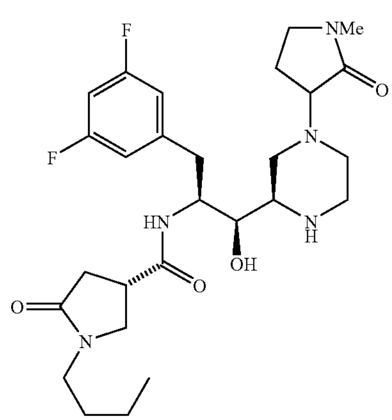 | $t_R$ = 2.42 min; 536 (M + H)$^+$ |
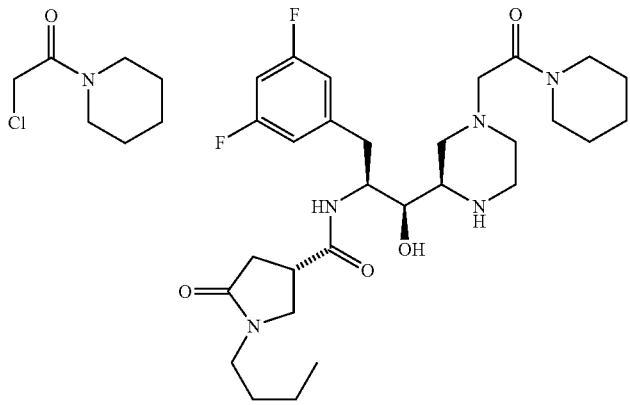
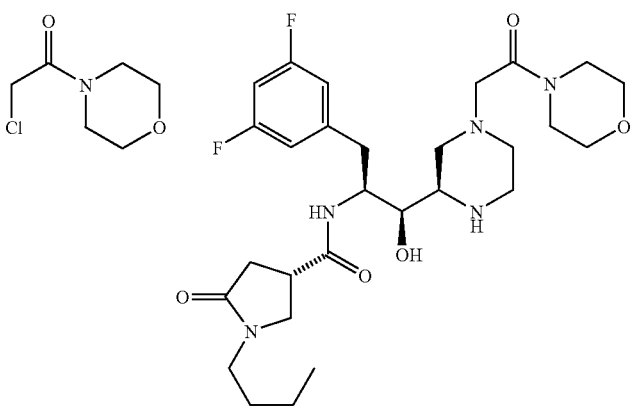
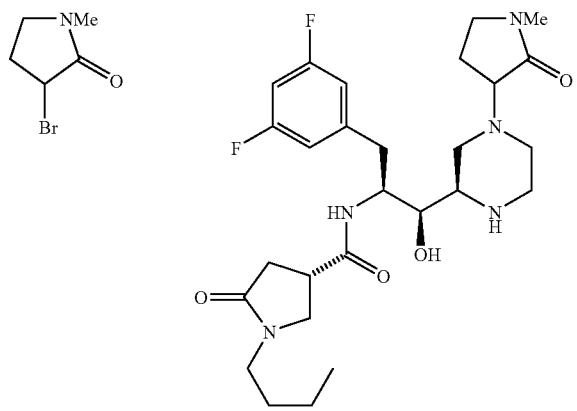

-continued
| Ex. | Reagent | Structure | LCMS (Conditions A) |
|---|---|---|---|
| 10I | 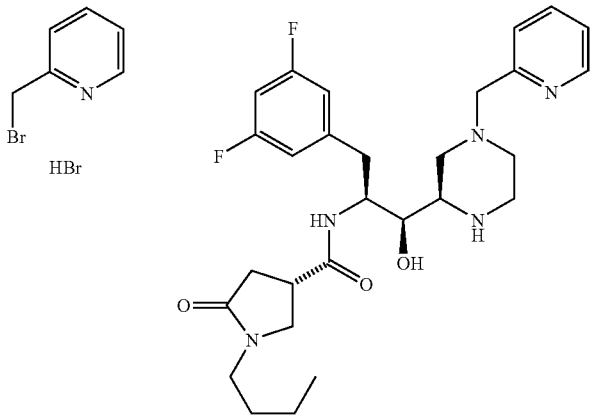 | 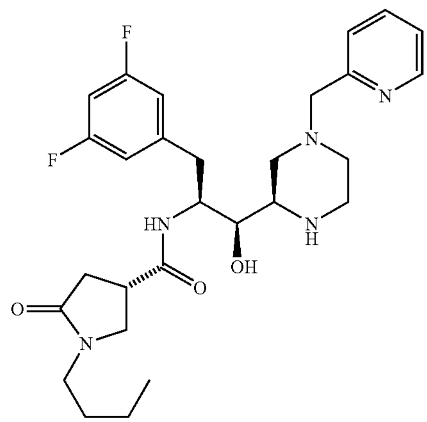 | $t_R$ = 2.22 min; 530 (M + H)$^+$ |
| 10J | 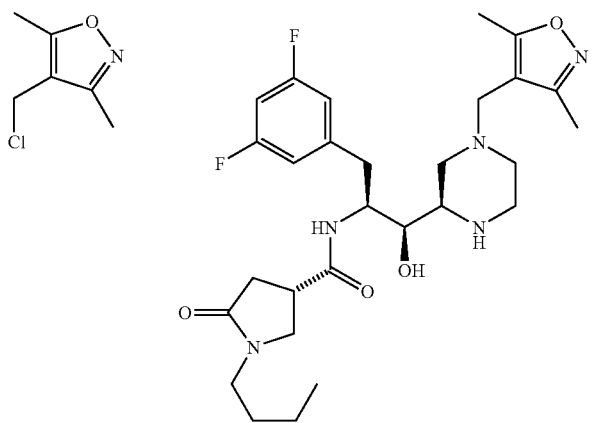 | 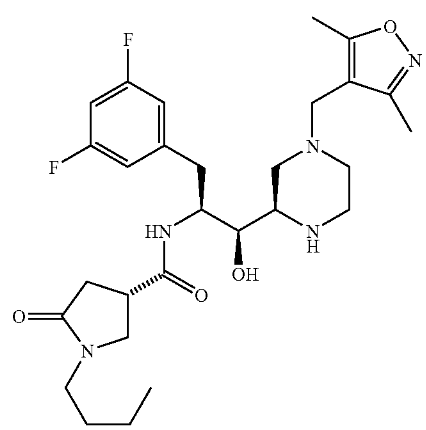 | $t_R$ = 2.53 min; 548 (M + H)$^+$ |
| 10K | 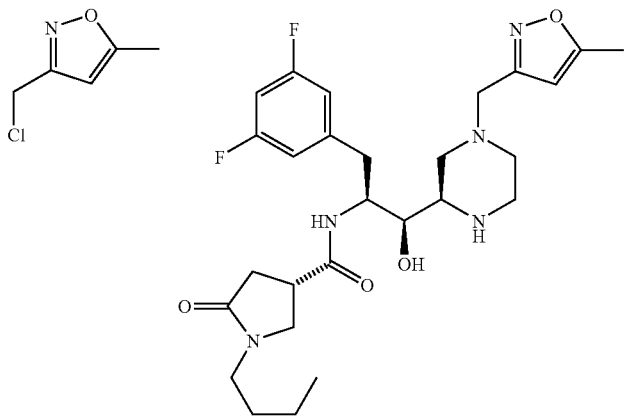 | 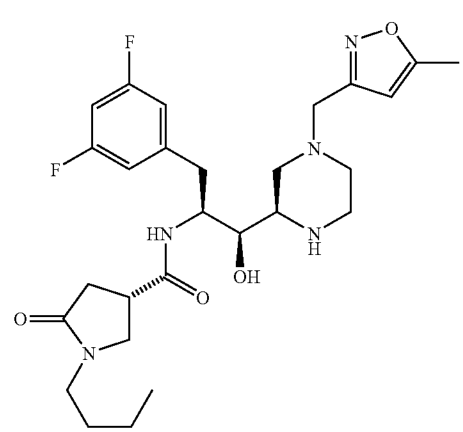 | $t_R$ = 2.61 min; 534 (M + H)$^+$ |

| Ex. | Reagent | Structure | LCMS (Conditions A) |
|---|---|---|---|
| 10L | 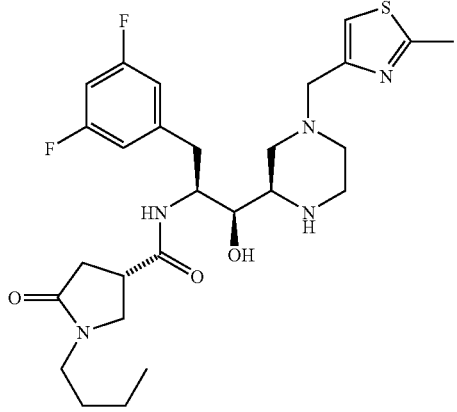 | 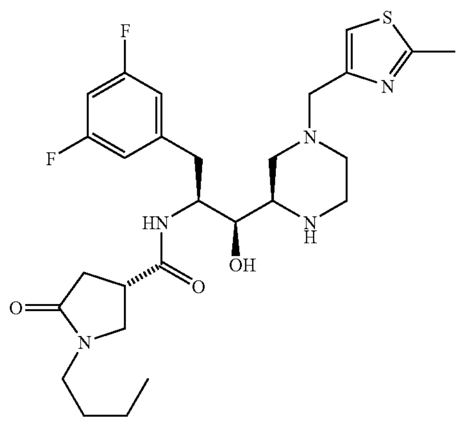 | $t_R$ = 2.51 min; 550 (M + H)$^+$ |
| 10M | 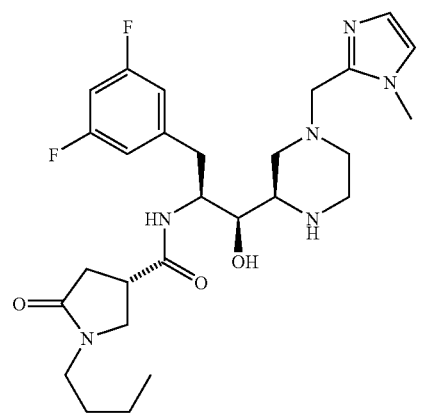 | 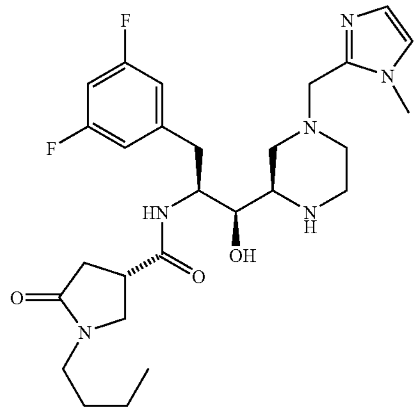 | $t_R$ = 2.17 min; 533 (M + H)$^+$ |

Example 11A

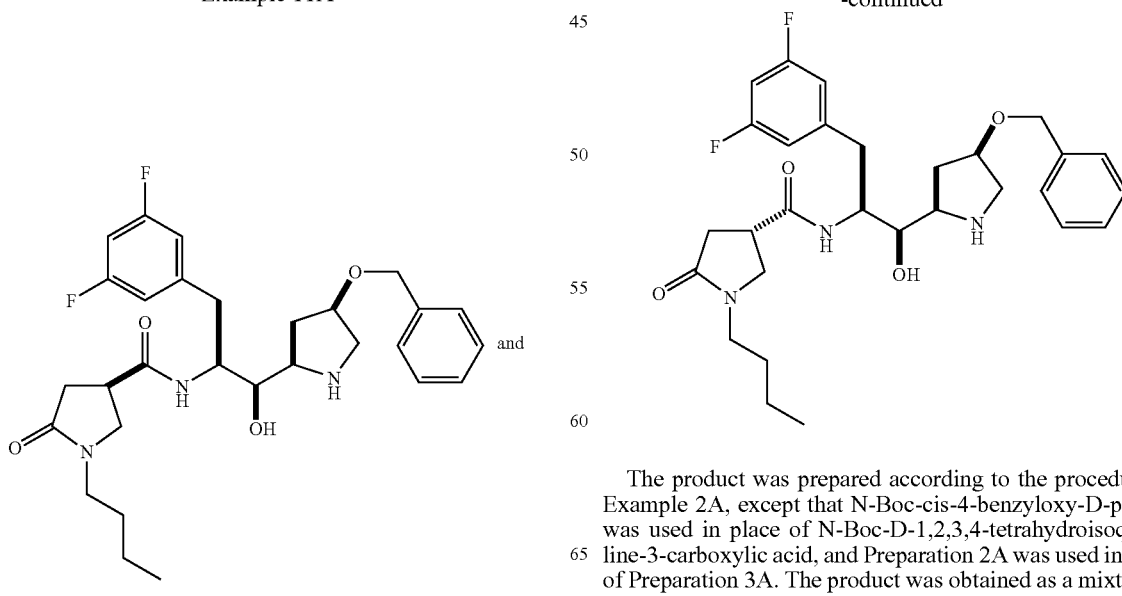

The product was prepared according to the procedure of Example 2A, except that N-Boc-cis-4-benzyloxy-D-proline was used in place of N-Boc-D-1,2,3,4-tetrahydroisoquinoline-3-carboxylic acid, and Preparation 2A was used in place of Preparation 3A. The product was obtained as a mixture of two diastereomers that were separated by reverse-phase preparative HPLC (Conditions C). Diastereomer 1: ¹H NMR (400 MHz, CD₃OD) δ 8.40 (bs, 1 H), 7.20-7.35 (m, 5 H), 6.73-6.85 (m, 3 H), 4.51 (m, 2 H), 4.29 (m, 1 H), 3.99 (m, 1 H), 3.81 (m, 1 H), 3.68 (m, 1 H), 3.35-3.46 (m, 3 H), 3.17 (m, 3 H), 2.94-3.15 (m, 1 H), 2.34-2.64 (m, 4 H), 2.13 (m, 1 H), 1.97 (m, 1 H), 1.43 (m, 2 H), 1.25 (m, 2 H), 0.88 (m, 3 H); LCMS (Conditions A) $t_R$=4.28 min, 530 (M+H)⁺. Diastereomer 2: ¹H NMR (400 MHz, CD₃OD). δ 8.45 (bs, 1 H), 7.20-7.40 (m, 5 H), 6.74-6.95 (m, 3 H), 4.55 (m, 2 H), 4.28 (m, 1 H), 4.22 (m, 1 H), 4.01 (m, 1 H), 3.76 (m, 1 H), 3.62 (m, 1 H), 3.37 (m, 2 H), 3.17-3.30 (m, 2 H), 3.09 (m, 1 H), 2.98 (m, 1 H), 2.78 (m, 1 H), 2.30-2.60 (m, 4H), 2.11 (m, 1 H), 1.36 (m, 2 H), 1.18 (m, 2 H), 0.88 (m, 3H); LCMS (conditions A) $t_R$=4.38 min, 530 (M+H)⁺.

Using the appropriate carboxylic acid the following Examples were prepared.

| Ex. | Preparation | Structure | LCMS (Conditions A) |
|---|---|---|---|
| 11B | 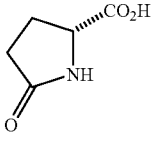 | 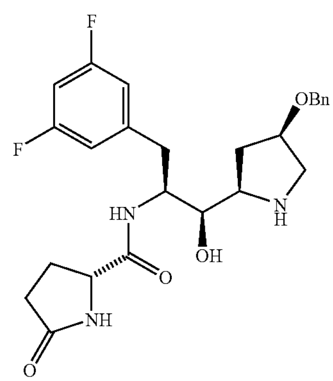 | $t_R$ = 3.58 min; 474 (M + H)⁺ |
| 11C | 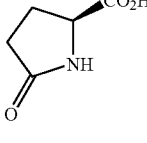 | 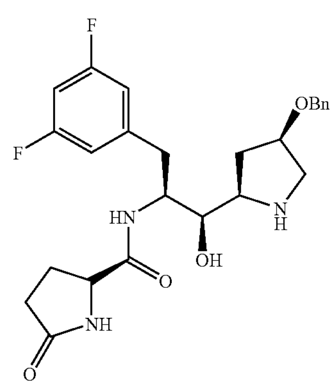 | $t_R$ = 3.64 min; 474 (M + H)⁺ |
| 11D | 2B | 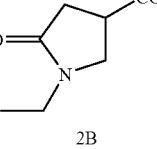 | $t_R$ = 3.85 min; 502 (M + H)⁺ |

| Ex. | Preparation | Structure | LCMS (Conditions A) |
|---|---|---|---|
| 11E | 2C | 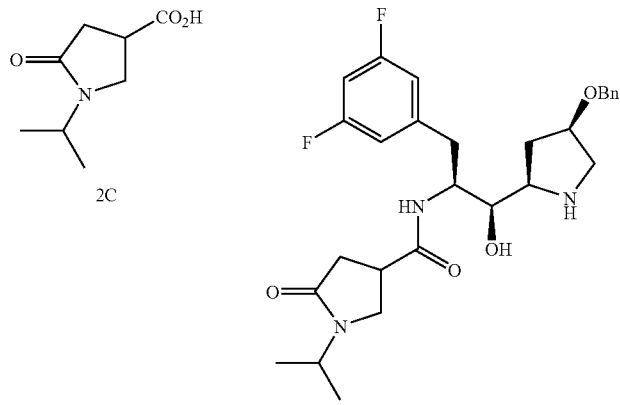 | $t_R$ = 3.98 min; 516 (M + H)$^+$ |
| 11F | 2D | 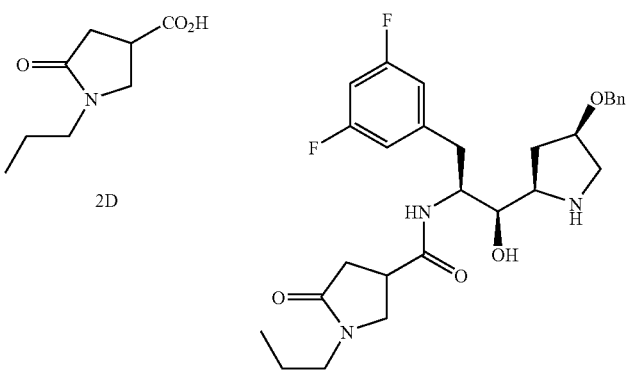 | $t_R$ = 4.00 min; 516 (M + H)$^+$ |
| 11G | 2E | 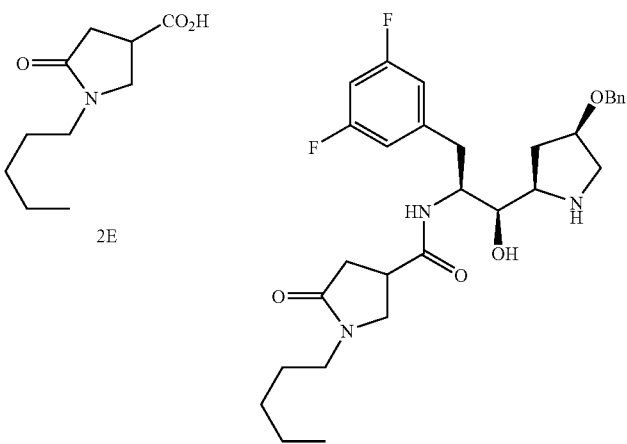 | $t_R$ = 3.67 min; 544 (M + H)$^+$ |

-continued

| Ex. | Preparation | Structure | LCMS (Conditions A) |
|---|---|---|---|
| 11H | 2F | 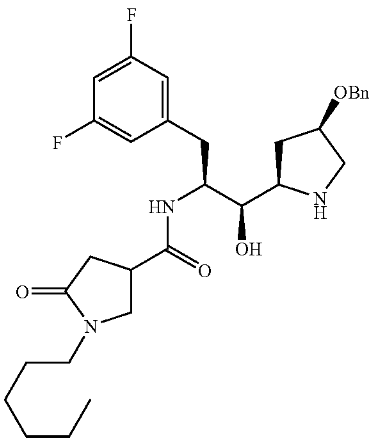 | $t_R$ = 3.74 min; 558 (M + H)$^+$ |
| 11I | 2G | 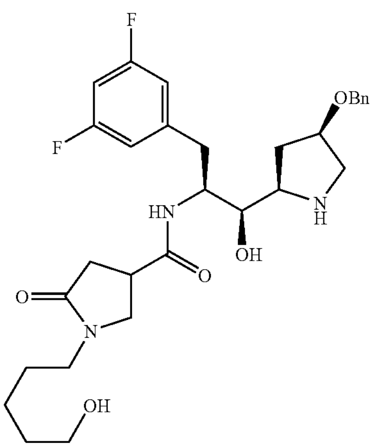 | $t_R$ = 2.91 min; 560 (M + H)$^+$ |
| 11J | 2H | 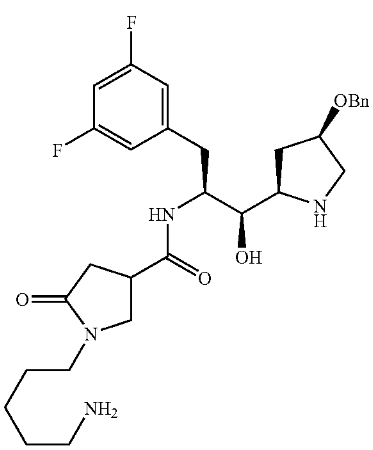 | $t_R$ = 2.66 min; 559 (M + H)$^+$ |

| Ex. | Preparation | Structure | LCMS (Conditions A) |
|---|---|---|---|
| 11K | 2I | 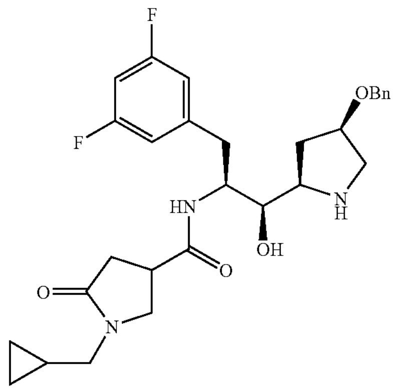 | $t_R$ = 3.21 min; 528 (M + H)$^+$ 3.29 min; 528 (M + H)$^+$ |
| 11L | 2J | 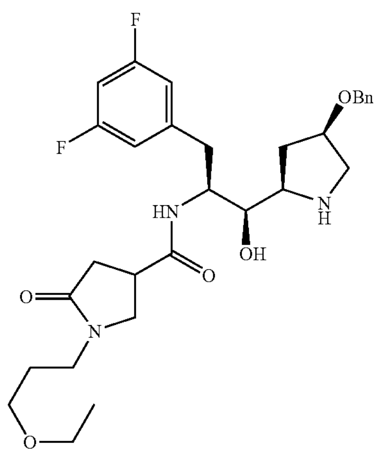 | $t_R$ = 3.06 min; 560 (M + H)$^+$ |
| 11M | 2K | 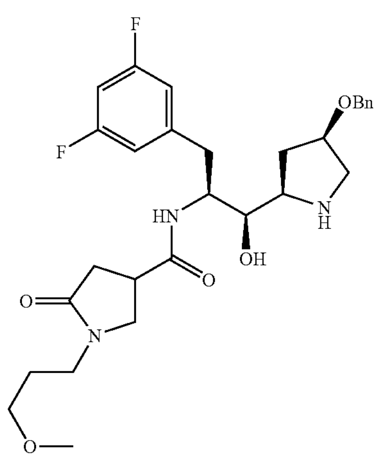 | $t_R$ = 2.71 min; 546 (M + H)$^+$ |

-continued

| Ex. | Preparation | Structure | LCMS (Conditions A) |
|---|---|---|---|
| 11N | 2L | 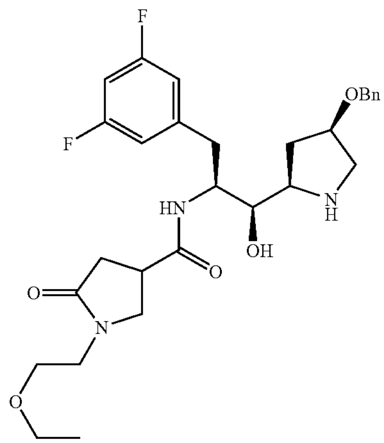 | $t_R$ = 3.30 min; 546 (M + H)$^+$ 3.38 min; 546 (M + H)$^+$ |
| 11O | 2M | 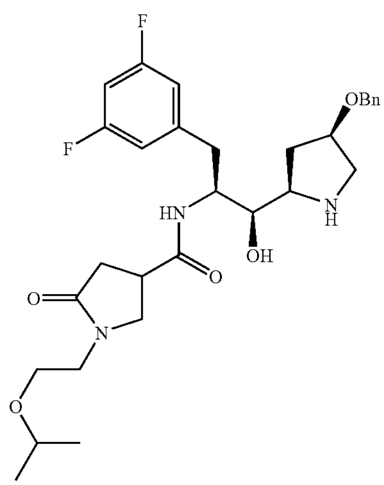 | $t_R$ = 3.31 min; 560 (M + H)$^+$ |
| 11P | 2N | 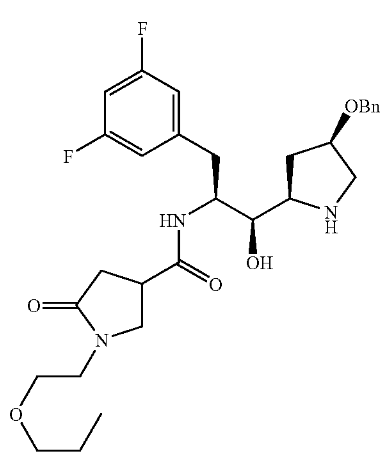 | $t_R$ = 3.32 min; 560 (M + H)$^+$ |

-continued

| Ex. | Preparation | Structure | LCMS (Conditions A) |
|---|---|---|---|
| 11Q | 2O | 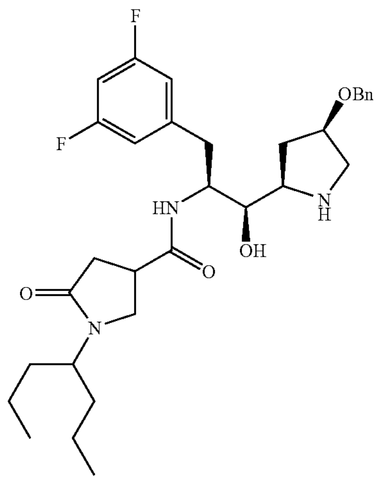 | $t_R$ = 3.97 min; 572 (M + H)$^+$ |
| 11R | 2P | 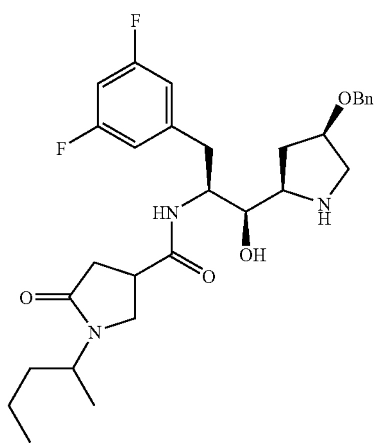 | $t_R$ = 3.24 min; 544 (M + H)$^+$ |
| 11S | 12 | 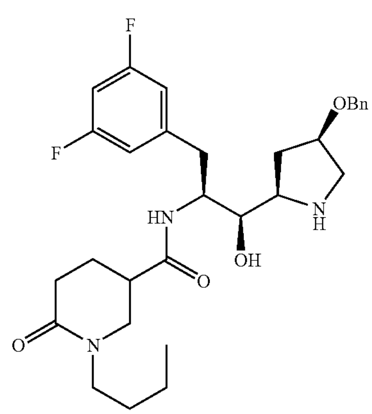 | $t_R$ = 4.28 min; 544 (M + H)$^+$ |

| Ex. | Preparation | Structure | LCMS (Conditions A) |
|---|---|---|---|
| 11T | 2Q 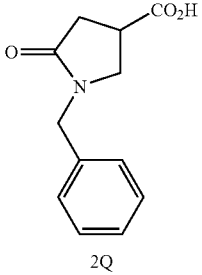 | 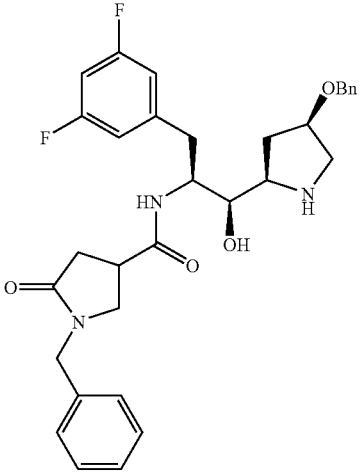 | $t_R$ = 4.25 min; 564 (M + H)$^+$ |
| 11U | 2R 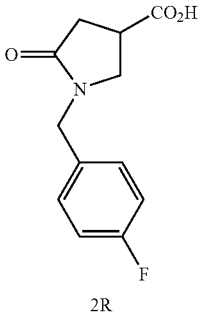 | 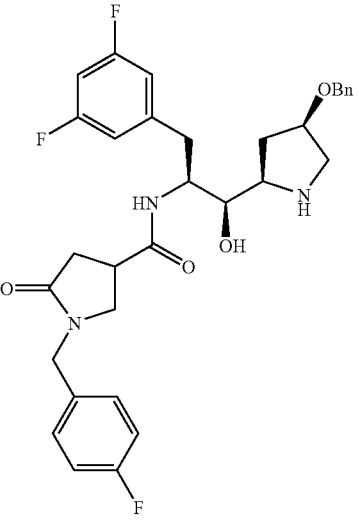 | $t_R$ = 3.55 min; 582 (M + H)$^+$ |
| 11V | 2S 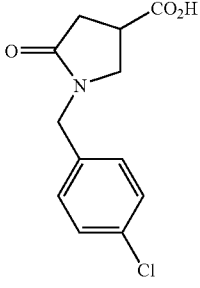 | 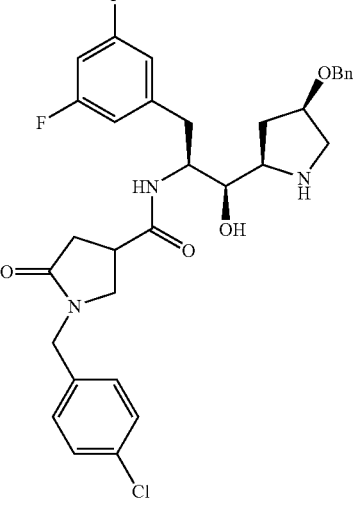 | $t_R$ = 3.39 min; 599 (M + H)$^+$ |

-continued

| Ex. | Preparation | Structure | LCMS (Conditions A) |
|---|---|---|---|
| 11W | 2T | 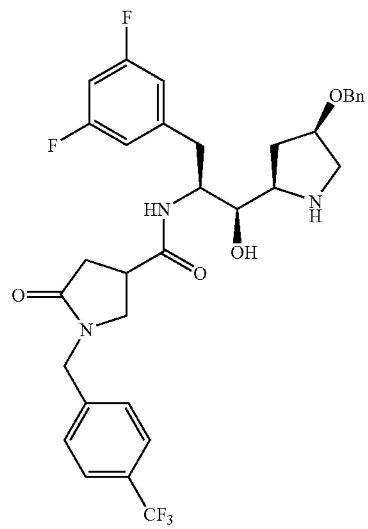 | $t_R$ = 3.54 min; 632 (M + H)$^+$ |
| 11X | 2U | 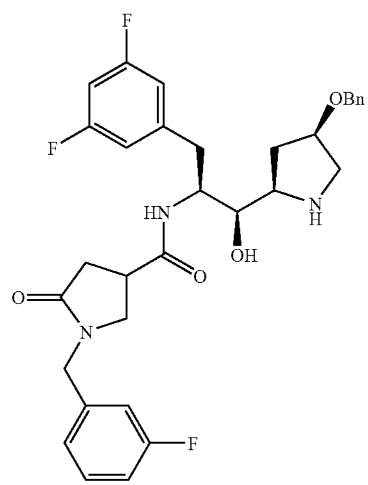 | $t_R$ = 3.26 min; 582 (M + H)$^+$ |
| 11Y | 2V | 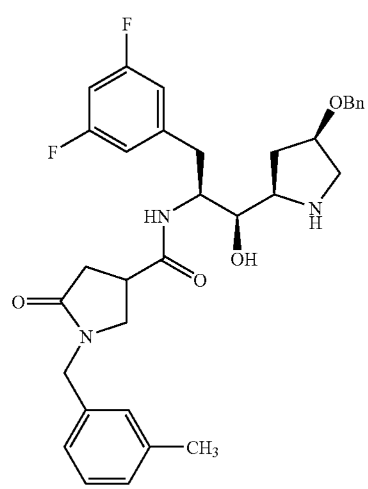 | $t_R$ = 3.60 min; 578 (M + H)$^+$ $t_R$ = 3.67 min; 578 (M + H)$^+$ |

| Ex. | Preparation | Structure | LCMS (Conditions A) |
|---|---|---|---|
| 11Z | 2W | 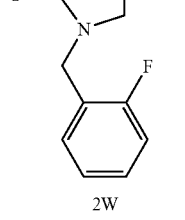 | $t_R$ = 3.20 min; 582 (M + H)$^+$ $t_R$ = 3.25 min; 582 (M + H)$^+$ |
| 11AA | 2X | 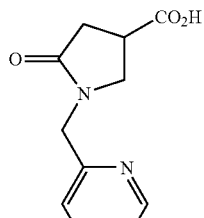 | $t_R$ = 2.64 min; 565 (M + H)$^+$ $t_R$ = 2.65 min; 565 (M + H)$^+$ |
| 11BB | 2Y | 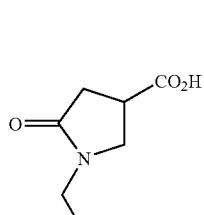 | $t_R$ = 2.51 min; 565 (M + H)$^+$ |

| Ex. | Preparation | Structure | LCMS (Conditions A) |
|---|---|---|---|
| 11CC | 2Z | 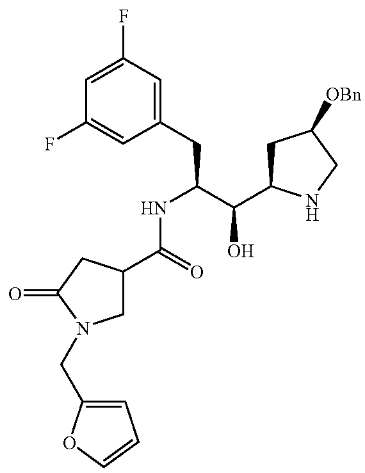 | $t_R$ = 3.36 min; 554 (M + H)$^+$ 3.41 min; 554 (M + H)$^+$ |
| 11DD | 2AA | 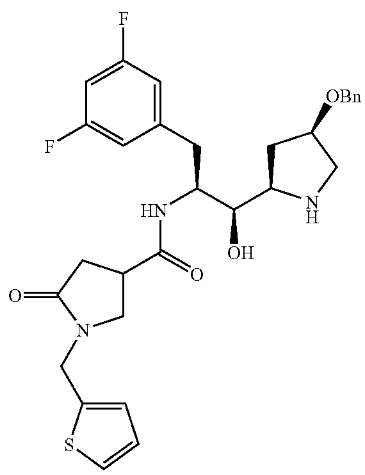 | $t_R$ = 3.47 min; 570 (M + H)$^+$ |
| 11EE | 2BB | 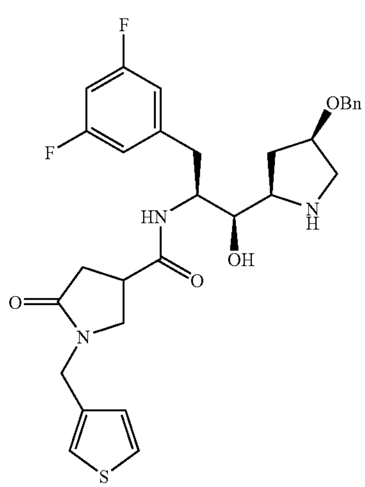 | $t_R$ = 3.46 min; 570 (M + H)$^+$ |

| Ex. | Preparation | Structure | LCMS (Conditions A) |
|---|---|---|---|
| 11FF | 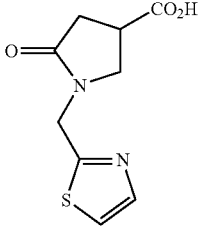<br>2CC | 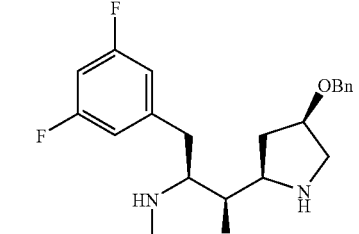 | $t_R$ = 3.05 min;<br>571 (M + H)$^+$ |
| 11GG | <br>2DD | 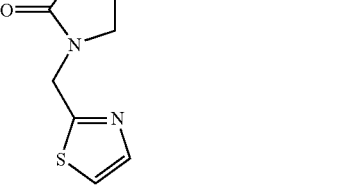 | $t_R$ = 3.40 min;<br>638 (M + H)$^+$<br>3.45 min; 638<br>(M + H)$^+$ |
| 11HH | 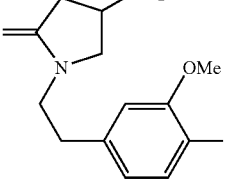<br>2EE | 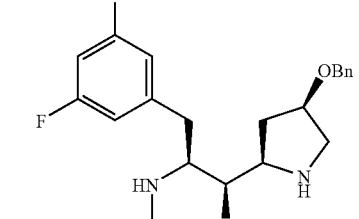 | $t_R$ = 3.82 min;<br>613 (M + H)$^+$<br>3.89 min; 613<br>(M + H)$^+$ |

| Ex. | Preparation | Structure | LCMS (Conditions A) |
|---|---|---|---|
| 11II | 3A 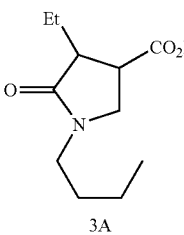 | 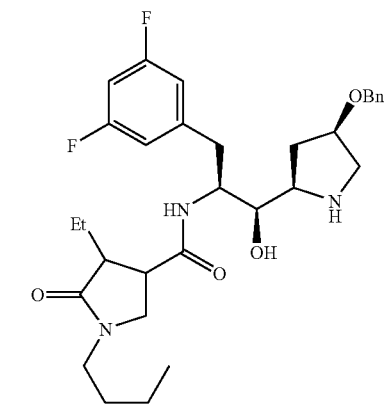 | $t_R$ = 3.61 min; 558 (M + H)$^+$ |
| 11JJ | 3B 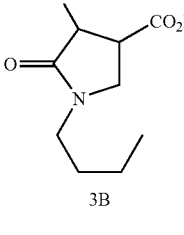 | 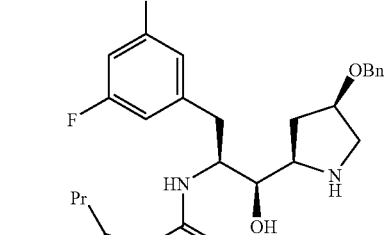 | $t_R$ = 3.72 min; 572 (M + H)$^+$ |
| 11KK | 3C 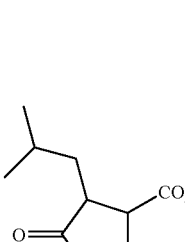 | 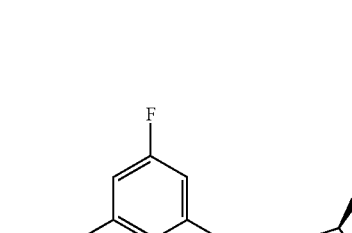 | $t_R$ = 4.54 min; 586 (M + H)$^+$ |

| Ex. | Preparation | Structure | LCMS (Conditions A) |
|---|---|---|---|
| 11LL | 3D | 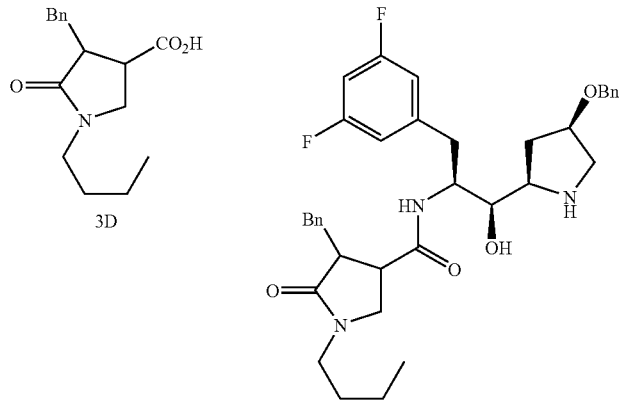 | $t_R$ = 4.64 min; 621 (M + H)$^+$ |
| 11MM | 3H | 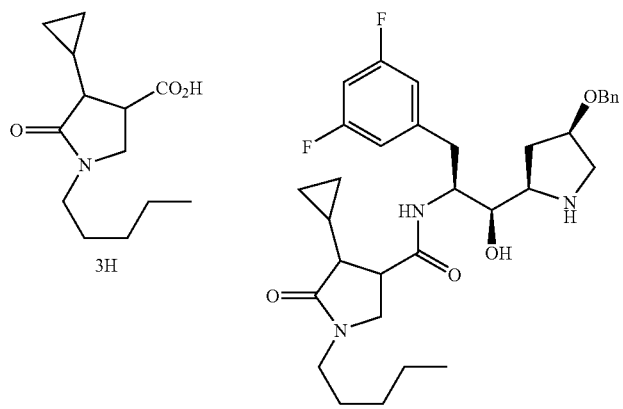 | $t_R$ = 3.38 min; 584 (M + H)$^+$ |
| 11NN | 3I | 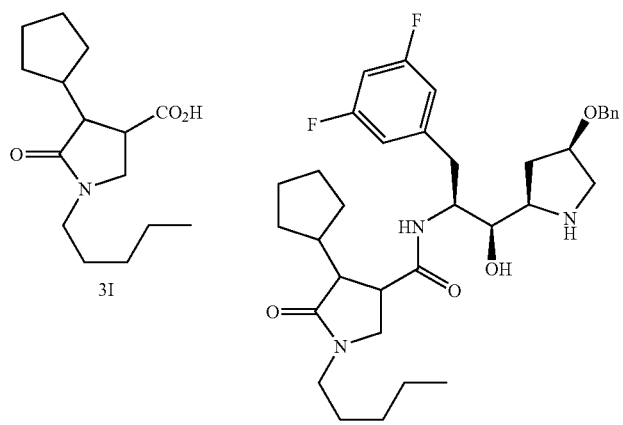 | $t_R$ = 3.65 min; 612 (M + H)$^+$ |

| Ex. | Preparation | Structure | LCMS (Conditions A) |
|---|---|---|---|
| 11OO | 3E | 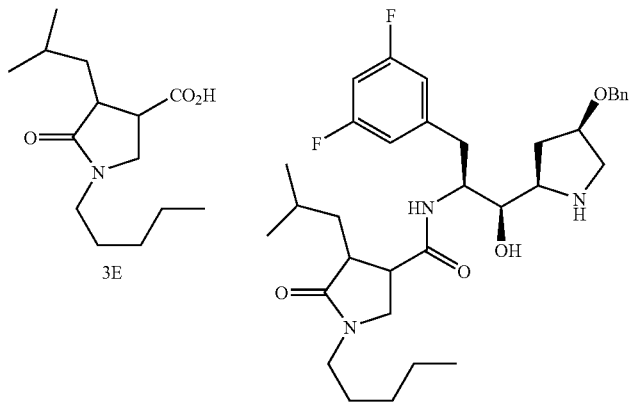 | $t_R$ = 3.63 min; 600 (M + H)$^+$ |
| 11PP | 3J | 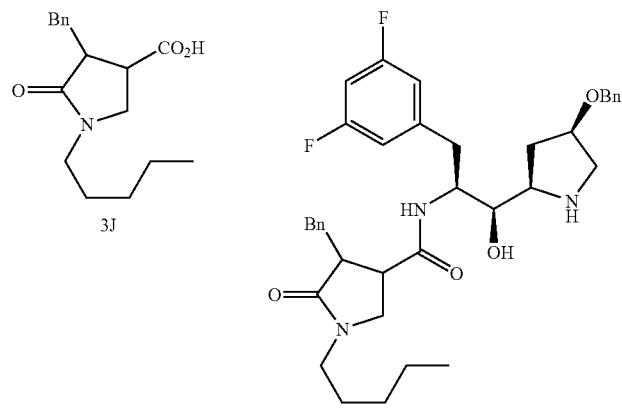 | $t_R$ = 4.02 min; 634 (M + H)$^+$ |
| 11QQ | 5A | 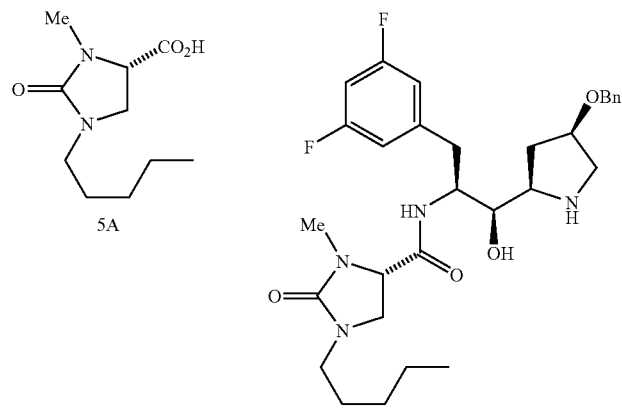 | $t_R$ = 3.65 min; 559 (M + H)$^+$ |

-continued
| Ex. | Preparation | Structure | LCMS (Conditions A) |
|---|---|---|---|
| 11RR | 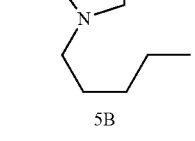 5B | 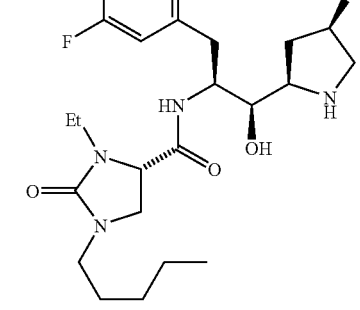 | $t_R$ = 3.46 min; 573 (M + H)$^+$ |
| 11SS | 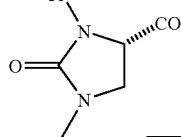 5C | 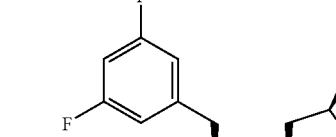 | $t_R$ = 3.88 min; 587 (M + H)$^+$ |
| 11TT | 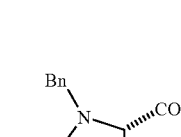 5D | 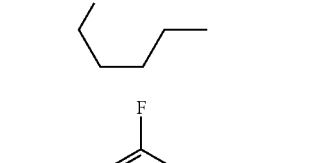 | $t_R$ = 4.50 min; 635 (M + H)$^+$ |
| 11UU |  5E | 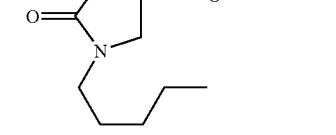 | $t_R$ = 3.33 min; 565 (M + H)$^+$ |

| Ex. | Preparation | Structure | LCMS (Conditions A) |
|---|---|---|---|
| 11VV | 5F | 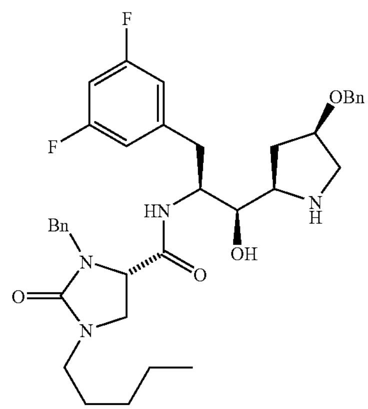 | $t_R$ = 4.32 min; 621 (M + H)$^+$ |
| 11WW | 6 | 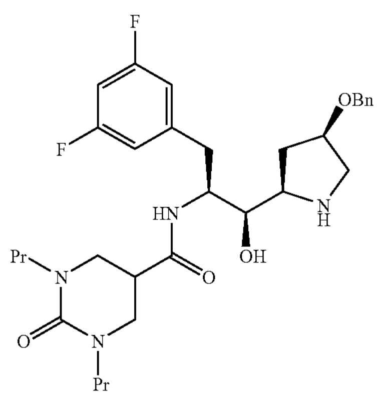 | $t_R$ = 3.46 min; 573 (M + H)$^+$ |

Example 12A

Step 1:

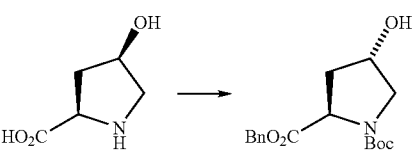

Cis-4-hydroxy-D-proline was converted into (4R)-(1-tert-butoxycarbonyl)-4-hydroxy-D-proline benzyl ester based on the procedure reported for the synthesis of (4S)-1-tert-butoxycarbonyl)-4-hydroxy-L-proline benzyl ester from cis-4-hydroxy-L-proline (Webb et al. *J. Org. Chem.* (1991), 56, 3009-3016). Mitsunobu inversion to give (4S)-1-(tert-butoxycarbonyl)-4-hydroxy-D-proline benzyl ester was adapted from the reported procedure (Lowe et al. *J. Chem. Soc. Perkin Trans.* 1 (1997), 539-546) for the synthesis of (4S)-1-tert-butoxycarbonyl)-4-hydroxy-D-proline methyl ester from (4R)-1-(tert-butoxycarbonyl)-4-hydroxy-D-proline methyl ester.

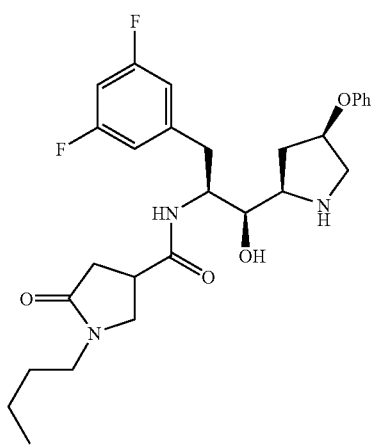

Step 2:

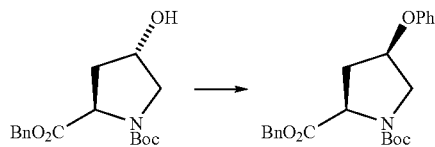

(4S)-1-(tert-butoxycarbonyl)-4-hydroxy-D-proline benzyl ester was converted into (4R)-1-(tert-butoxycarbonyl)-4-phenoxy-D-proline benzyl ester based on the reported protocol (Bellier et al. *J. Med. Chem.* (1997), 40, 3947-3956) for the corresponding methyl ester.

Step 3:

The product of Step 2 was converted to Example 12A in analogy to the procedure of Example 2A, except that Preparation 2A was used in place of Preparation 3A. LCMS (conditions A): $t_R$ (isomer 1)=3.23 min, m/e 516 $(M+H)^+$; $t_R$ (isomer 2)=3.36 min, m/e 516 $(M+H)^+$.

Using the appropriate carboxylic acid, the following Examples were prepared.

| Example | Preparation | Structure | LCMS (Conditions A) |
|---|---|---|---|
| 12B | 3H | 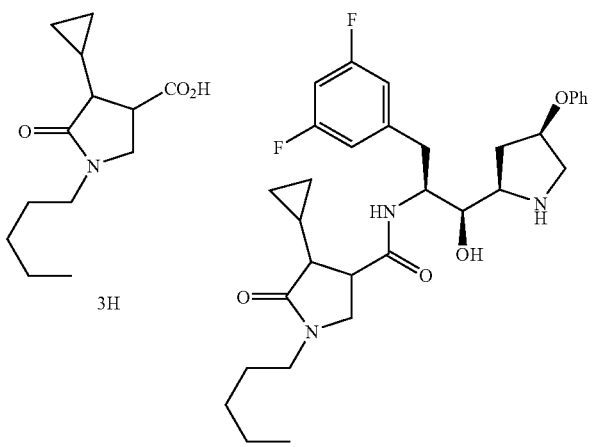 | $t_R$ = 3.32 min; 570 (M + H)$^+$ |
| 12C | 3I | 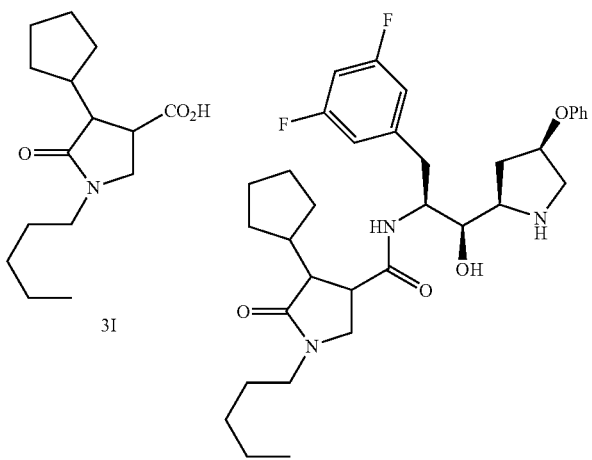 | $t_R$ = 3.60 min; 598 (M + H)$^+$ |

| Example | Preparation | Structure | LCMS (Conditions A) |
|---|---|---|---|
| 12D | 3E | 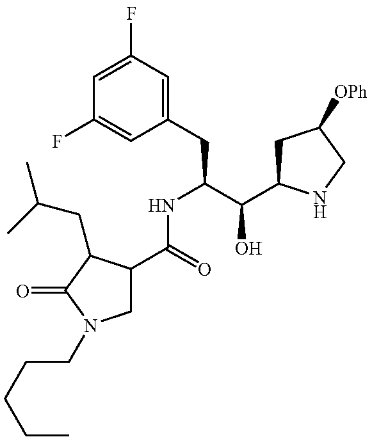 | $t_R$ = 3.94 min; 586 (M + H)$^+$ |
| 12E | 3J | 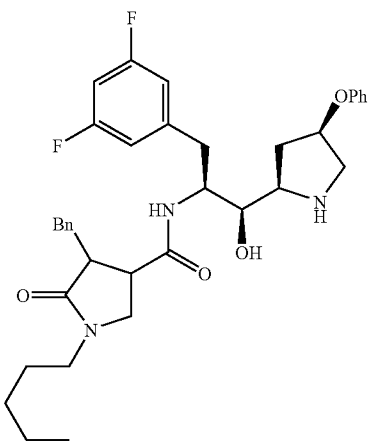 | $t_R$ = 3.69 min; 620 (M + H)$^+$ |
| 12F | 3F | 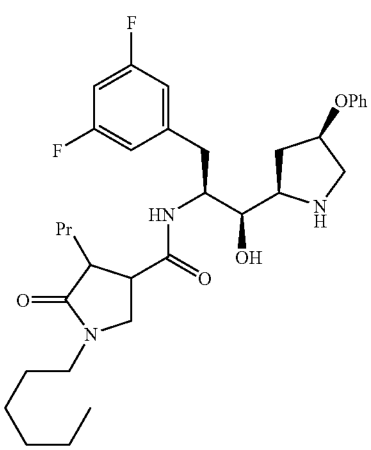 | $t_R$ = 3.74 min; 586 (M + H)$^+$ |

-continued

| Example | Preparation | Structure | LCMS (Conditions A) |
|---|---|---|---|
| 12G | 3G | 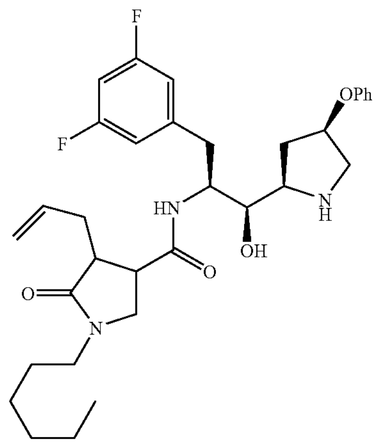 | $t_R$ = 3.92 min; 584 (M + H)$^+$ 3.99 min; 584 (M + H)$^+$ |
| 12H | 2J | 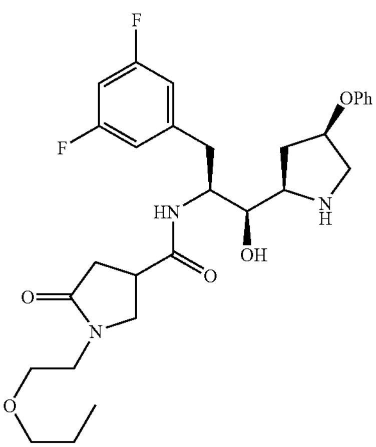 | $t_R$ = 3.21 min; 546 (M + H)$^+$ |
| 12I | 6 | 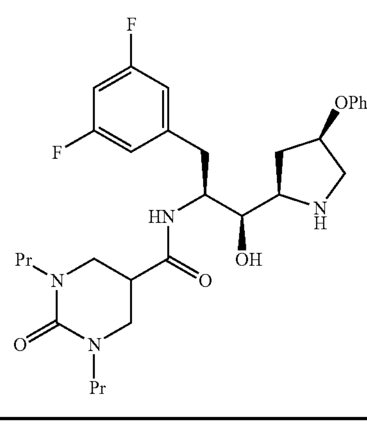 | $t_R$ = 3.44 min; 559 (M + H)$^+$ |

Example 13A

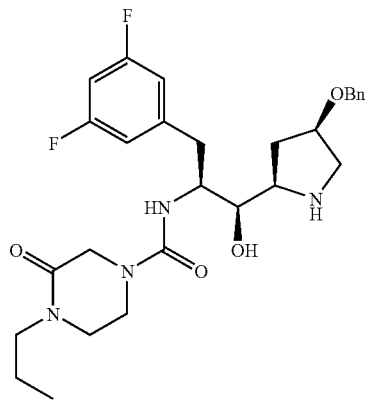

Step 1:

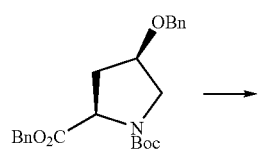

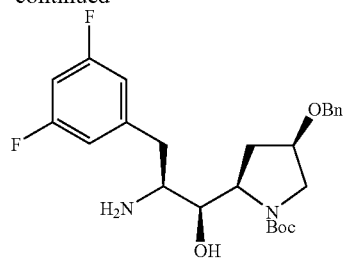

(4R)-1-tert-butoxycarbonyl-4-benzyloxy-D-proline benzyl ester (Bellier et al. *J. Med. Chem.* (1997), 40, 3947-3956) was converted into the product in analogy to the procedure of Example 2A, Steps 1 through 5, except that (4R)-1-tert-butoxycarbonyl-4-benzyloxy-D-proline benzyl ester was used in place of methyl N-Boc-D-1,2,3,4-tetrahydroquinoline-3-carboxylate. LCMS (Conditions A) $t_R$=4.84 min: m/e 925 (2M+H)—, 463 (M+H)$^+$, 407 (M-tBu+H), 363 (M-Boc+H)$^+$.

Step 2:

Preparation 7 (40 mg) and Et$_3$N (0.05 ml) was added to a stirred solution of the product of Step 1 (10 mg) in CH$_2$Cl$_2$ (1 ml). After 24 h, the reaction mixture was concentrated and the residue was subjected to HPLC (Conditions B) to give the coupled product. Deprotection of the coupled product in analogy to the procedure of Example 5A, Step 6 gave the product. LCMS (Conditions A) $t_R$=3.21 min; 531 (M+H)$^+$.

In analogy to Example 13A, using the appropriate Preparations and intermediates, the following Examples were prepared:

| Ex. | Preparation | Structure | LCMS (Conditions A) |
|---|---|---|---|
| 13B | 8 | 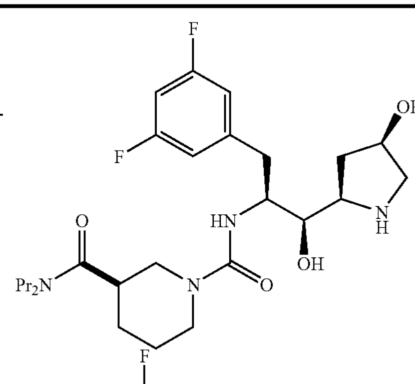 | $t_R$ = 3.87 min; 601 (M + H)$^+$ |
| 13C | 9 | 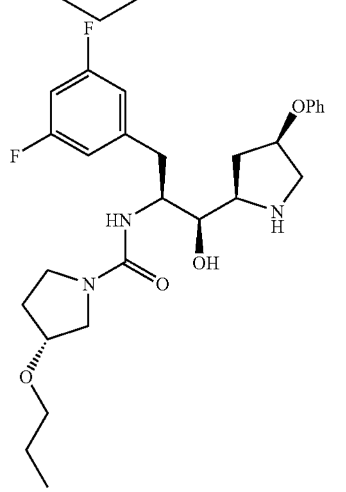 | $t_R$ = 3.60 min; 518 (M + H)$^+$ |

| Ex. | Preparation | Structure | LCMS (Conditions A) |
|---|---|---|---|
| 13D | 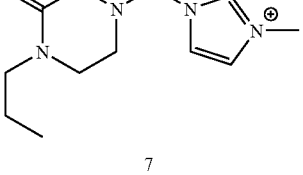 7 | 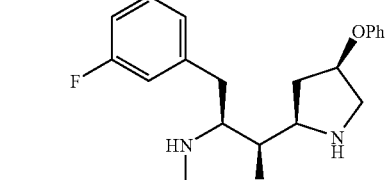 | $t_R$ = 3.17 min; 517 (M + H)$^+$ |
| 13E |  8 | 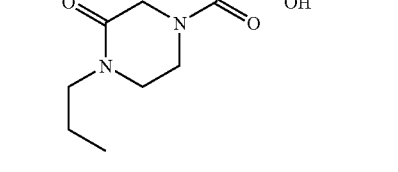 | $t_R$ = 3.81 min; 587 (M + H)$^+$ |
| 13F | 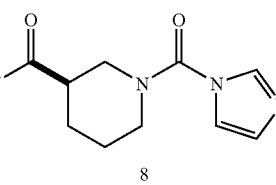 9 | 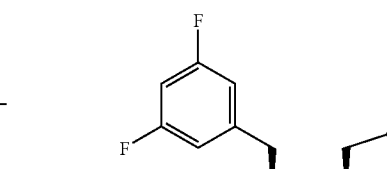 | $t_R$ = 3.55 min; 504 (M + H)$^+$ |
| 13G |  9 | 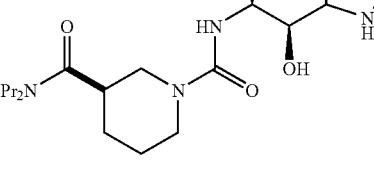 | $t_R$ = 3.68 min; 531 (M + H)$^+$ |

Example 14A

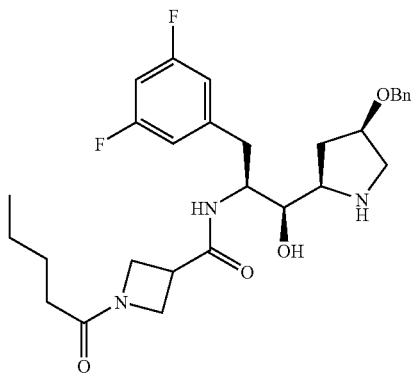

Step 1:

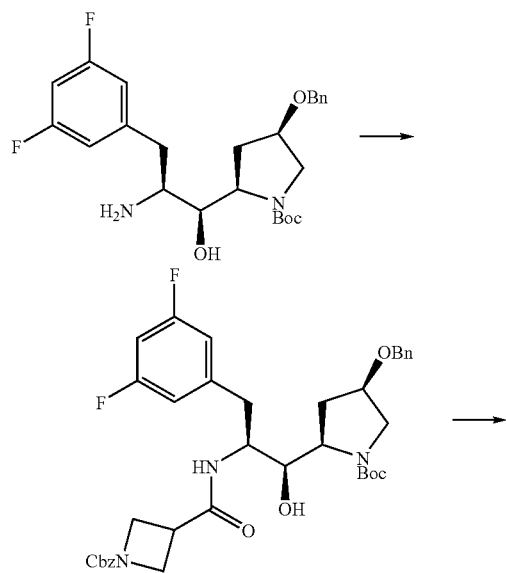

A mixture of (N-benzyloxycarbonyl)azetidine-3-carboxylic prepared according to Macdonald et al., *J. Med. Chem.*, (2002); 45, 3878 (325 mg, 1.38 mmol), and the product of Example 13A, Step 1 (320 mg, 0.69 mmol), HOAt (330 mg, 2.42 mmol), HATU (790 mg, 2.08 mmol), and Et$_3$N (580 μl, 4.15 mmol) in DMF (8 ml) was stirred at RT for 16 h. The mixture was partitioned between EtOAc and water, and the organic layer was washed with water and sat'd NaCl, dried (MgSO$_4$), concentrated, and purified by chromatography (SiO$_2$, 0-2% MeOH/CH$_2$Cl$_2$) to give the coupled product (402 mg, 86%): LCMS (Conditions A) t$_R$=4.99 min, m/e 680 (M+H). The coupled product (220 mg, 0.323 mmol) and 20% Pd(OH)$_2$/C (20 mg) in EtOH (11 ml) was stirred under 50 psi H$_2$, and the mixture was filtered after completion of the reaction as monitored by TLC. The resulting residue was subjected to PTLC (8% (2M NH$_3$/MeOH)/CH$_2$Cl$_2$) to give the product. LCMS (Conditions A): t$_R$=4.49 min: m/e 546 (M+H), 490 (M-$^t$Bu+H), 446 (M-Boc+H).

Step 2:

The product of Step 1 was coupled with pentanoic acid by essentially the procedure of Example 5A, Step 5. The coupled product was subjected to TFA in analogy to Example 5A, Step 6, to give the product. LCMS (conditions A) t$_R$=4.90 min: MS m/e 580 (M+H), 562 (M−H$_2$O+H).

Using the appropriate carboxylic acid, the following Examples were prepared from the product of Example 14, Step 1.

| Ex. | Carboxylic Acid | Structure | LCMS (Conditions A) |
|---|---|---|---|
| 14B | 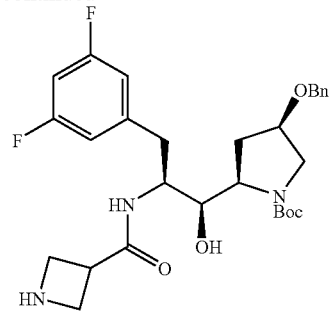 | 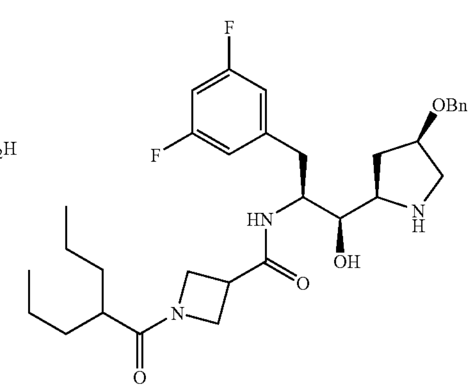 | t$_R$ = 4.59 min; 572 (M + H)$^+$ |

-continued

| Ex. | Carboxylic Acid | Structure | LCMS (Conditions A) |
|---|---|---|---|
| 14C | | 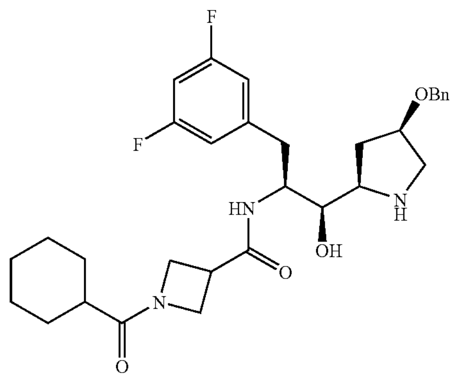 | $t_R$ = 4.33 min; 556 (M + H)$^+$ |
| 14D | | 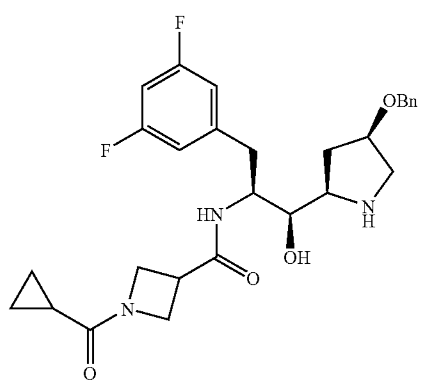 | $t_R$ = 4.08 min; 514 (M + H)$^+$ |
| 14E | | 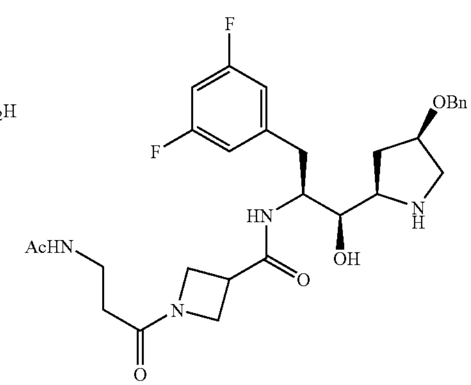 | $t_R$ = 3.42 min; 559 (M + H)$^+$ |

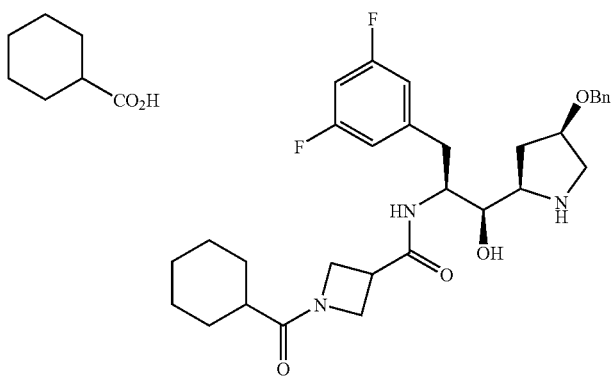

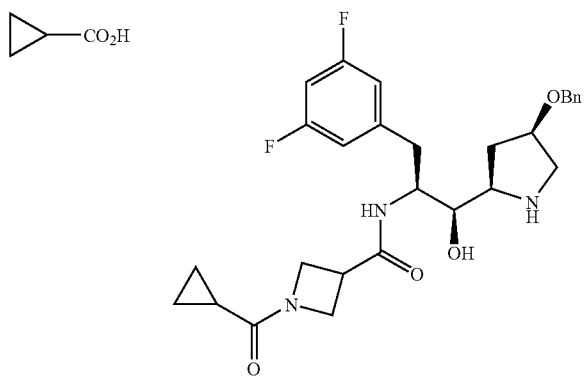

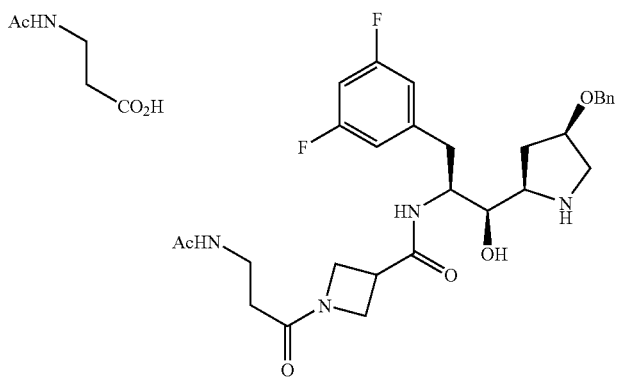

The following Examples were prepared by reaction of the product of Example 14, Step 1, with the appropriate sulfonyl chloride (1.2 equiv) and Et$_3$N (2.0 equiv) in CH$_2$Cl$_2$ at RT. Upon completion of the reaction, the reaction mixture was diluted with CH$_2$Cl$_2$/water, washed with brine (1×), and the organic layer dried (MgSO$_4$), and concentrated. Treatment of the residue with TFA in analogy to the procedure of Example 5A, Step 6, gave the products.

| Ex. | Sulfonyl Chloride | Structure | LCMS (Conditions A) |
|---|---|---|---|
| 14F | (butyl-SO₂Cl) | (structure) | $t_R$ = 4.34 min; 567 (M + H)⁺ |
| 14G | (propyl-SO₂Cl) | (structure) | $t_R$ = 4.17 min; 552 (M + H)⁺ |
| 14H | MeSO₂Cl | (structure) | $t_R$ = 3.86 min; 524 (M + H)⁺ |

Example 15A

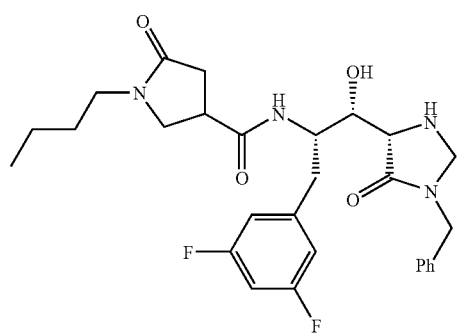

Step 1:

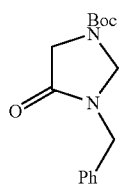

To a RT solution of 3-benzyl-4-imidazolidinone (1.07 g, 6.07 mmol), prepared according to Pinza, et al. *Liebigs Ann. Chem.* (1988), 993, in CH₂Cl₂ (80 ml) was added Et₃N (7 drops) and Boc₂O (1.39 g, 6.38 mmol). After 20 h, the reaction mixture was diluted with water and stirred vigorously for 10 min. The phases were separated, and the aqueous phase was extracted with CH₂Cl₂ (2×). The organic portions were combined, washed with brine, dried over MgSO₄, filtered and concentrated. The crude residue was purified by chromatography (silica, 0→50% EtOAc/hexanes) to give the desired product (1.37 g, 82%).
Step 2:

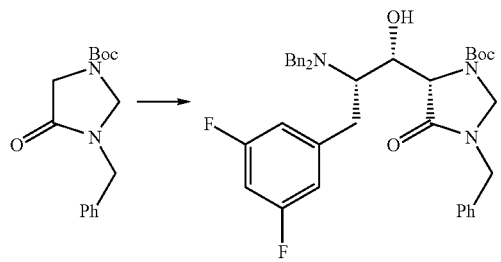

To a −78° C. solution of diisopropylamine (0.17 ml, 1.20 mmol) in THF (1 ml) was added n-BuLi (1.55 M in hexanes, 0.74 ml, 1.15 mmol). After 5 min, the mixture was warmed to 0° C., and after an additional 20 min, it was cooled back to −78° C. To this mixture was added a −78° C. solution of the product of Step 1 (304 mg, 1.10 mmol) in THF (3.5 ml). The resulting mixture was stirred at −78° C. for 1 h. At that time, a −78° C. solution of the product of Preparation 14 (366 mg, 1.00 mmol) in THF (2 ml) was added. The resulting mixture was stirred for 1.5 h at −78° C. and then was diluted with water and Et₂O. After warming to RT, the phases were separated, and the aqueous phase was extracted with Et₂O (3×). The organic portions were combined, washed with brine, dried over MgSO₄, filtered and concentrated. The crude residue was purified by chromatography (silica, 0→65% EtOAc/hexanes) to give the desired product (288 mg, 45%).
Step 3:

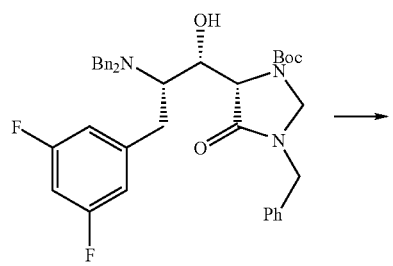

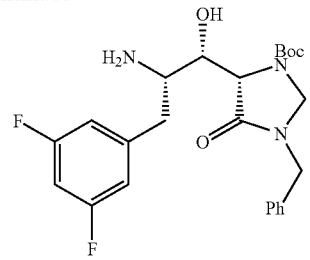

A flask was charged with the product of Step 2 (325 mg, 0.506 mmol), EtOAc (10 ml), AcOH (0.050 ml) and Pd(OH)₂/C (200 mg). The flask was evacuated and re-filled with H₂ from a balloon (7×) and then kept under H₂ balloon pressure. After 20 h, additional Pd(OH)₂/C (100 mg) was added followed by AcOH (0.050 ml). After an additional 6 h, the mixture was filtered through Celite with copious EtOAc washes, and the resulting filtrate was concentrated. The crude residue was purified by chromatography (silica, 0→15% 7N NH₃/MeOH in CH₂Cl₂) followed by PTLC (5% 7N NH₃/MeOH in CH₂Cl₂) to give the desired product (87 mg, 37%).
$^1$H NMR (400 MHz, CDCl₃) δ 7.28 (m, 5H), 6.76-6.63 (m, 3H), 4.72-4.38 (m, 5H), 3.95 (d, J=8.8 Hz, 1H), 3.32 (br d, J=13.2 Hz, 1H), 3.09 (m, 0.2H), 2.77 (m, 1H), 2.67 (m, 0.2H), 2.44 (dd, J=15.2, 10.0 Hz), 1.45 (s, 9H).
Step 4:

To a solution of Preparation 2A (13 mg, 0.072 mmol) and the product of Step 3 (30 mg, 0.065 mmol) in of DMF (1 ml) was added PyBOP (44 mg, 0.085 mmol) and DIEA (0.045 ml, 0.26 mmol). The mixture was stirred at RT for one day. It was diluted with EtOAc (1 ml) and hexane (1 ml). The mixture was washed with water (3×1 ml), the organic layer was dried (Na₂SO₄) and concentrated in vacuo. The residue was purified by chromatography (SiO₂, 70% EtOAc/hexane) to give coupled product (24 mg, 60%). This coupled product was treated with 4N HCl in dioxane (2 ml) for 30 min. The mixture was concentrated in vacuo to give product (26.3 mg, 100%).
$^1$H NMR (400 MHz, CD₃OD) δ 8.20 (m, 1H), 7.31 (m, 5H), 6.84 (m, 2H), 6.78 (m, 1H), 4.72-4.40 (m, 5H), 4.34 (m, 1H), 4.22 (m, 1H), 3.40 (m, 2H), 3.30-2.90 (m, 5H), 2.78 (m, 1H), 2.42 (m, 1H), 2.22 (m, 1H), 1.42 (m, 2H), 1.23 (m, 2H), 0.88 (t, J=7.6 Hz, 3H); LCMS $t_R$=3.18 min, 529 (M+H).

By essentially the same procedure set forth for Example 15A, and using the appropriate Preparations, the following compounds were prepared:

| Ex. | Preparation | Structure | LCMS (Conditions A) |
|---|---|---|---|
| 15B | 3A | 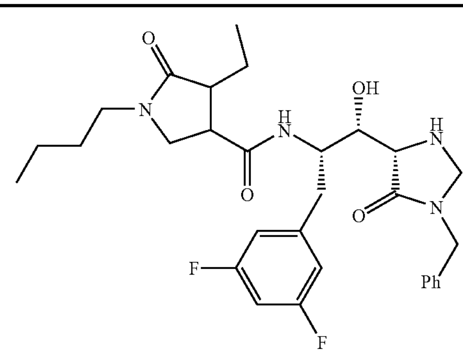 | $t_R$ = 3.35 min, 557 (M + H) |

| Ex. | Preparation | Structure | LCMS (Conditions A) |
|---|---|---|---|
| 15C | 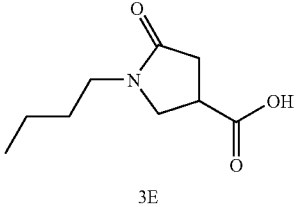<br>3E | 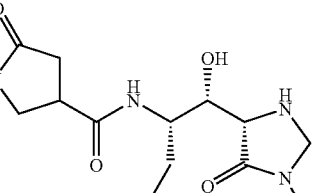 | $t_R$ = 3.38 min, 543 (M + H) |
| 15D | 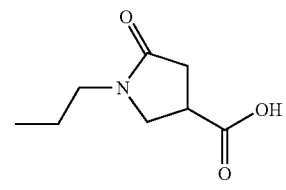<br>2D | 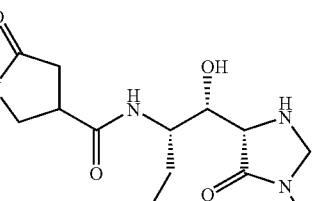 | $t_R$ = 2.97 min, 515 (M + H) |

BACE-1 Cloning, Protein Expression and Purification

A predicted soluble form of human BACE1 (sBACE1, corresponding to amino acids 1-454) was generated from the full length BACE1 cDNA (full length human BACE1 cDNA in pcDNA4/mycHisA construct; University of Toronto) by PCR using the advantage-GC cDNA PCR kit (Clontech, Palo Alto, Calif.). A HindIII/PmeI fragment from pcDNA4-sBACE1myc/His was blunt ended using Klenow and sub-cloned into the Stu I site of pFASTBACI(A) (Invitrogen). A sBACE1mycHis recombinant bacmid was generated by transposition in DH10Bac cells(GIBCO/BRL). Subsequently, the sBACE1mycHis bacmid construct was transfected into sf9 cells using CellFectin (Invitrogen, San Diego, Calif.) in order to generate recombinant baculovirus. Sf9 cells were grown in SF 900-II medium (Invitrogen) supplemented with 3% heat inactivated FBS and 0.5× penicillin/streptomycin solution (Invitrogen). Five milliliters of high titer plaque purified sBACEmyc/His virus was used to infect 1 L of logarithmically growing sf9 cells for 72 hours. Intact cells were pelleted by centrifugation at 3000×g for 15 minutes. The supernatant, containing secreted sBACE1, was collected and diluted 50% v/v with 100 mM HEPES, pH 8.0. The diluted medium was loaded onto a Q-sepharose column. The O-sepharose column was washed with Buffer A (20 mM HEPES, pH 8.0, 50 mM NaCl).

Proteins, were eluted from the Q-sepharose column with Buffer B (20 mM HEPES, pH 8.0, 500 mM NaCl). The protein peaks from the Q-sepharose column were pooled and loaded onto a Ni-NTA agarose column. The Ni-NTA column was then washed with Buffer C (20 mM HEPES, pH 8.0, 500 mM NaCl). Bound proteins were then eluted with Buffer D (Buffer C+250 mM imidazole). Peak protein fractions as determined by the Bradford Assay (Biorad, Calif.) were concentrated using a Centricon 30 concentrator (Millipore). sBACE1 purity was estimated to be 90% as assessed by SDS-PAGE and Commassie Blue staining. N-terminal sequencing indicated that greater than 90% of the purified sBACE1 contained the prodomain; hence this protein is referred to as sproBACE1.

Peptide Hydrolysis Assay

The inhibitor, 25 nM EuK-biotin labeled APPsw substrate (EuK-KTEEISEVNLDAEFRHDKC-biotin; CIS-Bio International, France), 5 µM unlabeled APPsw peptide (KTEEISEVNLDAEFRHDK; American Peptide Company, Sunnyvale, Calif.), 7 nM sproBACE1, 20 mM PIPES pH 5.0, 0.1% Brij-35 (protein grade, Calbiochem, San Diego, Calif.), and 10% glycerol were preincubated for 30 min at 30° C. Reactions were initiated by addition of substrate in a 5 µl aliquot resulting in a total volume of 25 µl. After 3 hr at 30° C. reactions were terminated by addition of an equal volume of 2× stop buffer containing 50 mM Tris-HCl pH 8.0, 0.5 M KF, 0.001% Brij-35, 20 g/ml SA-XL665 (cross-linked allophycocyanin protein coupled to streptavidin; CIS-Bio International, France) (0.5 µg/well). Plates were shaken briefly and spun at 1200×g for 10 seconds to pellet all liquid to the bottom of the plate before the incubation. HTRF measurements were made on a Packard Discovery® HTRF plate reader using 337 nm laser light to excite the sample followed by a 50 µs delay and simultaneous measurements of both 620 nm and 665 nm emissions for 400 µs.

$IC_{50}$ determinations for inhibitors, (I), were determined by measuring the percent change of the relative fluorescence at 665 nm divided by the relative fluorescence at 620 nm, (665/620 ratio), in the presence of varying concentrations of I and a fixed concentration of enzyme and substrate. Nonlinear regression analysis of this data was performed using Graph- Pad Prism 3.0 software selecting four parameter logistic equation, that allows for a variable slope. Y=Bottom+(Top−Bottom)/(1+10^((LogEC50-X)*Hill Slope)); X is the logarithm of concentration of 1, Y is the percent change in ratio and Y starts at bottom and goes to top with a sigmoid shape.

Compounds of the present invention have an $IC_{50}$ range from about 0.1 to about 26,000 nM, preferably about 0.1 to about 1000 nM, more preferably about 0.1 to about 100 nM. Compounds of the preferred stereochemistry have $IC_{50}$ values in a range of about 0.1 to about 500 nM, preferably about 0.1 to about 100 nM. Example 5FF has as $IC_{50}$ of 1 nM.

In the aspect of the invention relating to a combination of a compound of formula I with a cholinesterase inhibitor, acetyl- and/or butyrylchlolinesterase inhibitors can be used. Examples of cholinesterase inhibitors are tacrine, donepezil, rivastigmine, galantamine, pyridostigmine and neostigmine, with tacrine, donepezil, rivastigmine and galantamine being preferred.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 100 mg, preferably from about 1 mg to about 50 mg, more preferably from about 1 mg to about 25 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 300 mg/day, preferably 1 mg/day to 50 mg/day, in two to four divided doses.

When a compound of formula I is used in combination with a β-secretase inhibitors other than those of formula I, an HMG-CoA reductase inhibitor, a gamma-secretase inhibitor, a non-steroidal anti-inflammatory agent, an N-methyl-D-aspartate receptor antagonist, a cholinesterase inhibitor or an anti-amyloid antibody to treat a cognitive disorder or neurodegenerative disorder, the active components may be co-administered simultaneously or sequentially, or a single pharmaceutical composition comprising a compound of formula I and one of the other agents in a pharmaceutically acceptable carrier can be administered. The components of the combination can be administered individually or together in any conventional oral or parenteral dosage form such as capsule, tablet, powder, cachet, suspension, solution, suppository, nasal spray, etc. The dosage of the β-secretase inhibitors other than those of formula I, HMG-CoA reductase inhibitor, gamma-secretase inhibitor, non-steroidal anti-inflammatory agent, N-methyl-D-aspartate receptor antagonist, cholinesterase inhibitor or anti-amyloid antibody can be determined from published material, and may range from 0.001 to 100 mg/kg body weight.

When separate pharmaceutical compositions of a compound of formula I and a β-secretase inhibitors other than those of formula I, an HMG-CoA reductase inhibitor, a gamma-secretase inhibitor, a non-steroidal anti-inflammatory agent, an N-methyl-D-aspartate receptor antagonist, a cholinesterase inhibitor or an anti-amyloid antibody are to be administered, they can be provided in a kit comprising in a single package, one container comprising a compound of formula I in a pharmaceutically acceptable carrier, and a separate container comprising the other agent in a pharmaceutically acceptable carrier, with the compound of formula I and the other agent being present in amounts such that the combination is therapeutically effective. A kit is advantageous for administering a combination when, for example, the components must be administered at different time intervals or when they are in different dosage forms.

The invention also includes multi-agent compositions, kits and methods of treatment, e.g., a compound of formula I can be administered in combination with an HMG-CoA reductase inhibitor and a non-steroidal anti-inflammatory agent.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

We claim:

1. A method of treating Alzheimer's disease disease comprising administering to a patient in need of such treatment an effective amount of a compound, or a pharmaceutically acceptable salt thereof, said compound having a structure according to Formula (I):

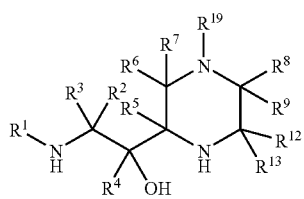

wherein:
R¹ is

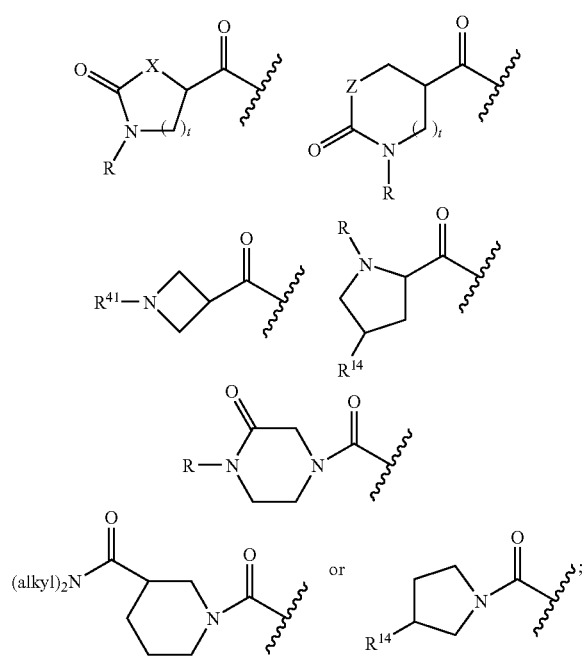

X is —O—, —C(R¹⁴)₂— or —N(R)—;
Z is —C(R¹⁴)₂— or —N(R)—;
t is 0, 1, 2 or 3;
each R is independently selected from the group consisting of H, alkyl, alkoxy, alkoxyalkyl, phenylalkyl, alkenyl, pyridylmethyl, furanylmethyl, thienylmethyl, thiazolylmethyl, cycloalkyl, and cycloalkylalkyl, wherein said alkyl, said alkoxy, said alkoxyalkyl, said phenylalkyl, said alkenyl, said pyridylmethyl, said furanylmethyl, said thienylmethyl, said thiazolylmethyl, said cycloalkyl, and said cycloalkylalkyl are unsubstituted or substituted by from 1 to 5 independently selected R³² groups;
R² is H, alkyl, phenyl, or phenylalkyl, wherein said phenyl and said phenylalkyl are unsubstituted or substituted by from 1 to 5 independently selected R³² groups;
R³ is H or alkyl;
R⁴ is H or alkyl;
R⁵ is H or alkyl;
each R¹⁴ is independently selected from the group consisting of H, alkyl, alkenyl, halo, —CN, haloalkyl, phenyl, phenylalkyl, cycloalkyl, and alkoxy;
R⁴¹ is alkyl, cycloalkyl, —SO₂(alkyl), —C(O)-alkyl, —C(O)-cycloalkyl or —alkyl—NH—C(O)CH₃;
R⁶ and R⁷ are independently selected from the group consisting of H and alkyl,
or R⁶ and R⁷, together with the ring carbon to which they are attached, form —C(O)—;
R⁸ and R⁹ are independently selected from the group consisting of H and alkyl,
or R⁸ and R⁹, together with the ring carbon to which they are attached, form —C(O)—;
R¹² and R¹³ are independently selected from the group consisting of H and alkyl, wherein said alkyl is unsubstituted or substituted by from 1 to 5 independently selected R³² groups,
or R¹² and R¹³, together with the ring carbon to which they are attached, form —C(O)—;
R¹⁸ is H, alkyl, phenyl, phenylalkyl, pyridyl, oxazolyl, pyrazinyl, thienyl, imidazolyl, pyridylalkyl, oxazolylalkyl, pyrazinylalkyl, thienylalkyl, or imidazolylalkyl,
wherein said alkyl, said phenyl, said phenylalkyl, said pyridyl, said oxazolyl, said pyrazinyl, said thienyl, said imidazolyl, said pyridylalkyl, said oxazolylalkyl, said pyrazinylalkyl, said thienylalkyl, and said imidazolylalkyl, are each unsubstituted or substituted by from 1 to 5 independently selected R³² groups;
R¹⁹ is H, alkyl, phenyl, phenylalkyl, pyridyl, oxazolyl, pyrazinyl, thienyl, imidazolyl, pyridylalkyl, oxazolylalkyl, pyrazinylalkyl, thienylalkyl, or imidazolylalkyl, —SOR¹⁸, —SO₂R¹⁸ or —CN, wherein said alkyl, said phenyl, said phenylalkyl, said pyridyl, said oxazolyl, said pyrazinyl, said thienyl, said imidazolyl, said pyridylalkyl, said oxazolylalkyl, said pyrazinylalkyl, said thienylalkyl, and said imidazolylalkyl, are each unsubstituted or substituted by from 1 to 5 independently selected R³² groups; and
each R³² group is independently selected from the group consisting of halo, alkyl, alkoxy, —OH, phenyl, phenoxy, phenylalkyl, —NO₂, —CN, haloalkyl, and haloalkoxy,
or two R³² groups on the same ring carbon atom are taken together to form =O.

2. The method of claim 1, wherein R³, R⁴ and R⁵ are hydrogen and R² is phenylalkyl, said phenylalkyl being unsubstituted or substituted by from 1 to 5 indepenendely selected R³² groups.

3. The method of claim 2, wherein R² is benzyl, wherein said benzyl is unsubstituted or substituted by from 1 to 5 independently selected R³² groups.

4. The method of claim 1, wherein R¹ is

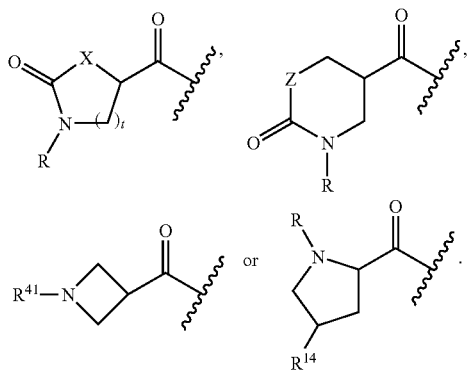

5. The method of claim 1, wherein $R^1$ is

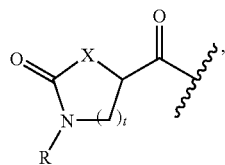

t is 1 and X is —$C(R^{14})_2$— or —N(R)—.

6. The method of claim 5, wherein X is —$C(R^{14})_2$—, $R^{14}$ is hydrogen, alkyl, alkenyl, cycloalkyl or benzyl, and R is alkyl, alkoxy, alkoxyalkyl, unsubstituted phenylalkyl, phenylalkyl which is substituted by 1 to 5 independently selected $R^{32}$ groups, alkenyl, cycloalkylalkyl, pyridylmethyl, furanylmethyl, thienylmethyl or thiazolylmethyl.

7. The method of claim 6, wherein said optionally substituted phenylalkyl is optionally substituted benzyl or optionally substituted phenylethyl, wherein the optional substituents are 1 or 2 $R^{32}$ groups independently selected from halo, alkyl, alkoxy and haloalkyl.

8. The method of claim 6, wherein R is alkyl, alkoxyalkyl or cycloalkylalkyl and one $R^{14}$ is hydrogen and the other is hydrogen or alkyl.

9. The method of claim 5, wherein X is —N(R)— and each R is independently selected from the group consisting of hydrogen, alkyl, alkoxyalkyl, cycloalkylalkyl and benzyl.

10. The method of claim 1, wherein $R^1$ is

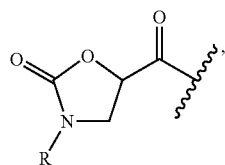

and R is hydrogen, alkyl, alkoxyalkyl, cycloalkylalkyl or benzyl.

11. The method of claim 1, wherein $R^1$ is

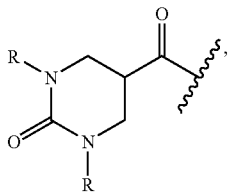

and each R is independently selected from the group consisting of hydrogen, alkyl, alkoxyalkyl, cycloalkylalkyl and benzyl; or $R^1$ is

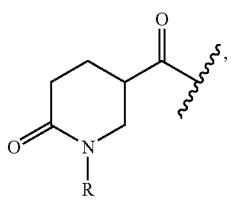

and R is hydrogen, alkyl, alkoxyalkyl, cycloalkylalkyl or benzyl; or $R^1$ is

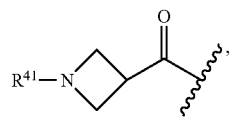

wherein $R^{41}$ is —C(O)-alkyl, —C(O)-cycloalkyl or —$SO_2$-alkyl; or $R^1$ is

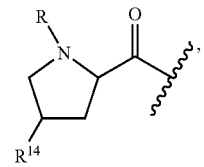

wherein R is hydrogen, alkyl, alkoxyalkyl, cycloalkylalkyl or benzyl and $R^{14}$ is alkoxy.

12. The method of claim 1, wherein $R^6$, $R^7$, $R^8$, $R^9$, $R^{12}$ and $R^{13}$ are each hydrogen, or $R^8$, $R^9$, $R^{12}$ and $R^{13}$ are each hydrogen and $R^6$ and $R^7$, together with the ring carbon to which they are attached, form —C(O)—.

13. The method of claim 12, wherein $R^{19}$ is optionally substituted alkyl, —$SO_2R^{18}$, pyridyl, oxazolyl, pyrazinyl, thienyl, or imidazolyl, wherein said pyridyl, said oxazolyl, said pyrazinyl, said thienyl, and said imidazolyl are unsubstituted or substituted by from 1 to 5 independently selected $R^{32}$ groups.

14. The method of claim 12, wherein $R^{19}$ is alkyl, benzyl, phenyl, pyridyl, oxazolyl, pyrazinyl, thienyl, or imidazolyl, wherein said benzyl, said phenyl, said pyridyl, said oxazolyl, said pyrazinyl, said thienyl, and said imidazolyl are unsubstituted or substituted by from 1 to 5 independently selected $R^{32}$ groups, —$SO_2$alkyl, —$SO_2$phenyl, —$SO_2$benzyl,
  wherein said optional 1 to 5 $R^{32}$ groups when present on phenyl are independently selected from the group consisting of halo, alkyl, phenyl, alkoxy, haloalkyl, phenoxy, and —CN;
  wherein said optional 1 to 5 $R^{32}$ groups when present on benzyl are independently selected from the group consisting of halo, alkyl, alkoxy, cyano and phenyl;
  and wherein said pyridyl, said oxazolyl, said pyrazinyl, said thienyl, and said imidazolyl (when present) are independently selected from alkyl, and halo.

15. The method of claim 1, wherein:
$R^5$ is H;
$R^6$ and $R^7$ are each H, or alternatively $R^6$ and $R^7$ are taken together with the ring carbon to which they are attached to form —C(O)—;
$R^8$ and $R^9$ are each H;
$R^{12}$ is H or alkyl;
$R^{13}$ is H; and
$R^{19}$ is —$SO_2R^{18}$, alkyl, pyridyl, oxazolyl, pyrazinyl, thienyl, or imidazolyl, wherein said alkyl, said pyridyl, said oxazolyl, said pyrazinyl, said thienyl, and said imidazolyl are unsubstituted or substituted by from 1 to 5 independently selected $R^{32}$ groups.

16. The method of claim 1, wherein $R^{19}$ is alkyl, phenylalkyl or —$SO_2R^{18}$.

17. The method of claim 1, wherein $R^{19}$ is phenylalkyl.

18. The method of claim 1, wherein $R^{19}$ is phenyl or fluorobenzyl.

19. The method of claim 1, wherein $R^{19}$ is —$SO_2R^{18}$ and $R^{18}$ is phenyl, pyridyl, thienyl or imidazolyl.

20. The method of claim 16, wherein $R^6$, $R^7$, $R^8$, $R^9$, $R^{12}$ and $R^{13}$ are each hydrogen.

21. The method of claim 16, wherein $R^8$, $R^9$, $R^{12}$ and $R^{13}$ are each hydrogen and $R^6$ and $R^7$, together with the ring carbon to which they are attached, form —C(O)—.

22. The method of claim 16, wherein $R^6$, $R^7$, $R^9$, and $R^{13}$ are each hydrogen; and $R^8$ and $R^{12}$ are each independently selected from the group consisting of H and alkyl.

23. The method of claim 16, wherein $R^8$, $R^9$, $R^{12}$, and $R^{13}$ are H; and $R^6$ and $R^7$, together with the ring carbon to which they are attached, form —C(O)—.

24. The method of claim 1, having the stereochemical structure:

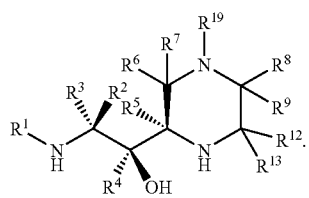

25. The method of claim 1, wherein said compound, or a pharmaceutically acceptable salt thereof, is selected from the group consisting of:

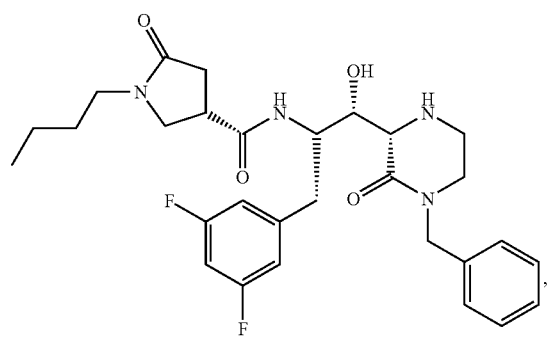

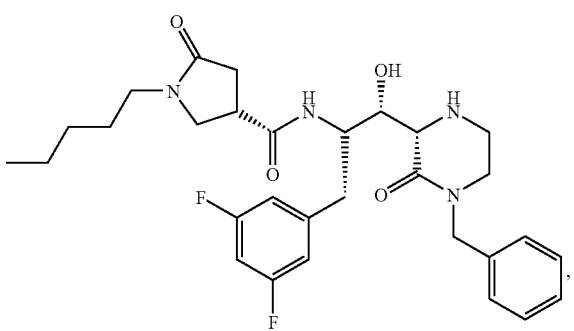

-continued

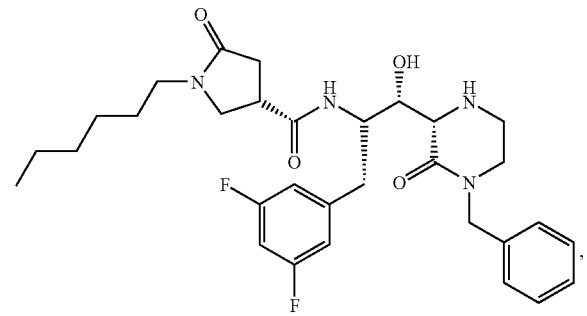

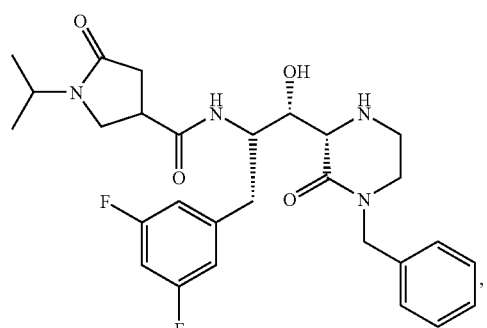

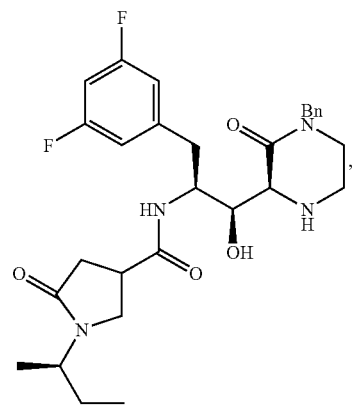

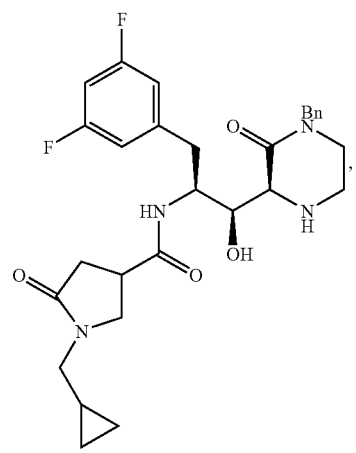

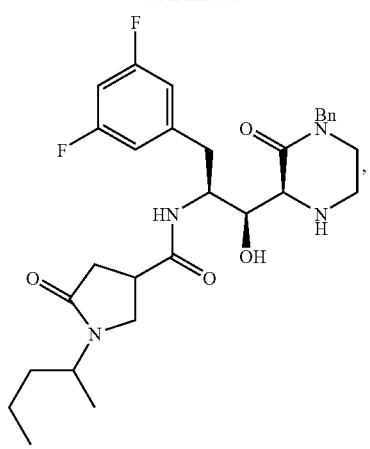,
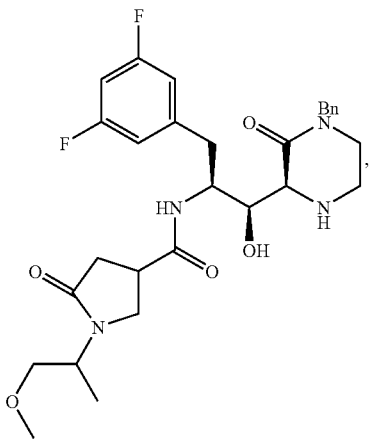,
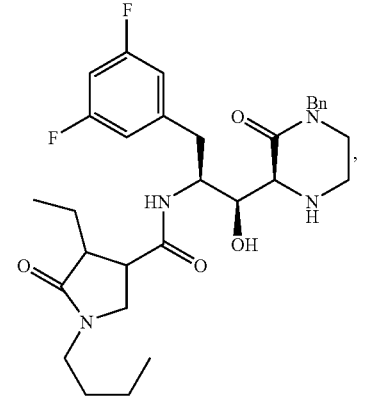,
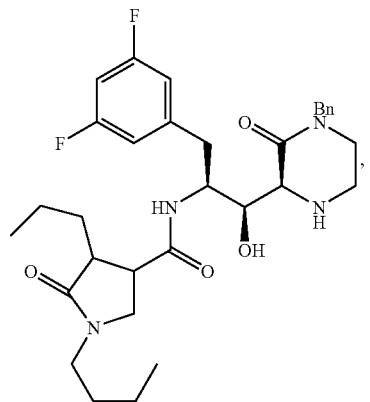,
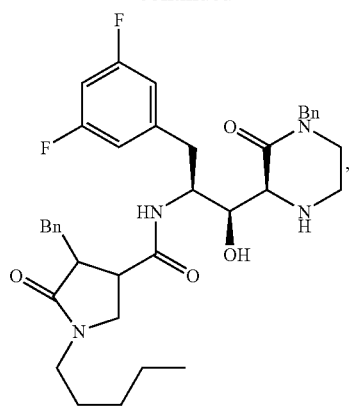,
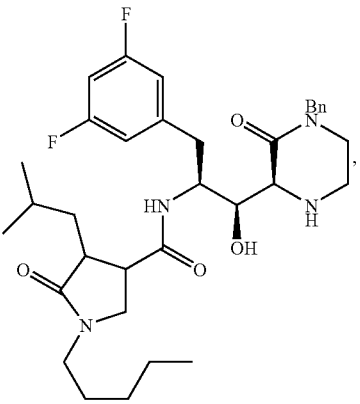,
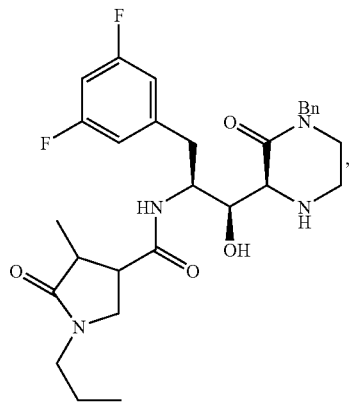,
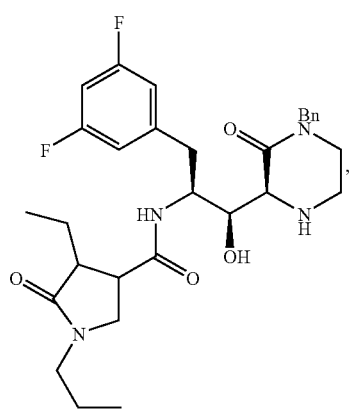, -continued

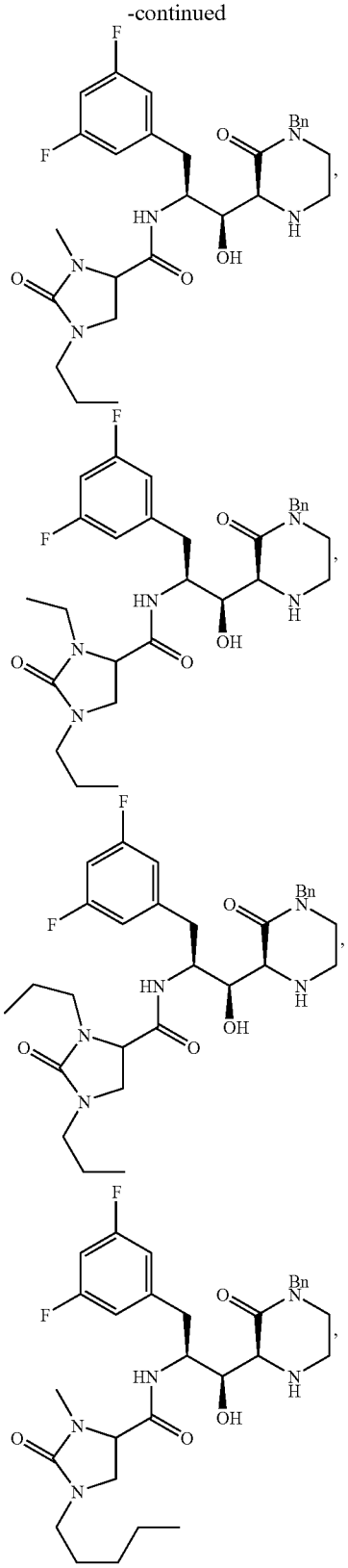

-continued

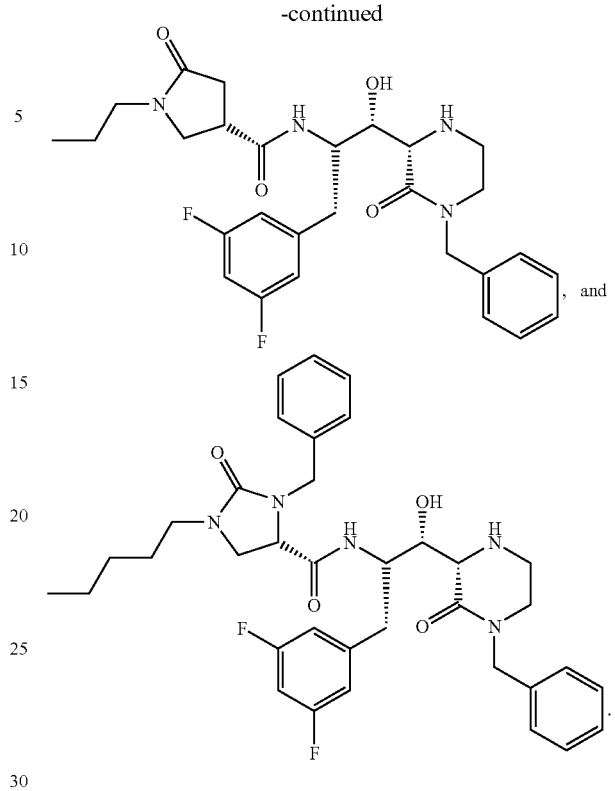

26. A method according to claim 1 or claim 25, wherein an effective amount of said compound, or a pharmaceutically acceptable salt thereof, is administered in combination with an effective amount of at least one additional active agent selected from the group consisting of: a BACE-1 inhibitor other than those of Formula (I), an HMG-CoA reductase inhibitor, a gamma-secretase inhibitor, a non-steroidal anti-inflammatory agent, an N-methyl-D-aspartate receptor antagonist, a cholinesterase inhibitor and an anti-amyloid antibody.

27. A method of claim 26, wherein said at least one additional active agent is at least one HMG-CoA reductase inhibitor selected from the group consisting of atorvastatin, lovastatin. simvistatin, pravastatin, fluvastatin and rosuvastatin.

28. A method of claim 26, wherein said at least one additional active agent is at least one cholinesterase inhibitor selected from the group consisting of tacrine, donepezil, rivastigmine, galantamine, pyridostigmine and neostigmine.

29. A method of claim 26, wherein said at least one additional active agent is at least one non-steroidal anti-inflammatory agent selected from the group consisting of ibuprofen, naproxen, diclofenac, diflunisal, etodolac, flurbiprofen, indomethacin, ketoprofen, ketorolac, nabumetone, oxaprozin, piroxicam, sulindac, tolmetin, celecoxib and rofecoxib.

30. A method of claim 26, wherein said at least one additional active agent is at least one N-methyl-D-aspartate receptor antagonist.

31. A method of claim 26, wherein said at least one additional active agent is memantine.

* * * * *